(12) United States Patent
Yoshimura et al.

(10) Patent No.: US 11,071,508 B2
(45) Date of Patent: Jul. 27, 2021

(54) X-RAY CT IMAGING APPARATUS

(71) Applicant: J. MORITA MANUFACTURING CORPORATION, Kyoto (JP)

(72) Inventors: Takahiro Yoshimura, Kyoto (JP); Tomoyuki Sadakane, Kyoto (JP); Yoshito Sugihara, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 0 days.

(21) Appl. No.: 16/434,176

(22) Filed: Jun. 7, 2019

(65) Prior Publication Data

US 2019/0374181 A1    Dec. 12, 2019

(30) Foreign Application Priority Data

Jun. 8, 2018 (JP) .............................. JP2018-110346

(51) Int. Cl.
*A61B 6/00* (2006.01)
*A61B 6/03* (2006.01)
*A61B 6/10* (2006.01)
*A61B 6/14* (2006.01)

(52) U.S. Cl.
CPC ............ *A61B 6/4476* (2013.01); *A61B 6/032* (2013.01); *A61B 6/102* (2013.01); *A61B 6/14* (2013.01); *A61B 6/4452* (2013.01)

(58) Field of Classification Search
None
See application file for complete search history.

(56) References Cited

U.S. PATENT DOCUMENTS

| | | | | |
|---|---|---|---|---|
| 2007/0041491 A1* | 2/2007 | Sadakane | ............... | A61B 6/589 378/15 |
| 2012/0039435 A1* | 2/2012 | Arai | ....................... | A61B 6/542 378/11 |
| 2015/0036800 A1 | 2/2015 | Takemoto et al. | | |
| 2015/0289833 A1 | 10/2015 | Yamanaka et al. | | |
| 2017/0188981 A1 | 7/2017 | Park et al. | | |
| 2018/0206801 A1* | 7/2018 | Lee | ........................ | A61B 6/588 |

FOREIGN PATENT DOCUMENTS

| | | |
|---|---|---|
| JP | 2007-29168 A | 2/2007 |
| JP | 2011-194032 A | 10/2011 |
| JP | 2012-055683 A | 3/2012 |
| JP | 2013-135765 A | 7/2013 |
| JP | 2014-090888 A | 5/2014 |
| WO | 2017/014476 A1 | 1/2017 |

OTHER PUBLICATIONS

Search Report from the corresponding European Patent Application No. 19179111.0 dated Oct. 23, 2019.
Office Action from the corresponding Japanese Patent Application No. 2018-110346 dated Mar. 30, 2021.

* cited by examiner

*Primary Examiner* — Hoon K Song
(74) *Attorney, Agent, or Firm* — Shinjyu Global IP

(57) ABSTRACT

When X-ray CT imaging is performed with a part located close to a front of a head as the imaging region, using the turning mechanism and the distance changing mechanism, the turning controller causes the X-ray generator and the X-ray detector to turn around the head while locating the imaging region therebetween, and causes the X-ray detector to turn along a go-around orbit, in which the X-ray detector comes close to the imaging region with respect to a front side of the head and moves away from the imaging region with respect to a rear side, by changing a distance between the X-ray detector and the center of the imaging region.

14 Claims, 18 Drawing Sheets

X-RAY CT IMAGING APPARATUS

CROSS-REFERENCE TO RELATED APPLICATIONS

This application claims priority to Japanese Patent Application No. 2018-110346, filed Jun. 8, 2018. That application is incorporated by reference in its entirety herein.

BACKGROUND

Technical Field

The present disclosure relates to an X-ray CT imaging apparatus that performs X-ray imaging by turning an X-ray generator and an X-ray detector around a subject.

Description of the Background Art

Japanese Patent Application Laid-Open No. 2007-029168 discloses an X-ray CT imaging apparatus including a turning mechanism and a moving mechanism. The turning mechanism turns a turning unit, in which the X-ray generator and the X-ray detector are disposed opposite to each other while the subject is sandwiched therebetween, around a turning axis. The moving mechanism moves the turning axis and/or the subject in a plane perpendicular to the turning axis. In the X-ray CT imaging apparatus, the turning unit is turned by combined movement of the turning of the turning unit and the turning axis and/or the movement of the subject while a center of an interest region of the subject is always set to a rotation center on the imaging different from the turning axis of the turning mechanism. Consequently, an enlargement ratio can be changed by relatively changing a distance between the X-ray generator and the rotation center and/or a distance between the X-ray detector and the rotation center.

When the X-ray detector is brought closer to the imaging region than the X-ray generator in turning the X-ray generator and the X-ray detector around the subject, a clear X-ray CT image can be obtained.

However, the center of the imaging region is not necessarily matched with the center of the subject. For this reason, when the X-ray generator and the X-ray detector are turned at a constant enlargement ratio on a condition that the X-ray detector is brought closer to the imaging region than the X-ray generator, the X-ray detector can come into contact with the subject.

SUMMARY

An object of the present disclosure is to obtain a clear X-ray CT image by turning the X-ray generator as close to the head as possible while preventing the X-ray generator and the X-ray detector, which turns around the subject, from contacting the head.

According to a first aspect, an X-ray CT imaging apparatus that performs X-ray CT imaging with a part of a head as an imaging region, the X-ray CT imaging apparatus includes: an X-ray generator that generates an X-ray; an X-ray detector that detects the X-ray; a turning support that supports the X-ray generator and the X-ray detector in an opposed state; a shaft located between the X-ray generator and the X-ray detector; a first motor that turns the turning support around the shaft; a second motor that moves the shaft to change a distance of the X-ray detector with respect to a center of the imaging region when the first motor turns the turning support; and a processor that controls the first motor and the second motor. When the X-ray CT imaging is performed with the part located close to a front of the head as the imaging region, using the first motor and the second motor, the processor causes the X-ray generator and the X-ray detector to turn around the head while locating the imaging region between the X-ray generator and the X-ray detector, and the processor changes the distance of the X-ray detector with respect to the center of the imaging region, so that the processor causes the X-ray detector to turn along a go-around orbit that comes close to the imaging region with respect to a front side of the head and moves away from the imaging region with respect to a rear side of the head.

The X-ray detector is turned along the go-around orbit, which comes close to the imaging region with respect to a front side of the head and moves away from the imaging region with respect to a rear side of the head, by changing the distance between the X-ray detector and the center of the imaging region, so that the X-ray detector can turns as close to the head as possible while the X-ray generator and the X-ray detector, which turn around the head, are prevented from coming into contact with the head, and the clear X-ray CT image can be obtained.

According to a second aspect, in the X-ray CT imaging apparatus of the first aspect, the go-around orbit is an orbit that does not include a portion concave toward the imaging region.

Consequently, the change in the inward and outward directions of the X-ray detector decreases, and the X-ray detector is hardly shaken.

According to a third aspect, in the X-ray CT imaging apparatus of the second aspect, the processor causes the X-ray detector to turn along the circular or elliptic go-around orbit, which comes close to the imaging region with respect to the front side of the head and moves away from the imaging region with respect to the rear side.

The X-ray detector is turned along the circular or elliptical go-around orbit, so that the X-ray detector is hardly shaken.

According to a fourth aspect, in the X-ray CT imaging apparatus of any one of the first to third aspects, the imaging region is a front tooth region, and the X-ray detector comes closest to the imaging region at a front of the head in the go-around orbit.

The X-ray detector comes closest to the imaging region at the front of the head, so that the clear X-ray CT image of the front tooth region can be obtained.

According to a fifth aspect, in the X-ray CT imaging apparatus of any one of the first to fourth aspects, the go-around orbit includes an equidistance moving orbit in which the X-ray detector moves while keeping an equidistance with respect to the center of the imaging region when the X-ray detector passes through a portion located close to the front of the head, and the remaining orbit of the equidistance moving orbit in the go-around orbit is a distance changing and moving orbit in which the X-ray detector moves while changing the distance to the center (A) of the imaging region.

In the equidistant moving orbit, the X-ray detector moves while maintaining the equidistance from the center of the imaging region, so that the X-ray detector is hardly shaken, and the clear X-ray CT image is easily generated.

According to a sixth aspect, in the X-ray CT imaging apparatus of any one of the first to fourth aspects, the go-around orbit is an orbit along which the X-ray detector moves while changing the distance with respect to the center of the imaging region in a whole circumference of the head.

The movement of the X-ray detector in an inner circumferential direction and an outer circumferential direction can smoothly be changed, the X-ray detector is hardly shaken, and the clear X-ray CT image is easily generated.

According to a seventh aspect, in the X-ray CT imaging apparatus of any one of the first to sixth aspects, when the X-ray CT imaging is performed on a first imaging region including a front tooth region as the part located close to the front of the head, the processor causes the X-ray detector to turn along the go-around orbit, and when the X-ray CT imaging is performed on a second imaging region including a molar tooth as the imaging region, using the first motor and the second motor, the processor causes the X-ray generator and the X-ray detector to turn around the head while positioning the imaging region between the X-ray generator and the X-ray detector such that a proportion of a minimum value of a distance between the center of the second imaging region and the X-ray detector to a maximum value of the distance is greater than a proportion of a minimum value of a distance between the center of the first imaging region and the X-ray detector to a maximum value of the distance.

In the case that the X-ray CT imaging is performed with the first imaging region including the front teeth region as the imaging region, because the rear of the head is relatively far away from the center of the imaging region, the X-ray detector easily comes into contact with the rear of the head. On the other hand, in the case that the X-ray CT imaging is performed with the second imaging region including the molar region as the imaging region, the rear of the head or the side opposite to the molar tooth is not separated so much from the center of the imaging region. In the seventh aspect, the X-ray generator and the X-ray detector are turned such that the proportion of the minimum value to the maximum value of the distance between the X-ray detector and the center of the second imaging region is greater than the proportion of the minimum value to the maximum value of the distance between the X-ray detector and the center of the first imaging region. Consequently, when the X-ray CT imaging is performed on the first imaging region, the X-ray detector hardly contacts with the head. Further, in the case that the X-ray CT imaging is performed on the second imaging region, the movement of the X-ray detector in the inner circumferential direction and the outer circumferential direction can smoothly be changed, the X-ray detector is hardly shaken, and the clear X-ray CT is easily generated.

According to an eighth aspect, the X-ray CT imaging apparatus of any one of the first to seventh aspects includes the second motor that moves the shaft in a direction crossing an axial direction of the shaft. The second motor moves the shaft in synchronization with the turning of the turning support about the shaft by the first motor, and the processor controls the go-around orbit of the X-ray detector with respect to the head by causing the turning support to perform combined movement.

In synchronization with the turning of the turning support about the shaft using the first motor, the second motor moves the shaft to cause the turning support to perform the combined movement, whereby the go-around orbit of the X-ray detector with respect to the head can be controlled.

According to a ninth aspect, in the X-ray CT imaging apparatus of the eighth aspect, the go-around orbit of the X-ray detector includes a first orbit approaching the imaging region on a side where the imaging region is biased in the head and a second orbit moving away from the imaging region on a side opposite to the side where the imaging region is biased in the head, and the go-around orbit is formed by a motion in which the second motor changes a position of the shaft in each of the first orbit and the second orbit in a direction parallel to the direction in which the imaging region is biased with respect to the center of the head.

The first orbit that comes close to the imaging region on the side on which the imaging region is biased in the head and the second orbit that moves away from the imaging region on the side opposite to the side on which the imaging region is biased in the head can be formed by changing the position of the shaft to a direction parallel to the direction in which the imaging region is biased with respect to the center of the head.

According to a tenth aspect, in the X-ray CT imaging apparatus of the eighth or ninth aspect, in a period during which the X-ray detector turns, the shaft is located in the center of the imaging region in at least a part of the period in which the X-ray detector passes through a portion of the go-around orbit located close to the front of the head, and the shaft moves in another period.

Because the shaft is located in the center of the imaging region in at least a part of the period during which the X-ray detector passes through the portion located close to the front of the head, the X-ray detector is hardly shaken, and the clear X Line CT image is easily generated.

According to an eleventh aspect, in the X-ray CT imaging apparatus of the eighth or ninth aspect, the shaft moves during a whole period in which the X-ray detector turns.

When the X-ray detector moves around the whole head, the shaft moves in the period during which the X-ray detector turns. Consequently, the movement of the X-ray detector can smoothly be changed on the inner circumferential side and the outer circumference side, the X-ray detector is hardly shaken, and the clear X-ray CT image is easily generated.

According to a twelfth aspect, in the X-ray CT imaging apparatus of any one of the first to eleventh aspects, the X-ray generator and the X-ray detector turn while a state in which a center line of the X-ray emitted from the X-ray generator passes through the center of the imaging region is maintained.

The center line of the X-ray emitted from the X-ray generator passes through the center of the imaging region, and is incident on the X-ray detector. The X-ray CT image can easily be generated based on the detection result of the X-ray detector.

According to a thirteenth aspect, the X-ray CT imaging apparatus of any one of the first to twelfth aspects includes the second motor that adjusts a curvature of the go-around orbit by adjusting the distance between the center of the imaging region and the X-ray detector when the first motor turns the X-ray generator. When the X-ray CT imaging is performed with the part located close to the front of the head as the imaging region, using the first motor and the second motor, the processor causes the X-ray generator and the X-ray detector to turn around the head while locating the imaging region between the X-ray generator and the X-ray detector, and the processor changes the distance between the X-ray detector and the center of the imaging region, so that the turning controller changes the curvature of the go-around orbit.

By changing the curvature of the circling orbit of the X-ray detector, the X-ray detector can be turned along the go-around orbit, which comes close to the imaging region with respect to the front side of the head and moves away from the imaging region with respect to the rear side.

According to a fourteenth aspect, in the X-ray CT imaging apparatus of the thirteenth aspect, when the X-ray CT imaging is performed with a front tooth region as the imaging region, using the first motor and the second motor, the processor causes the X-ray generator and the X-ray detector to turn around the head while locating the imaging region between the X-ray generator and the X-ray detector, and the processor changes the curvature of the go-around orbit of the X-ray detector with respect to the head, so that the processor causes the X-ray detector to turn along the go-around orbit that comes close to the imaging region with respect to the front side of the head and moves away from the imaging region with respect to the rear side of the head, and when the X-ray CT imaging is performed with a region different from the front tooth region in the head as the imaging region, a distance between the X-ray detector and the center of the imaging region is kept constant, the processor turns the X-ray generator and the X-ray detector around the head while locating the imaging region between the X-ray generator and the X-ray detector.

In the case that the X-ray CT imaging is performed on the region of the head different from a front tooth region as the imaging region, the distance between the X-ray detector and the center of the imaging region is kept constant, and the X-ray generator and the X-ray detector are turned around the head while the imaging region is located therebetween, so that the X-ray generator and the X-ray detector draws the stable go-around orbit. Consequently, the clear X-ray CT image is easily obtained.

According to a fifteenth aspect, in the X-ray CT imaging apparatus of any one of the first to fourteenth aspects, when the X-ray CT imaging is performed with the part located close to the front of the head as the imaging region, the processor causes the first motor to turn the X-ray generator and the X-ray detector at least 360°.

The X-ray CT imaging can be performed by turning the X-ray generator and the X-ray detector at least 360°.

According to a sixteenth aspect, an X-ray CT imaging apparatus that performs X-ray CT imaging with a part of a head as an imaging region, the X-ray CT imaging apparatus includes: an X-ray generator that generates an X-ray; an X-ray detector that detects the X-ray; a turning support that supports the X-ray generator and the X-ray detector in an opposed state; a turning mechanism that turns the turning support with a mechanical turning axis located between the X-ray generator and the X-ray detector as a center; a distance changing mechanism that moves the mechanical turning axis to change a distance of the X-ray detector with respect to the center of the imaging region when the turning mechanism turns the turning support; and a processor. When the X-ray CT imaging is performed with the part located close to a front of the head as the imaging region, using the turning mechanism and the distance changing mechanism, the processor causes the X-ray generator and the X-ray detector to turn around the head while locating the imaging region between the X-ray generator and the X-ray detector, and the processor changes the distance of the X-ray detector with respect to the center of the imaging region, so that the processor causes the X-ray detector to turn along a go-around orbit that comes close to the imaging region with respect to a front side of the head and moves away from the imaging region with respect to a rear side of the head.

The X-ray detector is turned along the go-around orbit, which comes close to the imaging region with respect to a front side of the head and moves away from the imaging region with respect to a rear side of the head, by changing the distance between the X-ray detector and the center of the imaging region, so that the X-ray detector can turns as close to the head as possible while the X-ray generator and the X-ray detector, which turn around the head, are prevented from coming into contact with the head, and the clear X-ray CT image can be obtained.

These and other objects, features, aspects and advantages of the present disclosure will become more apparent from the following detailed description of the present disclosure when taken in conjunction with the accompanying drawings.

DETAILED DESCRIPTION

Figure 1:
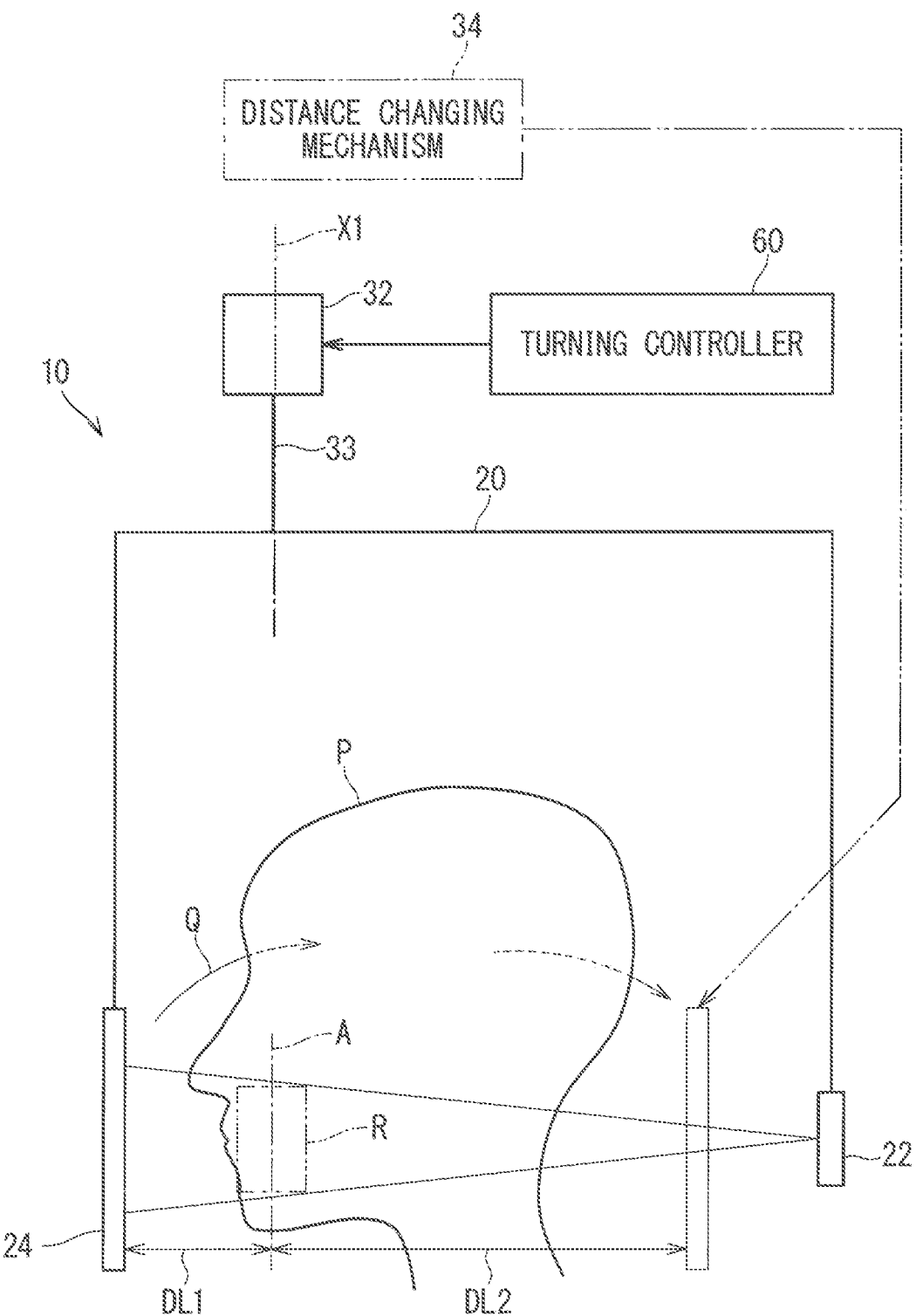
FIG. 1 is a schematic diagram illustrating an X-ray CT imaging apparatus according to a first embodiment.

A medical X-ray CT imaging apparatus according to a first preferred embodiment will be described. FIG. 1 is a schematic diagram illustrating an X-ray CT imaging apparatus 10.

The X-ray CT imaging apparatus 10 is an apparatus that performs X-ray CT imaging with a part of a head P as an imaging region R. The imaging region R may be set in a columnar shape with a vertical direction of the head P as a center axis or a spherical shape. The X-ray CT imaging apparatus 10 is an apparatus that performs X-ray CT (Computed Tomography) imaging of the head P of the subject. The X-ray CT imaging apparatus 10 includes an X-ray generator 22, an X-ray detector 24, a turning support 20, a turning mechanism 32, a distance changing mechanism 34, and a turning controller 60.

The X-ray generator 22 generates an X-ray. An irradiation range of the X-ray emitted from the X-ray generator 22 is restricted by a restriction unit, whereby an X-ray cone beam may be formed.

The X-ray detector 24 detects the X-ray generated by the X-ray generator 22.

The turning support 20 supports the X-ray generator 22 and the X-ray detector 24 in an opposed state. The X-ray generator 22 and the X-ray detector 24 are opposed to each other with a space capable of disposing the head P therebetween. The X-ray emitted from the X-ray generator 22 is incident on the X-ray detector 24 through the head P. The X-ray incident on the X-ray detector 24 is converted into an electric signal corresponding to intensity of the X-ray in each unit pixel. The X-ray CT image or the like is generated based on each electric signal.

The turning mechanism 32 turns the turning support 20 about a turning axis X1 on a mechanism (also be able to be called as "a mechanical turning axis X1") located between the X-ray generator 22 and the X-ray detector 24. For example, the turning mechanism 32 includes an electric motor, and includes an acceleration or deceleration mechanism such as a gear as necessary. The turning mechanism 32 rotatably supports a shaft (an axis member) 33 protruding from the turning support 20 at a position between the X-ray generator 22 and the X-ray detector 24. The center axis of the shaft 33 constitutes the turning axis X1 on the mechanism. The turning support 20 turns about the turning axis X1 on the mechanism by driving the turning mechanism 32. The turning mechanism 32 may have any configuration as long as the turning support 20 is turned about the turning axis X1 on the mechanism.

In performing the X-ray CT imaging under the control of the turning controller 60, the turning mechanism 32 turns the X-ray generator 22 and the X-ray detector 24 at least 360° around the head P. The turning axis X1 may be closer to the X-ray detector 24 than the X-ray generator 22.

The distance changing mechanism 34 is a mechanism that change a distance between the X-ray detector 24 and a center A of the imaging region R when the turning mechanism 32 turns the turning support 20. The distance changing mechanism 34 may change the distance between the X-ray detector 24 and the center A of the imaging region R by changing a position of the turning axis X1 on the mechanism. The distance changing mechanism 34 may change the distance between the X-ray detector 24 and the center A of the imaging region R by changing the position of the X-ray detector 24 with respect to the turning axis X1 on the mechanism.

The turning controller 60 controls the turning mechanism 32 and the distance changing mechanism 34. The turning controller 60 includes at least one processor. For example, the turning controller 60 is constructed with a computer including at least one processor, a RAM (Random Access Memory), a storage, and an input and output unit. The storage is constructed with a nonvolatile storage device such as a flash memory or a hard disk drive, and stores a turning control program controlling the turning mechanism 32 and the distance changing mechanism 34. The RAM serves as a work area when at least one processor performs predetermined processing. The input and output unit is connected to the turning mechanism 32 and the distance changing mechanism 34. The at least one processor performs predetermined calculation processing according to the turning control program stored in the storage, thereby controlling the turning mechanism 32 and the distance changing mechanism 34.

Figure 2:
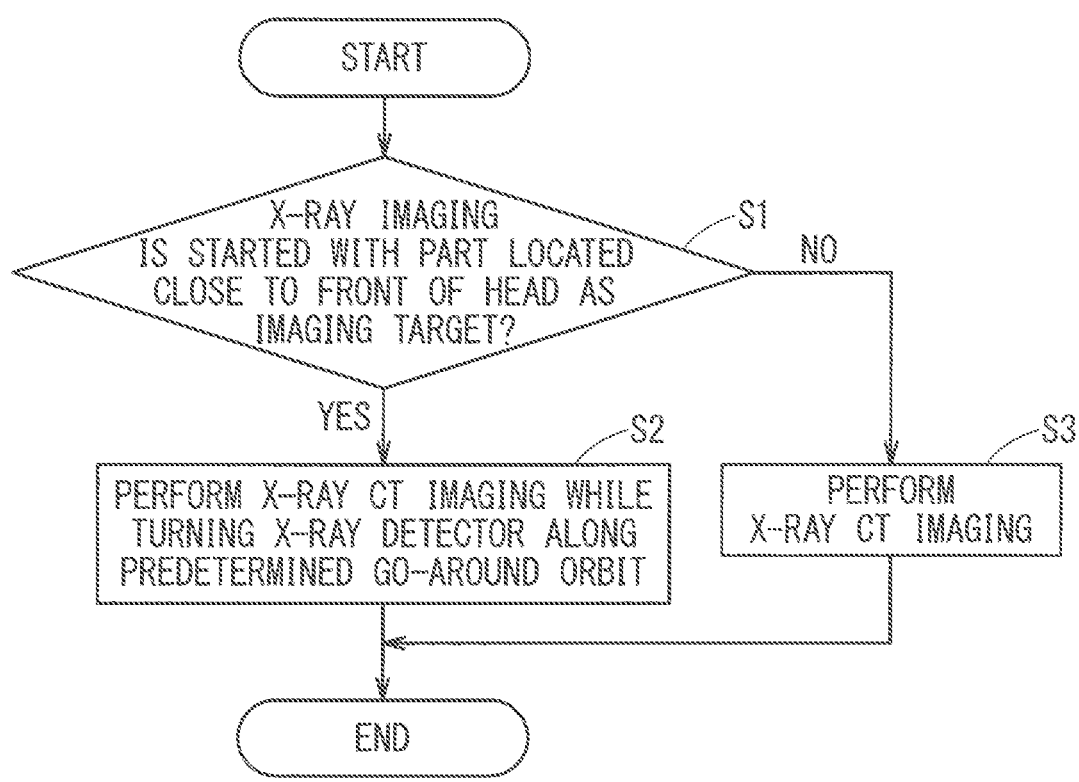
FIG. 2 is a flowchart illustrating an example of processing performed by a turning controller.

FIG. 2 is a flowchart illustrating processing performed by the turning controller 60.

That is, in performing the X-ray CT imaging, whether or not the X-ray CT imaging is performed on a part located close to the front of the head P is determined in step S1. For example, when an operator inputs the performance of the X-ray CT imaging with a part located close to the front of the head P as the imaging region R through a setting receiving unit such as a touch panel and a switch, an affirmative determination is made in step S1. A negative determination is made in other cases, known X-ray CT imaging is performed in step S3, and the processing is ended. In the first preferred embodiment, for example, the turning support 20 is turned about the turning axis X1 on the mechanism while the state in which the position of the turning axis X1 on the mechanism is matched with the position of the center A of the imaging region R is maintained, which allows the X-ray generator 22 and the X-ray detector 24 to be turned along the circular go-around orbit about the center A of the imaging region R. A region that is a partial region rather than the whole region of the object in the XY-direction when viewed from an axial direction of a body axis, such as a part existing close to the front of the head P, may be called a local region.

In step S2, the turning controller 60 controls the turning mechanism 32 and the distance changing mechanism 34 to turn the X-ray detector 24 along a predetermined go-around orbit Q, thereby performing the X-ray CT imaging.

As used herein, the "predetermined go-around orbit Q" means a go-around orbit in which the X-ray detector 24 comes closer to the imaging region R with respect to the front side of the head P and moves away from the imaging region R with respect to the rear side of the head P. When the negative determination is made in step 1, the known X-ray CT imaging in which the X-ray detector 24 does not come close to and move away from the imaging region R is performed in step S3.

It is assumed that the X-ray generator 22 and the X-ray detector 24 can be turned only by driving the turning mechanism 32. In this case, the X-ray generator 22 and the X-ray detector 24 turn while drawing the circular go-around orbit centered on the turning axis X1 on the mechanism. In order to image the imaging region R, the X-ray generator 22 and the X-ray detector 24 are turned along the circular go-around orbit about the center A of the imaging region R while the turning axis X1 on the mechanism is matched with the center A of the imaging region R.

In this case, when the X-ray detector 24 passes through the front side of the head P, approach of the X-ray detector 24 to the imaging region R can obtain a clear X-ray CT image. A turning diameter of the X-ray detector 24 can also be decreased. However, the distance from the center A of the imaging region R to a rear portion of the head P is larger than the distance from the center A of the imaging region R to a front portion of the head P. When the X-ray detector 24 is excessively brought close to the center A of the imaging region R, the X-ray detector 24 can come into contact with the head P during the passage of the X-ray detector 24 through the rear side of the head P.

However, when the X-ray detector 24 is excessively moved away from the imaging region R, the clear X-ray CT image is hardly obtained. The turning diameter of the X-ray detector 24 becomes large around a whole circumference of the head P.

For this reason, in the case that the X-ray CT imaging is performed with a part located close to the front of the head P as the imaging region R, using the turning mechanism 32 and the distance changing mechanism 34, the turning controller 60 causes the X-ray generator 22 and the X-ray detector 24 to turn around the head P while locating the imaging region R between the X-ray generator 22 and the X-ray detector 24. At this point, the X-ray detector 24 is turned along the go-around orbit Q, which comes close to the imaging region R with respect to the front side of the head P and moves away from the imaging region R with respect to the rear side, by changing a distance DL1 and a distance DL2 between the X-ray detector 24 and the center A of the imaging region R using the distance changing mechanism 34. The fact that the X-ray detector 24 comes close to the imaging region R with respect to the front side of the head P means that the X-ray detector 24 comes close to the imaging region R rather than the case that the X-ray detector 24 passes through the rear side of the head part P. Similarly, the fact that the X-ray detector 24 moves away from the imaging region R with respect to the rear of the head P means that the X-ray detector 24 moves away from the imaging region R rather than the case that the X-ray detector 24 passes through the front side of the head P.

In FIG. 1, the distance between the X-ray detector 24 and the center A of the imaging region R becomes the distance DL1 in the state in which the X-ray detector 24 is located on the front side of the head P, and the X-ray detector 24 comes close to the imaging region R. The distance between the X-ray detector 24 and the center A of the imaging region R becomes the distance DL2 larger than the distance DL1 in the state in which the X-ray detector 24 is located on the rear side of the head P, and the X-ray detector 24 moves away from the imaging region R. The distance between the X-ray detector 24 and the center A of the imaging region R may gradually increase from the distance DL1 to the distance DL2 in at least a part of the orbit in which the X-ray detector 24 moves from the front portion to the rear portion of the head P. The distance between the X-ray detector 24 and the center A of the imaging region R may gradually decrease from the distance DL2 to the distance DL1 in at least a part of the orbit in which the X-ray detector 24 moves from the rear portion to the front portion of the head P.

In the X-ray CT imaging apparatus 10 having this configuration, the X-ray detector 24 is turned along the go-around orbit Q, which comes close to the imaging region R with respect to the front side of the head P and moves away from the imaging region R with respect to the rear side, by changing the distance between the X-ray detector 24 and the center A of the imaging region R. Consequently, the X-ray detector 24 can be turned as close to the head P as possible while the X-ray generator 22 and the X-ray detector 24, which turn around the head P, are prevented from contacting with the head P, and the clear X-ray image can be obtained.

Second Preferred Embodiment

An X-ray CT imaging apparatus according to a second preferred embodiment will be described.

Figure 3:
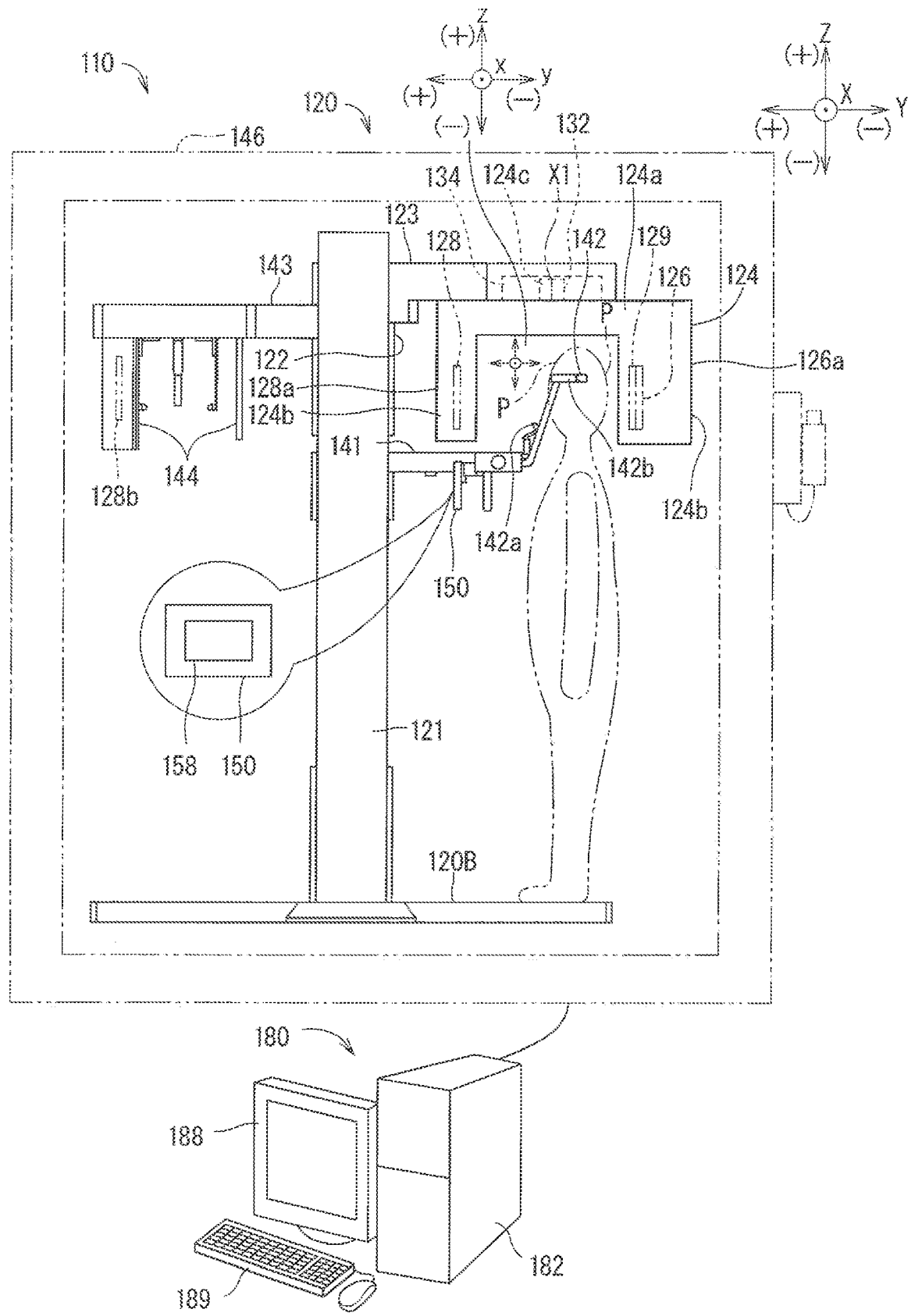
FIG. 3 is a schematic diagram illustrating a whole configuration of an X-ray CT imaging apparatus according to a second embodiment.

FIG. 3 is a schematic diagram illustrating a whole configuration of an X-ray CT imaging apparatus 110. At this point, an example in which the X-ray CT imaging apparatus 110 can perform not only the X-ray CT imaging but also panoramic imaging, cephalogram imaging, and the like will be described. The X-ray CT imaging apparatus 110 is an example of an apparatus that performs the X-ray CT imaging with a part of the head P as the imaging region.

<Whole Configuration>

The X-ray CT imaging apparatus 110 includes an imaging main body 120 and an X-ray image processing apparatus 180. The imaging main body 120 is an apparatus that performs X-ray imaging such as the X-ray CT imaging to collect projection data. The X-ray image processing apparatus 180 is an apparatus, which processes the projection data collected by the imaging main body 120 and generates various images.

The imaging main body 120 includes an X-ray generator 126, an X-ray detector 128, a turning support 124, a turning mechanism 132, and a turning axis moving mechanism 134 that is the distance changing mechanism.

The turning support 124 supports the X-ray generator 126 and the X-ray detector 128 such that the X-ray generator 126 and the X-ray detector 128 are opposed to each other with the head P interposed therebetween.

The turning mechanism 132 is a mechanism that turns the turning support 124 about the turning axis X1 on the mechanism (also be able to be called as "a mechanical turning axis X1") between the X-ray generator 126 and the X-ray detector 128.

The turning axis moving mechanism 134 is a mechanism that moves the turning axis X1 on the mechanism in a direction crossing the turning axis X1. When the turning mechanism 132 turns the turning support 124 supporting the X-ray generator 126 and the X-ray detector 128, the turning axis moving mechanism 134 moves the turning axis X1 on the mechanism, which allows the change in the distance between the X-ray detector 128 and the center A of the imaging region R.

More specifically, a post 121 is vertically supported on a base 120B. A lifting unit 122 is liftably provided on the post 121. A lifting drive mechanism causes the lifting unit 122 to move up and down. A linear actuator such as a moving mechanism including a ball screw mechanism and a motor or a linear motor is used as the lifting drive mechanism, and the lifting drive mechanism causes the lifting unit 122 to move up and down while being incorporated in the post 121. A horizontal arm 123 is supported by the lifting unit 122 so as to extend in a horizontal direction. The turning axis moving mechanism 134 and the turning mechanism 132 are incorporated at a leading end of the horizontal arm 123. A head fixing apparatus arm 141 (to be described later) extends from the post 121 in the same direction as the horizontal arm 123. A head fixing apparatus 142 is provided at the leading end of the head fixing apparatus arm 141, and the head P is held by the head fixing apparatus 142. In FIG. 3, a base end of the lifting unit 122 moves up and down behind the post 121. Assuming that the side on which the base end of the lifting unit 122 moves up and down is a back face and that a reverse of the back face is a front face, the horizontal arm 123 extends from the lifting unit 122 to the right of the post 121 in a front view in FIG. 3. The head P is held in the head fixing device 142 with the right in FIG. 3 set to the rear and the left set to the front.

At this point, the direction is defined for convenience.

An XYZ orthogonal coordinate system is an orthogonal coordinate system defined in a three-dimensional space in which the imaging main body 120 is installed. A direction parallel to the axial direction of the turning axis X1 on the mechanism is a Z axis direction. In the second preferred embodiment, the direction parallel to the axial direction of the turning axis X1 on the mechanism and the lifting direction of the lifting unit 122 are matched with each other while set to the Z axis direction. A direction orthogonal to the Z axis direction is a Y axis direction, and a direction orthogonal to the Z axis direction and the Y axis direction is an X axis direction. A front-back direction of the head P fixed to the head fixing apparatus 142 is set to the Y axis direction, and a right and left direction of the head P is set to the X axis direction. In the present disclosure, sometimes the Z axis direction is referred to as a Z direction, the Y axis direction is referred to as a Y direction, and the X axis direction is referred to as an X direction.

The direction from the head P toward the base 120B, namely, the lower side is set to a −Z side, and the direction away from the base 120B from the head P, namely, the upper side is set to a +Z side. The front side of the head P is set to a +Y side, and the rear side is set to a −Y side. The right side of the head P is set to an +X side, and the left side is set to an −X side. Each axis direction and "+" and "−" are illustrated in FIG. 3.

An xyz orthogonal coordinate system is an orthogonal coordinate system defined in the turning support 124 constituting an imaging system that performs X-ray generation and X-ray detection, the imaging system rotating about the turning axis X1 on the mechanism. At this point, the axial direction of the turning axis X1 on the mechanism is set to a z axis direction, and the z axis direction is matched with the Z axis direction of the XYZ orthogonal coordinate system. A direction in which the X-ray generator 126 and the X-ray detector 128 are opposed to each other is set to a y axis direction, and a direction orthogonal to the y axis direction and the z axis direction is set to an x axis direction. The turning support 124 rotates with the turning axis X1 on the mechanism as a rotation axis, which allows the xyz orthogonal coordinate system to rotate around the Z axis (=z axis) with respect to the XYZ orthogonal coordinate system. In the present disclosure, sometimes the z axis direction is referred to as a z direction, the y axis direction is referred to as a y direction, and the x axis direction is referred to as an x direction.

In the y axis direction, the side of the X-ray detector 128 is set to a +y side, and the side of the X-ray generator 126 is set to a −y side. In the x-axis direction, the right side from the −y side toward the +y side is set to a +x side, and the left side is set to a −x side. In the z-axis direction, the upper side in the vertical direction is set to a +z side, and the lower side is set to a −z side.

Figure 4:
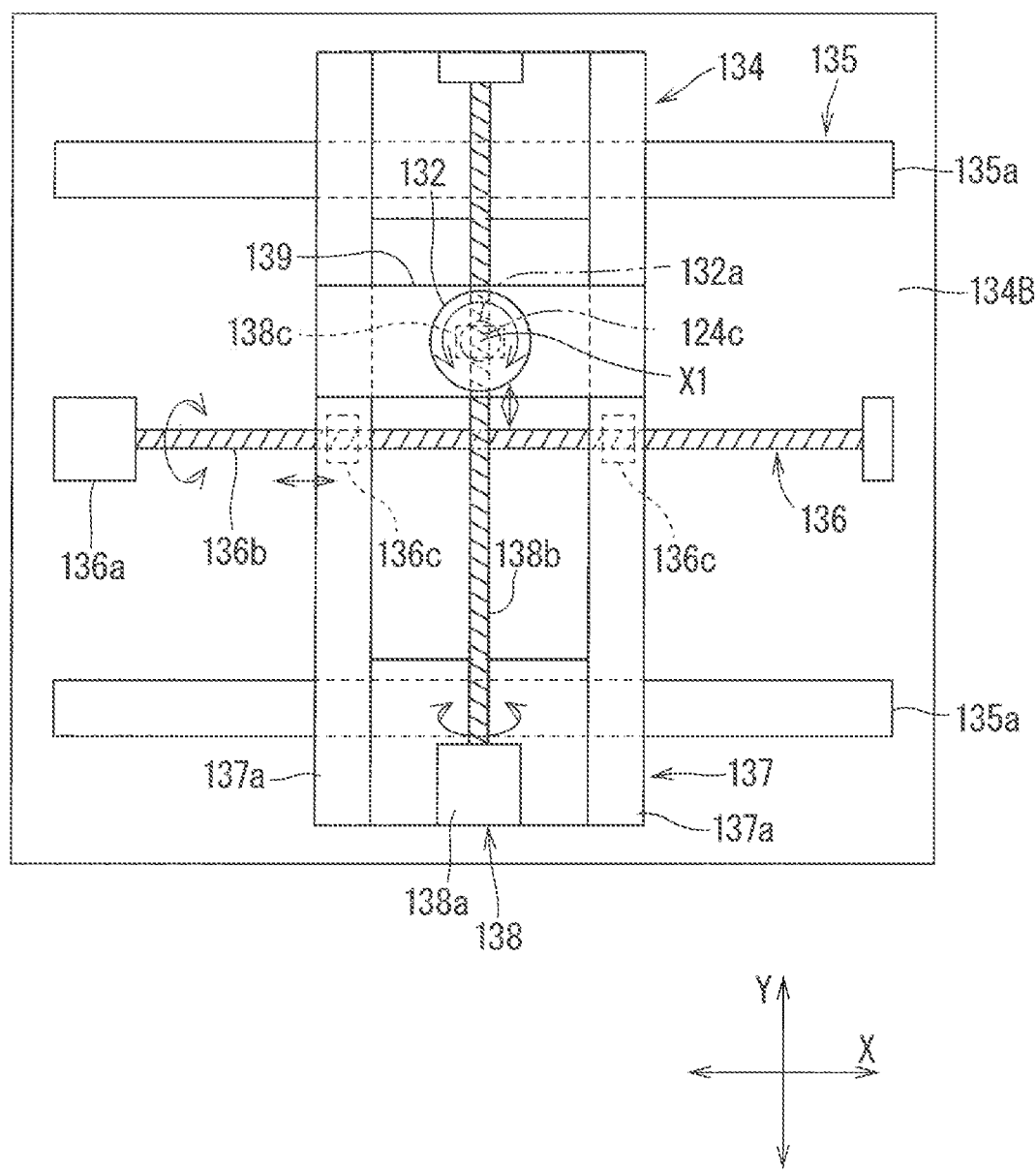
FIG. 4 is a schematic bottom view illustrating a turning axis moving mechanism.

FIG. 4 is a schematic bottom view illustrating the turning axis moving mechanism 134. As illustrated in FIGS. 3 and 4, the turning axis moving mechanism 134 is supported by the horizontal arm 123 that is a kind of bracket. The turning mechanism 132 is movably supported by the turning axis moving mechanism 134.

The turning axis moving mechanism 134 is a mechanism that moves the turning axis X1 on the mechanism in the direction crossing the turning axis X1 on the mechanism, in this case, the direction orthogonal to the turning axis X1 on the mechanism. The turning axis moving mechanism 134 is constructed with an XY table mechanism, and the turning axis X1 on the mechanism is moved in the direction crossing the turning axis X1 on the mechanism by moving the turning mechanism 132 to which the turning axis X1 on the mechanism is connected in the direction crossing the turning axis X1 on the mechanism. More specifically, the turning axis moving mechanism 134 includes a fixed table 134B, an X direction movable support 135, an X direction drive unit 136, a Y direction movable support 137, a Y direction drive unit 138, and a movable table 139.

The X direction movable support 135 includes a pair of linear guides 135a extending in the X direction, the linear guides 135a being supported on the fixed table 134B in a spaced and parallel state. The Y direction movable support 137 includes a pair of linear guides 137a extending in the Y direction. The pair of linear guides 137a are movably supported on the pair of linear guides 135a along the X direction that is the extending direction while having a posture crossing the pair of linear guides 135a (in this case, a posture orthogonal to the pair of linear guides 135a) in the spaced and parallel state. The movable table 139 is supported on the pair of linear guides 137a so as to be movable along the Y direction that is the extending direction. The Y direction movable support 137 moves along the X direction on the X direction movable support 135, which allows the movable table 139 to move in the X direction. The movable table 139 moves along the Y direction on the Y direction movable support 137, which allows the movable table 139 to move in the Y direction. Consequently, the movable table 139 can move freely in a plane orthogonal to the turning axis X1 on the mechanism.

The X direction drive unit 136 is a mechanism that reciprocally drives the Y direction movable support 137 along the X direction. For example, a ball screw mechanism in which a nut 136c fixed to the Y direction movable support 137 is screwed to a ball screw 136b rotationally driven in both forward and reverse directions by a motor 136a can be used as the X direction drive unit 136.

The Y direction drive unit 138 is a mechanism that reciprocally drives the movable table 139 along the Y direction. For example, a ball screw mechanism in which a nut 138c fixed to the movable table 139 is screwed to a ball screw 138b rotationally driven in both the forward and reverse directions by a motor 138a can be used as the Y direction drive unit 138.

The turning mechanism 132 includes a motor 132a, and is supported in a suspended state by the movable table 139. A shaft 124c (an axis member) protruding upward from an intermediate portion in the extending direction of the turning support 124 is supported in the suspended state by the turning mechanism 132. The shaft 124c is fixed to the turning support 124 so as not to be turnable. The rotating movement of the motor 132a is transmitted to the shaft 124c, and the turning support 124 is turned about the shaft 124c by driving the motor 132a. The center axis of the shaft 124c is the turning axis X1 on the mechanism. The turning axis X1 is located between the X-ray generator 126 and the X-ray detector 128, which are supported by the turning support 124. The rotating movement of the motor 132a is transmitted to the shaft 124c through a transmission mechanism such as a gear and a pulley as necessary. The shaft 124c is disposed along the vertical direction along a direction of gravity. Thus, the turning axis X1 on the mechanism is also disposed along the vertical direction. So the X-ray generator 126 and the X-ray detector 128 turn around the turning axis X1 which is located at the shaft 124c by the turning mechanism 132 and the motor 132a.

The turning mechanism 132 supported by the movable table 139 can be moved along the plane orthogonal to the turning axis X1 on the mechanism by driving the X direction drive unit 136 and the Y direction drive unit 138. The turning axis X1 on the mechanism can be moved with a desired orbit within a range of a mechanical restriction, and the linear movement in the direction of a sum of components in the X direction and components in the Y direction, the linear movement in the direction of a product of the components in the X direction and the components in the Y direction, and curvilinear movement can be performed by particularly combining the drive in the X direction by the X direction drive unit 136 and the drive in the Y direction by the Y direction drive unit 138 in addition to the linear movement in the X direction and the linear movement in the Y direction. The turning mechanism 132 can be rotated so as to draw a circular orbit, an arcuate orbit, or an orbit in which the circular orbit and the arcuate orbit are combined. For example, the movement in the X direction by the X direction drive unit 136 and the movement in the Y direction by the Y direction drive unit 138 are controlled with a turning angle at which the turning mechanism 132 turns the turn support 124 as a parameter, which allows the turning mechanism 132 to be moved in synchronization with the turning angle of the turning support 124.

The mechanism that moves the movable table 139 in the X direction and the mechanism that moves the movable table 139 in the Y direction are not limited to the above examples, but a configuration using a linear actuator such as a linear motor can be adopted. The turning axis moving mechanism 134 does not necessarily have the above configuration. The turning axis moving mechanism may be a mechanism, such as a robot arm including a plurality of joints, which turns an arm supporting the turning mechanism, thereby turning the turning mechanism in the direction crossing the turning axis X1 on the mechanism.

The turning mechanism may be provided in the turning support. For example, the turning axis moving mechanism may directly move the turning axis X1 on the mechanism with no use of the turning mechanism. As a more specific example, a shaft corresponding to the turning axis X1 on the mechanism is fixed to the movable table 139 so as not to be turnable and so as to be movable in the direction crossing the turning axis X1 on the mechanism, and the turning support 124 is turnably connected to the shaft. The turning mechanism 132 is provided in the turn support 124, and the turning mechanism 132 generates turning force with respect to the shaft, whereby the turning support 124 may be turned with respect to the shaft. Such a motor or motors such as the motor 132a described above (or motors described in the modifications) can be defined as first motor (as generic expression including even plurality of motors). The motors 136a and 138a can be defined as second motor (as generic expression including even plurality of motors).

As illustrated in FIG. 3, the turning support 124 is a portion that is supported such that the X-ray generator 126 and the X-ray detector 128 are opposed to each other with the head P interposed therebetween. The turning support 124 has a shape in which suspending supports 124b are provided at both ends of the elongated arm body 124a, namely, a U-shape that is open downward. The shaft 124c protruding upward is provided in the intermediate portion in the extending direction of the arm body 124a, and the shaft 124c is supported in the suspended state by the turning mechanism 132.

The X-ray generator 126 is provided in one suspending support 124b. The X-ray generator 126 generates the X-ray. For example, the X-ray generator 126 includes an X-ray tube, and is configured to be capable of outputting the X-ray emitted from the X-ray tube toward the X-ray detector 128.

An X-ray regulating unit 129 that regulates the X-ray generated from the X-ray generator 126 into an X-ray cone beam is provided on the side irradiated with the X-ray with respect to the X-ray detector 128. The X-ray regulating unit 129 is a member in which an X-ray regulating hole is made. The X-ray regulating unit 129 permits passage of part of the X-ray generated from the X-ray generator 126 according to the shape and size of the X-ray regulating hole, and shields an outside of the passage range of the X-ray. Consequently, the range of the X-ray beam proceeding to the X-ray detector 128 is regulated, and the X-ray is restricted into the X-ray cone beam. In the X-ray regulating unit 129, a plurality of types of X-ray regulating holes are made to switch the X-ray regulating holes regulating X-rays, or a member in which the X-ray regulating hole is made is moved to adjust an opening width of the X-ray regulating hole, thereby adjusting a shielded amount of the X-ray generated from the X-ray generator 126, namely, a regulated amount. The suspending support 124b on the side on which the X-ray generator 126 is provided is also an X-ray generation unit 126a including the X-ray generator 126.

The X-ray detector 128 is provided on the other suspending support 124b, so that the X-ray detector 128 is disposed so as to be opposed to the X-ray generator 126 with the head P interposed therebetween. The X-ray detector 128 detects the X-ray generated by the X-ray generator 126. For example, the X-ray detector 128 includes an X-ray detector having a planar detection surface, and is configured to be able to detect the X-ray (X-ray cone beam), which is emitted from the X-ray generator 126 and passes through the head P. The projection data by the X-ray imaging can be obtained by the X-ray detector 128. The suspending support 124b on the side on which the X-ray detector 128 is provided is also an X-ray detection unit 128a including the X-ray detector 128.

A space in which the head P can be disposed is provided between the X-ray generator 126 and the X-ray detector 128.

In the second preferred embodiment, the X-ray generator 126 and the X-ray detector 128 are attached to both ends of the U-shaped turning support. Alternatively, the X-ray generator and the X-ray detector may be supported by an annular member while opposed to each other. A shaft can be provided on a support member traversing a part in the circumferential direction or an inside of the annular member such that the annular member can turnably be supported. In the second preferred embodiment, the X-ray generator 126 and the X-ray detector 128 are supported so as to be rotatable around the vertical axis. Alternatively, the X-ray generator 126 and the X-ray detector 128 may be supported so as to be rotatable about an axis oblique to the vertical direction, or the X-ray generator 126 and the X-ray detector 128 may be supported so as to be rotatable about a horizontal axis.

The turning support 124 can be caused to move up and down by the lifting unit 122 according to a height of the head P. The turning support 124 can be turned by the turning mechanism 132 such that the X-ray generator 126 and the X-ray detector 128 turn around the head P.

The head fixing apparatus arm 141 extending in the horizontal direction is provided in a portion of the post 121 below the horizontal arm 123. The horizontal arm 123 and the head fixing apparatus arm 141 extend in the same direction with the side of the post 121 as the base end. The head fixing apparatus arm 141 extends toward the lower side of the horizontal arm 123, and the head fixing apparatus 142 is provided at a leading end of the head fixing apparatus arm 141. The head fixing apparatus 142 is located between the X-ray generator 126 and the X-ray detector 128. The head fixing apparatus 142 includes a chin rest 142a on which a chin of the head P that is the subject can be placed and supported and a holder 142b that holds the head P that is the subject while sandwiching the head P from both outsides. The chin of the head P is supported on the chin rest 142a, and the head P is sandwiched by the holder 142b, whereby the head P is held at a fixed position between the X-ray generator 126 and the X-ray detector 128. The head fixing apparatus 142 may be constructed with at least one of the chin rest 142a and the holder 142b. A cephalogram imaging head fixing apparatus suspending arm 143 is provided so as to extend in the horizontal direction on the side opposite to the side on which the horizontal arm 123 extends from the post 121, and a cephalogram imaging head fixing apparatus 144 is supported in the suspended state by the cephalogram imaging head fixing apparatus suspending arm 143. A cephalogram imaging X-ray detector 128b is incorporated in the cephalogram imaging head fixing apparatus 144.

A main body controller 150 including an operation panel apparatus 158 is provided in an intermediate portion in the extending direction of the head fixing apparatus arm 141. In FIG. 3, the operation panel apparatus 158 of the main body controller 150 is enlarged and drawn in a balloon.

The head fixing apparatus arm 141 may be configured to be able to move up and down. For example, the base end of the horizontal arm 141, namely, the portion of the horizontal arm 141 in a vicinity of the post 121 can be moved along a longitudinal direction of the post 121 by an appropriate guide member. At this point, the base end of the horizontal arm 141 is coupled to the lifting unit 122 so as to be able to move up and down behind the post 121. As to the coupling, for example, a power source such as a motor is fixed to the base end of the horizontal arm 141, a screw shaft is coupled to the rotation shaft of the motor, a receiving member of the screw shaft is fixed to the lifting unit 122, and the screw shaft is inserted in the receiving member of the screw shaft. With this configuration, not only the base end of the horizontal arm 141 but also the whole horizontal arm 141 can move up and down with respect to the lifting unit 122 by rotating the motor fixed to the base end of the horizontal arm 141.

With this configuration, a raise of the lifting unit 122 with respect to the post 121 and a fall of the horizontal arm 141 with respect to the lifting unit 122 are simultaneously performed with the same displacement amount, which allow the horizontal arm 123 and the turning support 124 to be raised with respect to the head P while the height of the head P fixed to the head fixing apparatus 142 is kept constant. The fall of the lifting unit 122 with respect to the post 121 and the raise of the horizontal arm 141 with respect to the lifting unit 122 are simultaneously performed with the same displacement amount, which allow the horizontal arm 123 and the turning support 124 to fall with respect to the head P while the height of the head P fixed to the head fixing apparatus 142 is kept constant.

The X-ray imaging is performed in the state in which the head P that is the subject is fixed by the head fixing apparatus 142, and in the state in which the turning support 124 is stopped or rotated according to a desired imaging mode. Consequently, the X-ray projection image data necessary for the generation of the X-ray CT captured image (also simply referred to as an X-ray CT image or a CT image), and the panoramic captured image (also simply referred to as a panoramic image) can be obtained. For example, the X-ray imaging is performed while the turning support 124 is turned, which allows the X-ray CT imaging projection image data necessary for the generation of the X-ray CT image to be obtained. The X-ray CT imaging projection image data is projection image data for each direction obtained by irradiating the imaging region R with the X-ray cone beam from multiple directions, and can be collected in a form of frame image data. The X-ray imaging is performed to obtain the panoramic imaging projection image data while the turning support 124 is rotated in a certain range, and the panoramic image can be obtained by performing reconstruction image processing. The panoramic imaging projection image data is projection image data for each direction, which is obtained such that a chin region including a dental arch is irradiated with a narrow-gap X-ray beam extending in the z direction from multiple directions while the irradiation position is constantly changed, and each piece of the panoramic imaging projection image data can be collected in the form of frame image data. Additionally, the X-ray CT imaging apparatus 110 may also perform the X-ray imaging for obtaining the cephalogram image and a pseudo-oral image. For example, the head P is fixed to the cephalogram imaging head fixing apparatus 144 supported by the cephalogram head fixing apparatus suspending arm 143 extending horizontally from the post 121 while the turning support 124 is stopped, and the X-ray is emitted from the X-ray generator 126 to perform the X-ray imaging, which allows the cephalogram image to be obtained. A function of imaging the panoramic image and a function of imaging the cephalometric image are sometimes omitted.

The main body controller 150 is configured to be able to receive each instruction to the imaging main body 120, and is configured to be able to control each operation of the imaging main body 120. The main body controller 150 is fixed to the head fixing apparatus arm 141 extending in the horizontal direction from the post 121. The operation panel apparatus 158 is provided in the main body controller 150, the operation panel apparatus 158 displaying various kinds of information from the main body controller 150 while receiving various commands to the main body controller 150. The operation panel apparatus 158 includes a display 158a such as a liquid crystal display panel and a touch detector 158b, such as a touch panel, which is disposed on a display screen of the display 158a. The operation panel apparatus 158 is configured to be able to receive the operation performed on the X-ray CT imaging apparatus 110 by detecting a touch operation of a user on the display screen using the touch detector 158b. A push button may be provided near the operation panel apparatus 158. The display apparatus and the input apparatus that receives the operation of the user may separately be provided.

Each unit of the imaging main body 120 is accommodated in an X-ray protection chamber 146. A push button switch called a deadman switch that issues an instruction of the X-ray irradiation to the main body controller 150 is provided on the outside of a wall of the X-ray protection chamber 146.

The X-ray image processing apparatus 180 includes an information processing main body 182 constructed with a computer and the like, and is connected to the imaging main body 120 through a communication cable such that various pieces of data can be transmitted and received. However, the transmission and reception of the data may be performed by wireless communication between the imaging main body 120 and the X-ray image processing apparatus 180. The information processing main body 182 can perform various pieces of image processing based on the data transmitted from the imaging main body 120.

A display 188 constructed with a display apparatus such as a liquid crystal monitor and an operation unit 189 constructed with a keyboard or a mouse are connected to the X-ray image processing apparatus 180. The operator can issue various instruction to the information processing main body 182 by operating a pointer through the mouse on characters or images displayed on the display 188. The display 188 may be constructed with a touch panel.

Part or whole of the processing of the X-ray image processing apparatus 180 may be performed by the main body controller 150. Alternatively, part or whole of the processing of the main body controller 150 may be performed by the X-ray image processing apparatus 180.

<Block Diagram of X-Ray CT Imaging Apparatus>

Figure 5:
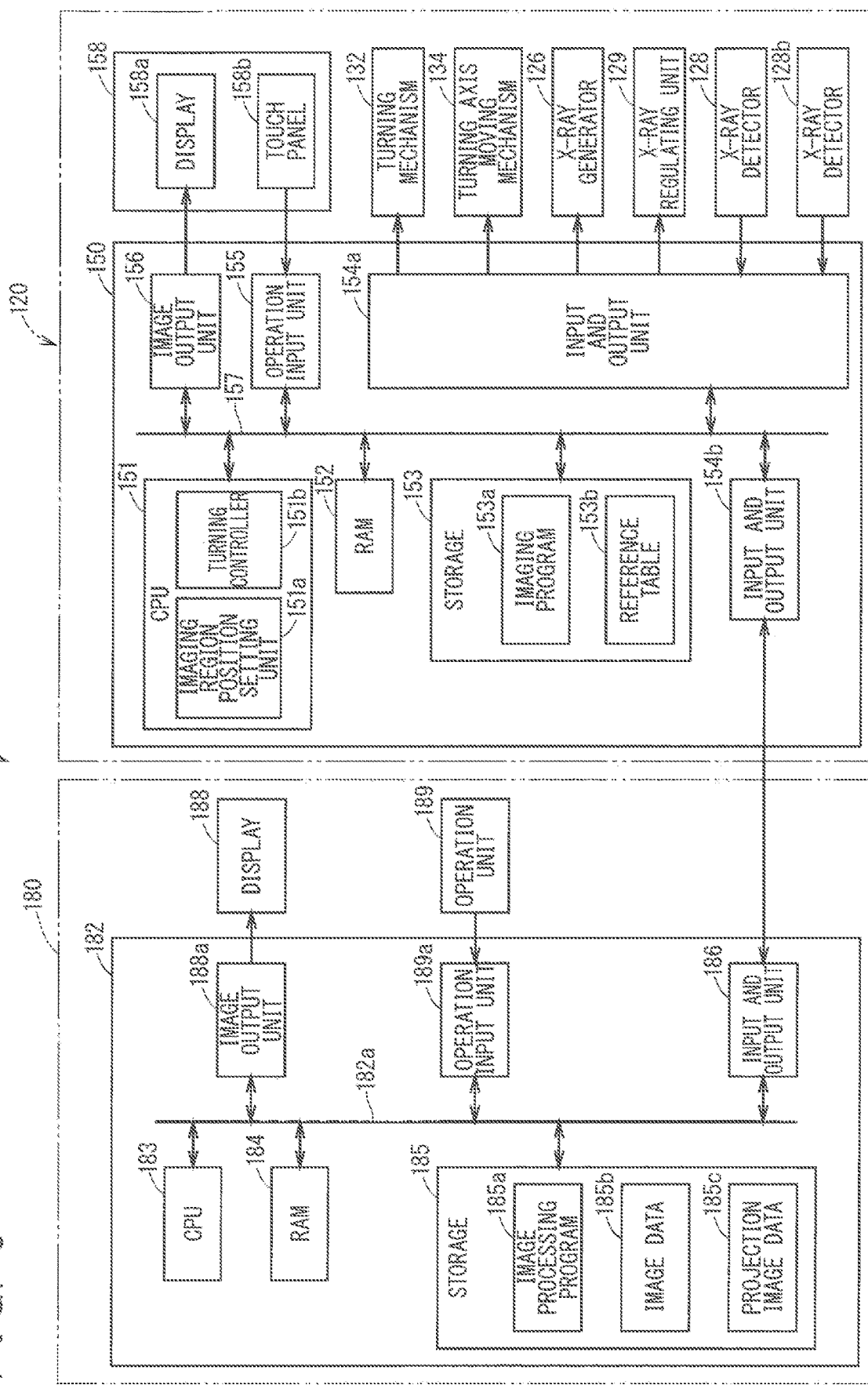
FIG. 5 is a block diagram illustrating an electric configuration of an X-ray CT imaging apparatus.

FIG. 5 is a block diagram illustrating an electric configuration of the X-ray CT imaging apparatus 110.

The main body controller 150 of the imaging main body 120 controls the X-ray imaging operation of the imaging main body 120, and is constructed with a computer in which a CPU (Central Processing Unit) 151 that is at least one processor, a RAM (Random Access Memory) 152, a storage 153, input and output units 154a, 154b, an operation input unit 155, and an image output unit 156 are interconnected to one another through a bus line 157. The storage 153 includes a nonvolatile storage device such as a flash memory or a hard disk. An imaging program 153a, which receives various instructions relating to the X-ray imaging and controls the X-ray imaging operation by controlling the turning mechanism 132, the turning axis moving mechanism 134, the X-ray generator 126, and the X-ray regulating unit 129 according to the instructions, is stored in the storage 153.

In the case of performing the X-ray CT imaging with a part located close to the front of the head P as the imaging region R, a reference table 153b including information indicating how the position of the turning axis X1 on the mechanism is controlled according to the turning of the turning support 124 by the turning mechanism 132 is stored in the storage 153. The position control information about the turning axis X1 on the mechanism is information controlling the position of the turning axis X1 on the mechanism in order to cause the X-ray generator 126 and the X-ray detector 128 to turn around the head P while locating the imaging region R therebetween, and in order to turn the X-ray detector 128 along the go-around orbit Q, which comes close to the imaging region R with respect to the front side of the head P and moves away from the imaging region R with respect to the rear side, by changing the distance between the X-ray detector 128 and the center A of the imaging region R, and for example in information on the coordinates. The movement control information is theoretically and experimentally decided in consideration of the position of the imaging region R (such as the position of the front tooth) in the head P, the shape and size of a standard head P (for example, standard adult), and the distance between the X-ray generator 126 or the X-ray detector 128 and the turning axis X1 on the mechanism. For example, in consideration of the maximum distance between a surface of the head P and the center A of the imaging region R, the go-around orbit Q of the X-ray detector 128 is decided such that the X-ray detector 128 does not contact with the head surface.

An example of the position control information about the turning axis X1 on the mechanism will be described later as an example of the moving orbit of the turning axis X1 together with examples of the go-around orbits of the X-ray generator 126 and the X-ray detector 128.

The RAM 152 serves as a work area when the CPU 151 performs predetermined processing. The input and output unit 154a is connected to a motor of the turning mechanism 132 that turns the turning support 124 of the imaging main body 120, a motor of the turning axis moving mechanism 134 that moves the turning support 124, the X-ray generator 126, X-ray detectors 128, 128b, and the X-ray regulating unit 129, and the input and output unit 154b is communicably connected to the X-ray image processing apparatus 180. The operation input unit 155 is connected to the touch detector 158b of the operation panel apparatus 158, and the image output unit 156 is connected to the display 158a of the operation panel apparatus 158.

In the main body controller 150, the CPU 151 performs calculation processing according to a procedure described in the imaging program 153a and the instruction received through the touch detector 158b, thereby performing a function as the turning controller 151b that controls the turning mechanism 132 and the turning axis moving mechanism 134 in performing the X-ray imaging such as the X-ray CT imaging. Similarly, the CPU 151 performs a function as an imaging region setting unit 151a that receives setting of the position of the imaging region R (local imaging region R) with respect to a part (local region) of the head P that is the subject. The CPU 151 controls the turning mechanism 132 and the turning axis moving mechanism 134 to turn the X-ray generator 126 and the X-ray detector 128 around the head P, and can obtain a detection result of the X-ray detected by the X-ray detectors 128, 128b.

When the X-ray CT imaging apparatus 110 is used for dentistry, for example, the dental arch or the chin region including the dental arch is set to a target region of the X-ray CT imaging. The chin region may include a temporomandibular joint region. As seen from the Z direction, it is conceivable that the imaging region R is set to the following region. For example, it is assumed that a whole head region or a head local imaging region (which can also be referred to as a head local region) that is a part of the head. Hereinafter, it is conceivable that the whole dental arch region, the whole chin region, a dental arch local imaging region (which can also be referred to as a dental arch local region) that is a partial region of the dental arch, and a chin local imaging region (which can also be referred to as a chin local region) that is a partial region of the chin region is set to an example of the head local imaging region.

In particular, in the case that the X-ray CT imaging is performed with a part located close to the front of the head P as the imaging region R, using the turning mechanism 132 and the turning axis moving mechanism 134, the turning controller 151b causes the X-ray generator 126 and the X-ray detector 128 to turn around the head P while locating the imaging region R therebetween, and causes the X-ray detector 128 to turn along the go-around orbit Q, in which the X-ray detector 128 comes close to the imaging region R with respect to the front side of the head P and moves away from the imaging region R with respect to the rear side, by changing the distance between the X-ray detector 128 and the center A of the imaging region R. An example of the go-around orbit Q and specific control examples of the turning mechanism 132 and the turning axis moving mechanism 134 for realizing the go-around orbit Q will be described later.

The imaging program 153a and the reference table 153b are previously stored in the storage 153. Alternatively, the imaging program 153a and the reference table 153b may be provided to the existing X-ray CT imaging apparatus or the information processing main body that controls the X-ray CT imaging apparatus in the form of being recorded on a recording medium such as a CD-ROM, a DVD-ROM, or an external flash memory, or by download from an external server through a network.

The X-ray image processing apparatus 180 generates X-ray image data 185b based on the imaging data from the imaging main body 120. The information processing main unit 182 is constructed with a computer in which a CPU 183 that is at least one processor, a RAM 184, a storage 185, an input and output unit 186, an operation input unit 189a, and an image output unit 188a are mutually connected through a bus line 182a. The storage 185 is constructed with a nonvolatile storage device such as a flash memory or a hard disk drive, and an image processing program 185a with which the information processing main body 182 generates the X-ray image data 185b based on the imaging data from the imaging main body 120 and X-ray image data 185b are stored in the storage 185. Management data in which the X-ray image data 185b is correlated with specific information about the head P (specific information about a patient) may be stored in the storage 185. The X-ray image processing device 180 receives data relating to an imaging condition from the main body controller 150, and may store the data relating to an imaging condition in the storage 185 while correlating the data relating to an imaging condition with the generated X-ray image data 185b. The RAM 184 serves as a work area when the CPU 183 performs predetermined processing. The input and output unit 186 is connected to the imaging main body 120, and the X-ray imaging data obtained by the imaging main body 120 is input through the input and output unit 186. The operation input unit 189a is connected to the operation unit 189, and the image output unit 188b is connected to the display 188.

In the storage 185, the imaging data from the imaging main body 120 may be stored as pre-reconstruction projection image data 185c. The projection image data 185c may be completely unprocessed raw data or preprocessed data processed to some extent for reconstruction. For example, the projection image data 185c is the above frame image data.

The management data with which the specific information about the head P (the specific information about the patient) and/or the data relating to the imaging condition may be stored in the storage 185 while correlated with the image data 185b or the projection image data 185c.

In the information processing main body 182, the CPU 183 performs the calculation processing according to the image processing program 185a, thereby performing the processing as the image processor that generates the desired X-ray image data based on the X-ray imaging data obtained by the imaging main body 120. That is, data such as the CT image, the panoramic image, and the cephalogram image is generated according to an instruction received through the main body controller 150. The storage 185 stores the generated X-ray image data 185b.

A part or whole of the function implemented in each of the above units may be implemented in a hardware manner with a dedicated logic circuit or the like. A part or whole of the function implemented in each of the above units may be processed by a single processor in an integrated manner, or appropriately processed by a plurality of processors in a distributed manner.

<Setting of Position of Imaging Region R and Turning Process During Imaging>

Figure 6:
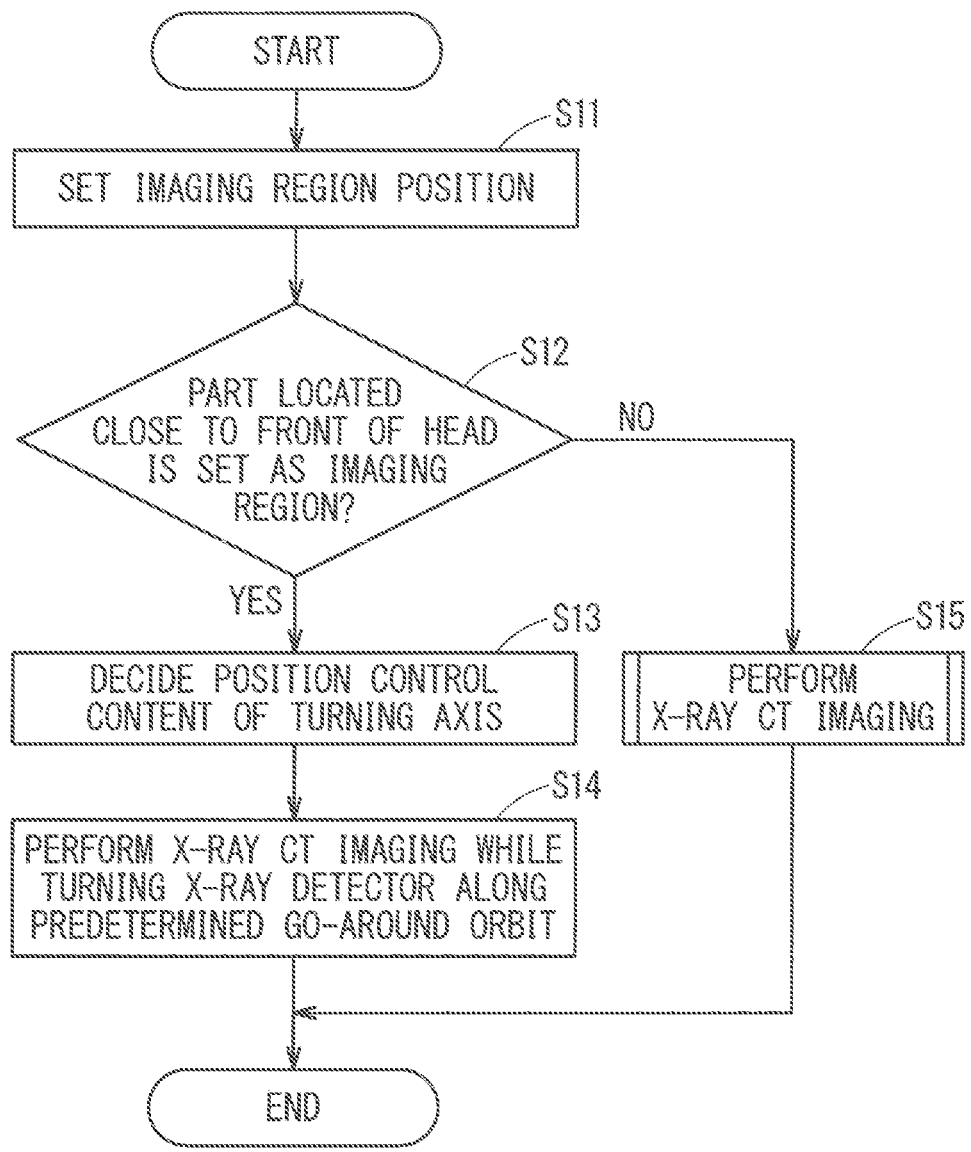
FIG. 6 is a flowchart illustrating a processing example by an imaging program.

With reference to the flowchart in FIG. 6, the control performed by the turning controller 151b based on the imaging program 153a will be described centered on the setting of the position of the imaging region R and the turning processing during imaging.

When the performance of the CT imaging is set, the setting operation of the position of the imaging region R is received in step S11.

Figure 7:
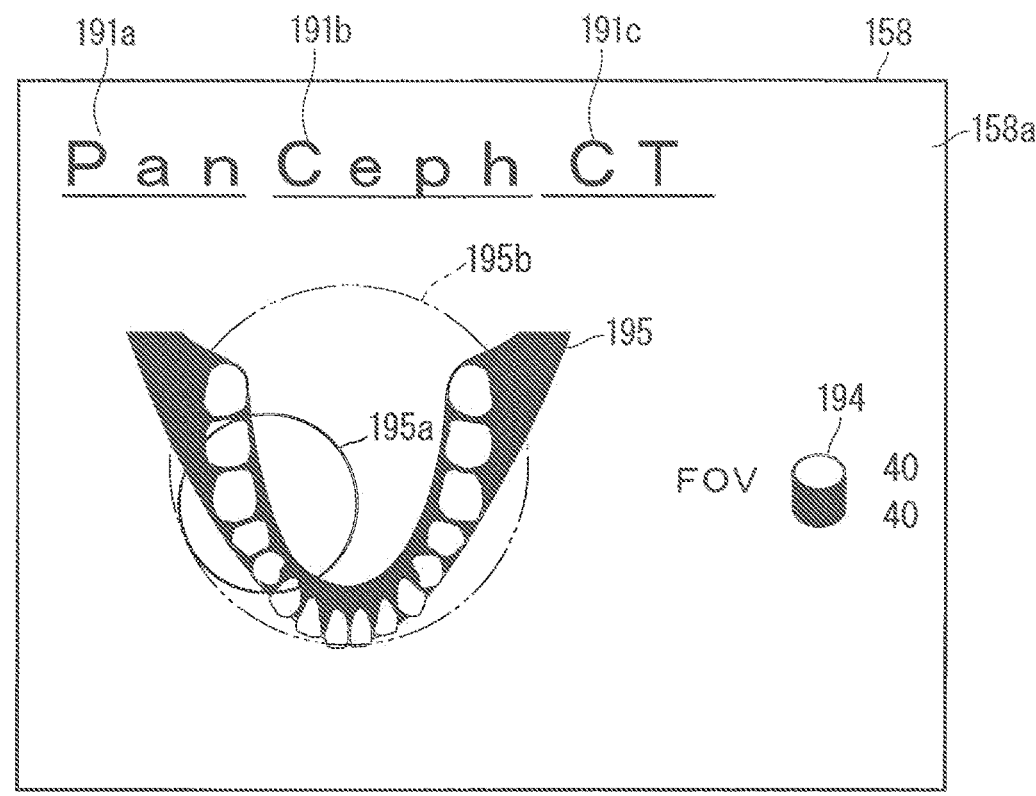
FIG. 7 is a view illustrating a display example in an operation panel apparatus.

An example of receiving the setting operation of the position of the imaging region R will be described below. FIG. 7 is a view illustrating a display example in the operation panel device 158. A panorama selection image 191a (see characters "Pan") for selecting the panoramic imaging mode, a cephalogram selection image 191b (see characters "Ceph") for selecting the cephalogram imaging mode, and a CT selection image 191c (see characters "CT") for selecting the CT imaging mode are displayed on the display 158a of the operation panel apparatus 158 as a images for selecting imaging mode. "Pan", "Ceph", and "CT" are characters, but are displayed in the form that they can visually be recognized as characters, and are a character-shapes image. "Pan", "Ceph", and "CT" may be an image that symbolically represents each imaging without taking the shape of letters, or both may be used in combination. In FIG. 7, the CT imaging mode is selected using the CT selection image 191c. On the display 158a, an imaging region setting image 194 is displayed as an image used to set the imaging condition. At this point, the imaging region setting image 194 is displayed on the right of the display 158a. An illustration image 195 is displayed on the display 158a. The illustration image 195 is displayed on the lower side of the panorama selection image 191a, the cephalogram selection image 191b, and the CT selection image 191c in the display 158a. The illustration image 195 is an image for representing the imaging region R, and the dental arch is displayed as the illustration image.

When the imaging target is set to a dental region, the imaging target region may be set to the dental arch, and set to the chin region including the dental arch. The chin region may include the temporomandibular joint region.

When being three-dimensionally observed, the imaging region R may be set as a columnar in which the center axis is the axis along the vertical direction of the head P or spherical region. In this case, in the illustration image, the imaging region R is represented as the circular region R.

On the display 158a, the touch detector 158b is provided as a two-dimensional position detector that detects a touch position with respect to the display area.

When the operator touches any one of the panorama selection image 191a, the cephalogram selection image 191b, and the CT selection image 191c, the touch operation is detected by the touch detector 158b. Consequently, the main body controller 150 receives whether to perform the panoramic imaging, the cephalogram imaging, or the X-ray CT imaging.

Figure 8:
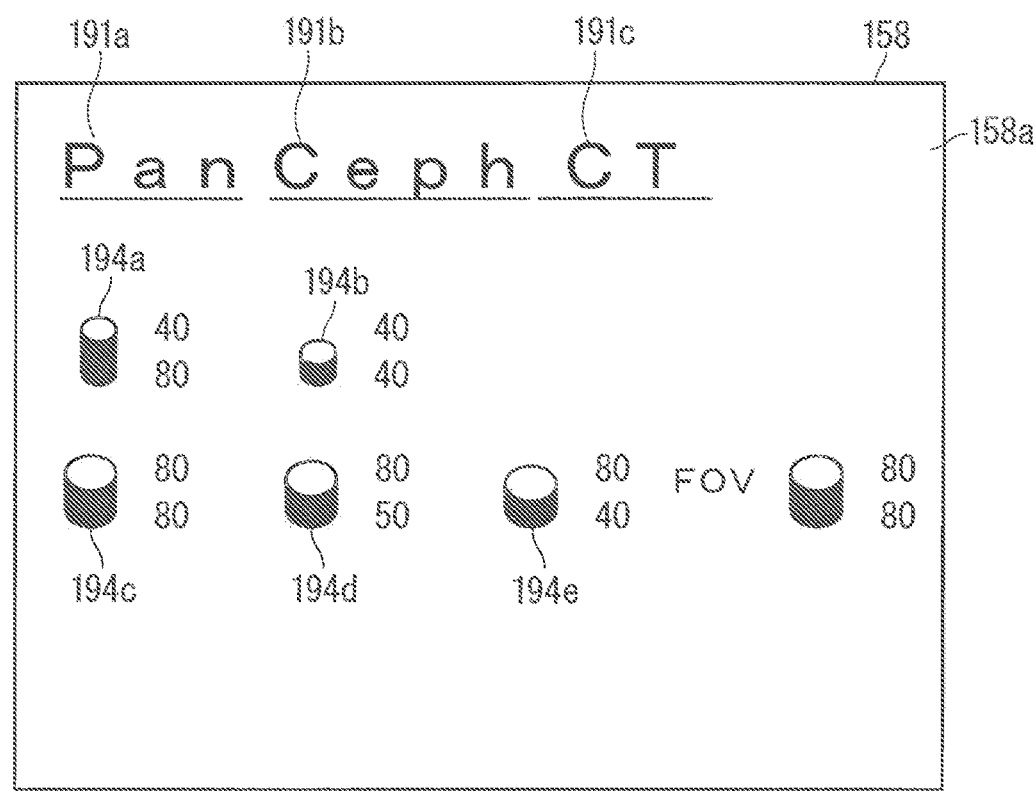
FIG. 8 is a view illustrating a display example in the operation panel apparatus.

As illustrated in FIG. 8, when the operator touches the imaging region setting image 194, a plurality of imaging region selection images 194a, 194b, 194c, 194d, 194e corresponding to the imaging region setting image 194 are displayed according to the touch operation. The plurality of imaging region selection images 194a, 194b, 194c, 194d, 194e indicate regions in which sizes (a diameter and a height) are different from one another. When the user selectively touches any one of the plurality of imaging region selection images 194a, 194b, 194c, 194d, 194e, the setting operation of the imaging region is received.

In the example in FIG. 8, the imaging region selection images 194a, 194b are images used to select the imaging region R having a diameter of 40 mm. The imaging region selection image 194a indicates that the imaging region R has the height of 80 mm, and the imaging region selection image 194b indicates that the imaging region R has the height of 40 mm. That is, in each imaging region selection image, the diameter is displayed in the upper stage, the height is displayed in the lower stage, and the numerical value indicates magnitude in units of millimeter. Regardless of the height of the imaging region R, the fact that the imaging region R has the diameter of 40 mm indicates that a part of the dental arch is designated as the region. Thus, it can be said that the imaging region selection images 194a, 194b are images used to receive the performance of the X-ray CT imaging while a part of the dental arch is set to the target.

The imaging region selection images 194c, 194d, 194e are images used to select the imaging region R having the diameter of 80 mm. The imaging region selection images 194c, 194d, 194e indicate that the heights of the imaging region R are 80 mm, 50 mm, and 40 mm, respectively. Regardless of the height of the imaging region R, the fact that the imaging region R has the diameter of 80 mm indicates that the whole region of the dental arch viewed from the axial direction of the body axis is designated as the region. Thus, it can be said that the imaging region selection images 194b, 194c, 194d are images used to receive the performance of the X-ray CT imaging while the whole dental arch is set to the target.

For example, both the upper and lower chin regions are set to the target for the height is 80 mm, one of the upper and lower chin regions in the case that the head P is located such that a Frankfurt plane becomes horizontal is set to the target for the height of 50 mm, and one of the upper and lower chin regions in the case that the head P is located such that a Camper's plane becomes horizontal is set to the target for the height of 40 mm.

Assuming that the imaging region selection image 194b is selected, the imaging region having the diameter of 40 mm and the height of 40 mm is selected as illustrated at the substantial center in the vertical direction on the right side in FIG. 7.

Both the case of designating a part of the dental arch (in the above example, the imaging region R having the diameter of 40 mm) and the case of designating the whole region of the dental arch (in the above example, the imaging region R having the diameter of 80 mm) are examples of the case that a part of the head P is set to the imaging region R when viewed from the whole head P.

Referring to FIG. 7, an imaging region image 195a is displayed while superimposed on the illustration image 195. (In the case of selecting the imaging region R having the diameter of 80 mm, the imaging region image 195b is displayed while superimposed on in the illustration image 195) A circle having the size set through the imaging region setting images 194 is displayed as the imaging region images 195a, 195b. The imaging region image 195a is an image that is displayed in the case that the imaging region R where a part of the dental arch is set to the target is selected, and the imaging region image 195b is an image that is displayed in the case that the imaging region R where the whole dental arch is set to the target is selected. For example, in the example of FIG. 7, in the case that the imaging region image 195a is displayed by selecting the imaging region having the diameter of 40 mm and the height of 40 mm, the operator touches the desired position of the illustration image 195 to move the imaging region image 195a to the position where a part of the dental arch is designated. Consequently, the imaging region R can be designated at any position of the dental arch (for example, a front tooth region, a right molar region, a left molar region). The imaging region image 195a may be focused with a pointer, and moved to the desired position like drag and drop so as to be able to designate the region, or the imaging region image 195a may be focused with a pointer, and moved separately with a moving key. The illustration image 195 may similarly be moved with respect to the stationary imaging region image 195a on the screen so as to designate the region.

When the designation of the imaging region R is received, the turning support 124 is moved to the position where the turning support 124 can turn about the center A of the imaging region R by the driving of the turning axis moving mechanism 134, and an angle around the turning axis X1 of the turning support 124 is decided for the start of the imaging by the turning mechanism 132.

The case that the imaging region R is selected with the front tooth region that is a part of the dental arch as the target is an example of the case that the position of a part located close to the front of the head P is set as the imaging region R. In the following example, the case that the X-ray CT imaging is performed with the front tooth region as the imaging target will be mainly described.

However, the imaging region R where the whole dental arch is set to the target can also be regarded as an example of the case that the position of a part located close to the front of the head P is set as the imaging region R. In this case, the control may be performed in order to turn the X-ray detector 128 in the go-around orbit Q as described below.

The example in which the imaging mode is designated or the imaging region R is designated using the touch panel is described above. Alternatively, but various settings may be received through a switch (push button) that physically receives an operation. The movement operation is not limited to the touch operation, but may be performed by a key or the like.

As described above, in step S11, the imaging region setting unit 151a receives a setting operation of the position of the imaging region R with respect to a part located close to the front of the head P through the operation panel apparatus 158. At this point, the imaging region setting unit 151a receives the setting of the position of the imaging region R by receiving the selection of any one of the imaging region selection images 194a, 194b and the position setting of the illustration image 195 using the imaging region image 195a through the operation panel apparatus 158.

Whether or not a part located close to the front of the head P is set as the imaging region R is determined in step S12. In the above example, when the front tooth region is set as the imaging region R, an affirmative determination is made, and the processing proceeds to step S13. When the right or left molar region is set as the imaging region R, a negative determination is made, and the processing proceeds to step S15. The X-ray CT imaging is performed on the molar region by known control in step S15, and the processing is ended. An example of the turning control of the applicable X-ray detector 128 in the case that the right or left molar region is set as the imaging region R will be described later in a modification.

For example, whether or not the imaging region R is the front tooth region based on the set imaging region R is determined based on whether or not the coordinate of the center A of the set imaging region R belongs to the previously-set molar region in the case that the region of a part of the dental arch is designated (in the above example, the imaging region R having the diameter of 40 mm).

In step S13, a position control content of the turning axis X1 is decided by referring to the reference table 153b. The position control content of the turning axis X1 indicates how the turning axis X1 is moved by the turning axis moving mechanism 134 during the turning of the turning support 124 using the turning mechanism 132.

In step S14, based on the decided position control content of the turning axis X1, the X-ray detector 128 is turned along the predetermined go-around orbit Q to perform the X-ray CT imaging. That is, using the turning mechanism 132 and the turning axis moving mechanism 134, the X-ray generator 126 and the X-ray detector 128 are turned around the head P while the imaging region R is located between the X-ray generator 126 and the X-ray detector 128. At this point, by changing the distance between the X-ray detector 128 and the center A of the imaging region R, the X-ray detector 128 is turned along the go-around orbit Q, which comes close to the imaging region R with respect to the front side of the head P and moves away from the imaging region R with respect to the rear side. In other words, the X-ray generator 126 and the X-ray detector 128 are turned around the head P while changing an enlargement ratio of the imaging region R such that the enlargement ratio of the imaging region R is decreased with respect to the front side of the head P (the timing at which the X-ray detector 128 is located close to the front of the head P while the X-ray generator 126 is located close to the rear of the head P), and such that the enlargement ratio of the imaging region R is increased with respect to the rear side (the timing at which the X-ray detector 128 is located close to the rear of the head P while the X-ray generator 126 is located close to the front of the head P).

For example, assuming that DG is the distance between the X-ray generator 126 and the center A of the imaging region R and that DD is the distance between the X-ray detector 128 and the center A of the imaging region R, the enlargement ratio can be calculated by (enlargement ratio) =(DG+DD)/DG.

An example of this turning operation will be described in more detail with reference to FIGS. 9 and 10. The go-around orbit and moving orbit in FIGS. 9 and 10 and the subsequent figures are sometimes exaggerated. In the go-around orbit, the position in the center in a width direction of the detection surface of the X-ray detector 128 is considered as a reference.

In the initial state before the start of the X-ray CT imaging, the head P is fixed to a fixed position at a fixed posture by the head fixing apparatus 142. In the following description, the terms of the front and the rear are used based on the front and rear of the head P fixed by the head fixing apparatus 142. It is assumed that the X-ray generator 126 and the X-ray detector 128, which are supported by the turning support portion 124, are disposed while the head P is provided therebetween. In the initial state, the turning axis X1 on the mechanism is located on the center A of the imaging region R, the X-ray generator 126 is disposed on the right with respect to the head P, and the X-ray detector 128 is disposed on the left with respect to the head P. From this state, it is assumed that the X-ray generator 126 and the X-ray detector 128 turn clockwise. It is assumed that the turning axis X1 is located closer to the X-ray detector 128 than the X-ray generator 126. It is assumed that L1 is the distance between the turning axis X1 and the X-ray generator 126, and that L2 is the distance between the turning axis X1 and the X-ray detector 128.

A demand, in which the X-ray detector 128 is brought as close to the imaging region R as possible in order that the enlargement ratio becomes as small as possible to make the projection image clear while the movement amount of the turning axis X1 on the mechanism is suppressed as compact as possible during the X-ray imaging, is met as an example of the effect of the configuration in which the turning axis X1 on the mechanism is provided at a position closer to the X-ray detector 128 than the center position between the X-ray generator 126 and the X-ray detector 128.

The positions of the X-ray generator 126 and the X-ray detector 128 in the initial state are not limited to the above example. For example, the X-ray detector 128 may be located in front for a fan angle of the X-ray beam (on the assumption of the right turning, it is located in front on the counterclockwise turning side) with respect to the immediate left side of the head P. The fan angle of the X-ray beam is a spread angle of the irradiation of the X-ray beam (see an angle β in FIG. 9). In the initial state, the X-ray detector 128 may be disposed at any position on the front side, the right side, and the rear side of the head P and therebetween. The X-ray generator 126 and the X-ray detector 128 may turn counterclockwise.

In order to realize the go-around orbit Q of the X-ray detector 128, in the second preferred embodiment, in synchronization with the turning of the turning support 124 about the turning axis X1 using the turning mechanism 132, the turning axis moving mechanism 134 moves the turning axis X1 to cause the turning support 124 to perform the combined movement, thereby controlling the go-around orbit Q of the X-ray detector 128 with respect to the head P.

As a result, the X-ray generator 126 and the X-ray detector 128 turn around the head P while the imaging region R is located therebetween. At this point, the distance between the X-ray detector 128 and the center A of the imaging region R is changed. As a result, the X-ray detector 128 turns along the go-around orbit Q, which comes close to the imaging region R with respect to the front side of the head P and moves away from the imaging region R with respect to the rear side.

The go-around orbit Q may be an orbit that does not include a concave portion toward the imaging region R. The go-around orbit Q may be an orbit in which a curve protruding outward is continuous in the whole circumference of the head P.

The go-around orbit Q may be a circular or elliptical orbit, which comes close to the imaging region R with respect to the front side of the head P and moves away from the imaging region R with respect to the rear side.

In the case that the imaging region R is the front tooth region, the X-ray detector 128 may come closest to the imaging region R at the front of the head P in the go-around orbit Q.

The go-around orbit Q includes an equidistant moving orbit Q1 in which the X-ray detector 128 moves while maintaining an equidistance from the center A of the imaging region R when the X-ray detector 128 passes through the front side of the head P, and the remaining orbit Q2 of the equidistant moving orbit Q1 in the go-around orbit Q may be a distance changing moving orbit Q2 in which the X-ray detector 128 moves while changing the distance with respect to the center A of the imaging region R. A front side half of the go-around orbit Q is the equidistant moving orbit Q1, and a back side half is the distance changing moving orbit Q2. The go-around orbit Q is not necessarily equally divided into the front and the rear by the equidistant moving orbit Q1 and the distance changing moving orbit Q2. The equidistant moving orbit Q1 may occupy a smaller portion or a larger portion than the distance changing moving orbit Q2. Preferably, the equidistant moving orbit Q1 spreads to the left and right equal ranges with the front face of the head P as the center.

The turning axis X1 may be changed in the direction parallel to the direction in which the imaging region R is biased with respect to the center of the head P in order to realize the go-around orbit Q of the X-ray detector 128 by the movement of the turning axis X1.

That is, the go-around orbit Q includes a first orbit that comes close to the imaging region R on the side on which the imaging region R is biased in the head P and a second orbit that moves away from the imaging region R on the side opposite to the side on which the imaging region R is biased in the head P. Assuming that the imaging region R is the front tooth region, the side on which the imaging region R is biased in the head P is the front side with respect to the head P. For this reason, the first orbit is the front-side orbit in the go-around orbit Q (because it is the same as the equidistant moving orbit Q1, hereinafter the same symbol Q1 is given). Similarly, the side opposite to the side on which the imaging region R is biased in the head P is the rear side with respect to the head P. For this reason, the second orbit is the rear-side orbit in the go-around orbit Q (because it is the same as the distance changing moving orbit Q2, hereinafter the same symbol Q2 is given).

The turning axis moving mechanism 134 changes the position of the turning axis X1 on the mechanism in each of the first orbit Q1 and the second orbit Q2 in the direction (the front-rear direction of the head P) parallel to the front-side direction that is the direction in which the imaging region R is biased with respect to the center of the head P, thereby forming the go-around orbit Q. The change of the turning axis X1 to the direction parallel to the front-side direction (the front-rear direction of the head P) that is the direction in which the imaging region R is biased with respect to the center of the head P means the change to the direction including a component of the parallel direction (the front-rear direction of the head P). Thus, the position of the turning axis X1 in the go-around orbit Q may be moved not only in the parallel direction (the front-rear direction of the head P) but also in the direction intersecting the parallel direction. A curvature radius of the first orbit Q1 may be smaller than a curvature radius of the second orbit Q2.

Consequently, for example, the position of the turning axis X1 can be changed in the front-back direction of the head P in the states in which the X-ray detector 128 is located on the front side of the head P and on the rear side of the head P. More specifically, the position of the turning axis X1 when the X-ray detector 128 is located on the front side of the head P is disposed at a position closer to the front in the front-rear direction of the head P than the position of the turning axis X1 when the X-ray detector 128 is located on the rear side of the head P. Consequently, the X-ray detector 128 can be brought close to the imaging region R when located on the front side of the head P. The X-ray detector 128 can be moved away from the imaging region R when located on the rear side of the head P.

More specifically, as the movement control content of the turning axis X1, in a period in which the X-ray detector 128 turns, the turning axis X1 on the mechanism is located in the center of the imaging region R in at least a part of the period in which the X-ray detector 128 passes through the front side of the head P, and the turning axis X1 on the mechanism moves in other periods.

Figure 9:
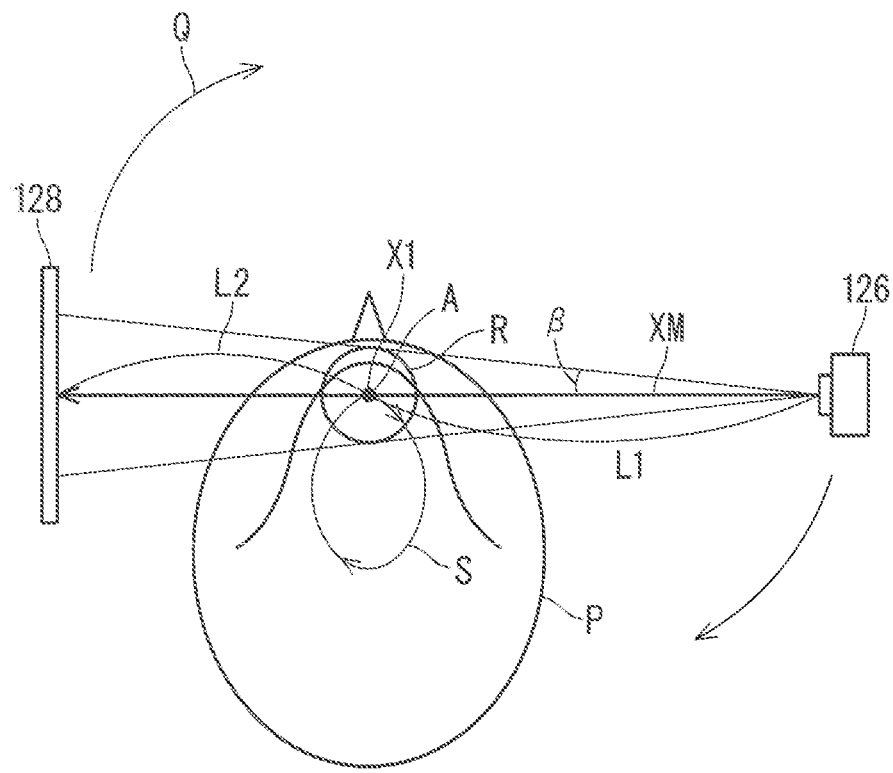
FIG. 9 is an explanatory view illustrating a moving orbit example of a turning axis.
Figure 10:
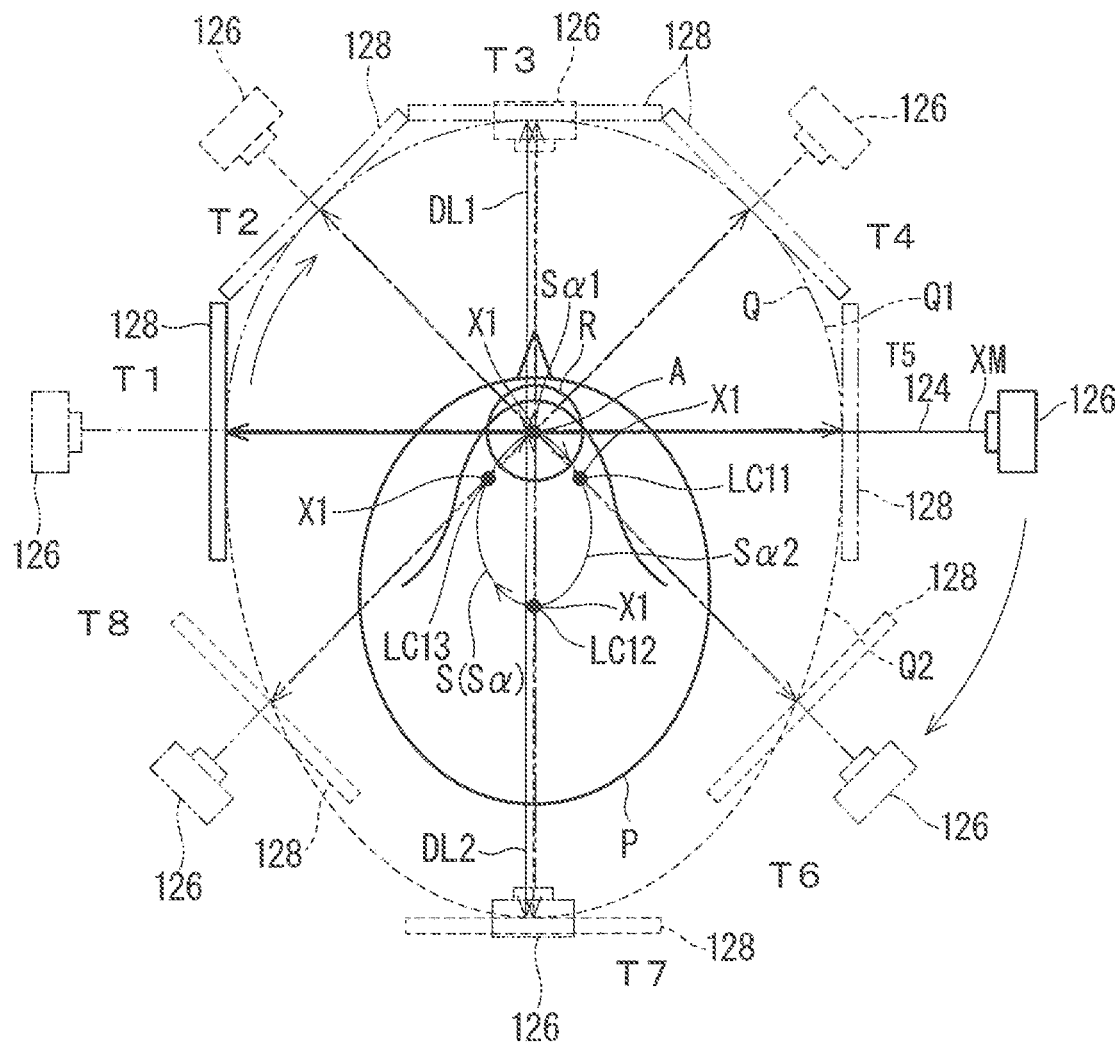
FIG. 10 is an explanatory view illustrating a go-around orbit example of an X-ray detector.
Figure 10:
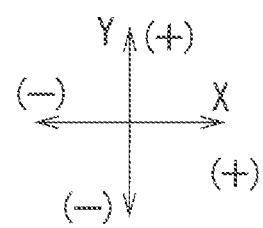

An axis orbit S of the turning axis X1 included in the movement control content of the turning axis X1 is illustrated in FIGS. 9 and 10. The axis orbit S is an orbit that changes the distance between the X-ray detector 128 and the center A of the imaging region R when the turning mechanism 132 turns the turning support 124. Sometimes the axis orbit S is simply referred to as an orbit S. As an example, because the X-ray detector 128, the turning axis X1, and the center A of the imaging region R are disposed on one straight line, the distance between the turning axis X1 and the center A of the imaging region R is also changed in order to change the distance between the X-ray detector 128 and the center A of the imaging region R. For this reason, the axis orbit S may be regarded as an axis distance changing orbit S that changes the distance between the turning axis X1 and the center A of the imaging region R when the turning mechanism 132 turns the turning support 124. Because the axis orbit S is an orbit that displaces the turning axis X1, the axis orbit S may be an axis displacing orbit. In addition, the distance between the turning axis X1 and the center A of the imaging region R is considered as the axis distance.

At this point, the axis distance changing orbit S draws a long elliptic shape along the front-rear direction of the head P. The axis distance changing orbit S needs not to be an ellipse in a mathematically strict meaning. In the axis distance changing orbit S of FIGS. 9 and 10, a portion located close to the front of the head P in the front-rear direction has an elongated shape as compared with a part located closer to the rear of the head P in the front-rear direction. In the axis distance changing orbit S, a portion located closer to the front of the head P is located in the center A of the imaging region R, and other portions spreads rearward from the center A of the imaging region R. The axis distance changing orbit S may be an orbit in which a curvature is changed. In FIG. 10, the X-ray detector 128 (with the X-ray generator 126 and the turning support 124) and the orbit Q1, which pass through the front of the head P are drawn by a two-dot chain line, and the X-ray detector 128 (with the X-ray generator 126 and the turning support 124) and the orbit Q1, which pass through the rear of the head P are drawn by a broken line. Also in the following figures, they may be drawn in the same way.

As the movement control content of the turning axis X1, when the turning mechanism 132 turns the turning support 124, the turning axis moving mechanism 134 locates the turning axis X1 to the center A of the imaging region R in at least a part of the period in which the X-ray detector 128 passes through the front of the head P, in this case, in the period in which the X-ray detector 128 passes through the first orbit Q1 that is the front side half with respect to the head P. In this period, the X-ray generator 126 and the X-ray detector 128 turn about the center A of the imaging region R. At this point, the X-ray detector 128 has the turning diameter of L2, and the X-ray generator 126 has the turning diameter of L1. As a result, the equidistant moving orbit Q1 in which the X-ray detector 128 moves while keeping the equidistance L2 with respect to the center A of the imaging region R (keeping the enlargement ratio of the imaging region R constant) is formed while the X-ray detector 128 passes through the front of the head P.

As the movement control content of the turning axis X1, when the turning mechanism 132 moves the turning support 124, the turning axis moving mechanism 134 moves the turning axis X1 on the mechanism along the axis distance changing orbit S in other periods, in this case, in the period in which the X-ray detector 128 passes through the second orbit Q2 that is the back side half with respect to the head P. In this case, the turning axis X1 turns clockwise along the axis distance changing orbit S. That is, when the X-ray detector 128 turns on the rear right side of the head P, the turning axis X1 is turned on the rear right side with respect to the center of the imaging region R, whereby the X-ray detector 128 moves away from the imaging region R. When the X-ray detector 128 turns on the rear left side of the head P, the turning axis X1 is turned on the rear left side with respect to the center of the imaging region R, whereby the X-ray detector 128 moves away from the imaging region R. The enlargement ratio of the imaging region R becomes larger than the enlargement ratio when the X-ray detector 128 moves in the equidistant moving orbit Q1, and the enlargement ratio becomes the maximum particularly when the X-ray detector 128 passes through just behind the head P.

When the X-ray detector 128 moves in the go-around orbit Q, a moving speed (position) of the turning axis X1 in the axis distance changing orbit S is controlled such that the X-ray detector 126 and the X-ray detector 128 turn while the state in which a center line XM of the X-ray emitted from the X-ray generator 126 passes through the center A of the imaging region R is maintained.

In the example of FIG. 10, the turning axis X1 on the mechanism is located in the center A of the imaging region R in the timing at which the X-ray detector 128 turns from the −X side to the +X side through the +Y side (see T1 to T5). In the timing at which the X-ray detector 128 is located closer to the combined direction of the component in the +X direction and the component in the −Y direction (see T6), the turning axis X1 on the mechanism is located at a position LC11 closer to the combined direction of the component in the +X direction and the component in the −Y direction with respect to the center A of the imaging region R. In the timing at which the X-ray detector 128 is located on the −Y direction side (see T7), the turning axis X1 on the mechanism is located at a position LC12 closer to the −Y direction with respect to the center A of the imaging region R. In the timing at which the X-ray detector 128 is located closer to the combined direction of the component in the −X direction and the component in the −Y direction (see T8), the turning axis X1 on the mechanism is located at a position LC13 closer to the combined direction of the component in the X direction and the component in the −Y direction with respect to the center A of the imaging region R.

The turning axis X1 on the mechanism is located in the center A of the imaging region R in the period (T1 to T5) in which the X-ray detector 128 turns from the −X side to the +X side through the +Y side. In this period, an amount of change in the distance between the turning axis X1 on the mechanism and the center A of the imaging region R is zero. Assuming that the amount of change in the distance between the turning axis X1 on the mechanism and the center A of the imaging region R is set to zero in the timings of T1 to T5, and that the amount is set to a value exceeding zero in other timings, the axis distance changing orbit S can be regarded as an orbit that changes the amount of change in the distance between the turning axis X1 on the mechanism and the center A of the imaging region R when viewed as a whole.

The position or the movement path of the turning axis X1 on the mechanism in the period in which the X-ray detector 128 turns from the −X side to the +X side through the +Y side is set to an axis orbit Sα1 irrespective of the movement of the turning axis X1, and the position or movement path of the turning axis X1 on the mechanism in the period in which the X-ray detector 128 turns from the +X side to the −X side through the −Y side is set to an axis orbit Sα2 irrespective of the movement of the turning axis X1. In the axis orbit Sα2, because the distance between the turning axis X1 and the center of the imaging region R changes, the axis orbit Sα2 can be considered to be an axis distance changing orbit Sα2. The axis distance changing orbit Sa constructed with the axis orbit Sα1 and the axis orbit Sα2 is the axis distance changing orbit S in FIG. 10. A portion, such as the axis orbit Sα1, in which the turning axis X1 remains at the same position while the X-ray generator 126 and the X-ray detector 128 turn around the center of the imaging region R with respect to the axis orbit S, may be referred to as an axis retention region. A portion, such as the axial orbit Sα2, in which the axis distance varies except for the axis retention region in the axis distance changing orbit S, may be referred to as an axis distance changing region. In the second preferred embodiment of FIG. 10, the axis orbit S is constructed with the axis retention region and the axis distance changing region.

When the X-ray detector 128 moves from the position T1 to T5 through T2, T3, T4, the turning axis X1 is located in the center A of the imaging region R. The X-ray detector 128 moves along a semicircular arcuate orbit Q1 with the center A of the imaging region R as the center, and a turning diameter DL1 of the X-ray detector 128 is the same as the distance L2 between the turning axis X1 and the X-ray detector 128. When the X-ray detector 128 moves from the position T5 to the position T1 through the positions T6, T7, T8, the turning axis X1 moves along the orbit S while changing the distance to the center A of the imaging region R by zero or more (the change amount is zero at positions T5, T1, and the change amount exceeds zero in other timings). The axis distance changing orbit S has an elliptic shape long in the front-rear direction of the head. For this reason, at the positions T6 to T8, the turning axis X1 is located at the positions LC11, LC12, LC13 that are away from the center A of the imaging region R in the −Y direction. Meanwhile, at the position LC12, the turning axis X1 moves maximally away from the center A of the imaging region R. In this period, the X-ray detector 128 is separated from the center A of the imaging region R by the distance in which the distance between the turning axis X1 and the center A of the imaging region R is added to the distance L2 between the turning axis X1 and the X-ray detector 128. In particular, when the turning axis X1 is located at the position LC12, the X-ray detector 128 is separated from the center A of the imaging region R by the distance DL2, which becomes larger than the distance DL1. For this reason, when passing through the portion located close to the rear of the head P, the X-ray detector 128 is largely separated toward the −Y side (rear side) with respect to the imaging region R as compared with the case that the X-ray detector 128 passes through the portion located close to the front of the head P.

When the X-ray generator 126 and the X-ray detector 128 are turned as described above, the distance between the X-ray generator 126 and the imaging region R and the distance between the X-ray detector 128 and the imaging region R fluctuate continuously. In the example of FIG. 10, the X-ray detector 128 is kept closest to the imaging region R in the first orbit Q1 (from T1 toward T5). For this reason, the enlargement ratio is kept at the minimum. In the second orbit Q2 (from T5 toward T1), the imaging region R becomes the state furthest away from the X-ray detector 128 from the state closest to the X-ray detector 128, and then the imaging region R becomes the state closest to the X-ray detector 128. The enlargement ratio becomes the maximum at the position T7 where the X-ray detector 128 is furthest away from the imaging region R.

As described above, because the position of the imaging region R between the X-ray generator 126 and the X-ray detector 128 fluctuates relatively, a regulating width of the X-ray to be regulated by the X-ray regulating unit 129 (the width of the X-ray regulating hole) may be controlled. The regulating width is set in a range, in which the width of the X-ray cone beam that is emitted from the X-ray generator 126 and regulated by the X-ray regulating unit 129 passes through the whole imaging region R and the surrounding area of the imaging region R is not excessively irradiated with the X-ray. The regulating width may be controlled using the turning angle by the turning mechanism 132 as a parameter. A reference table in which the regulating width is correlated with the turning angle by the turning mechanism 132 is previously stored, and the regulating width may be controlled based on the reference table.

For example, the X-ray regulating unit 129 is constructed with four X-ray shielding members, and is disposed on a front surface of an X-ray irradiation port of the X-ray generator 126 on the +z side, the −z side, +x side, and −x side centered on the X-ray irradiation port. The X-ray shielding member on the +z side and the X-ray shielding member on the −z side are independently driven so as to be displaceable in the z direction, the X-ray shielding member on the +x side and the X-ray shielding member on the −x side are independently driven so as to be displaceable in the x direction, and the drive of the X-ray shielding members is controlled by an X-ray regulating unit drive controller (not illustrated). The space surrounded by the X-ray shielding members is the region through which the X-ray can pass, and is the X-ray regulating hole. The X-ray regulating hole having a desired shape is formed by displacement drive control of the four X-ray shielding members. In other words, the region through which the X-ray can pass, namely, the X-ray regulating hole is an X-ray passage permitting unit. The regulating width means the width of the regulated space, and is the width of the X-ray passage permitting unit, namely, the width of the X-ray regulating hole. Thus, the relationship that the regulating width is decreased to increase the regulation amount and the regulating width is increased to decrease the regulation amount holds.

Figure 20:
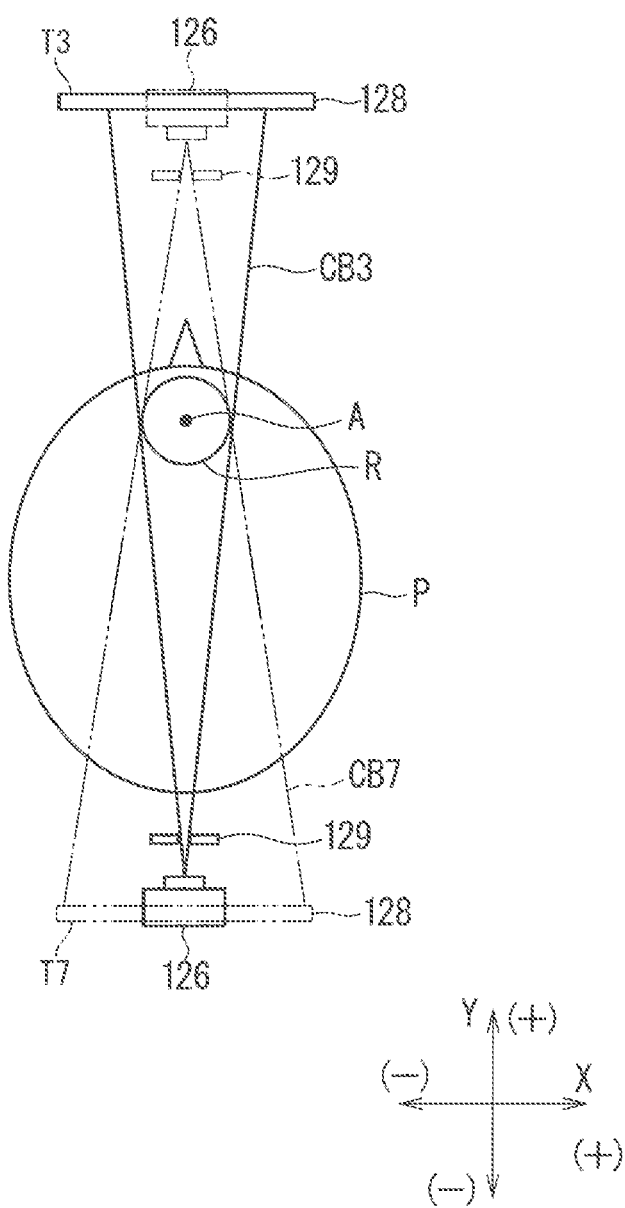
FIG. 20 is an explanatory view illustrating a control example of X-ray cone beam formation by an X-ray regulating unit.

A control example of formation of an X-ray cone beam CB by the X-ray regulating unit 129 will be described with reference to FIG. 20. FIG. 20 illustrates a control example of the formation of the X-ray cone beam CB by the X-ray regulating unit 129 at T3 and T7 in the timings of the movement of the X-ray detector 128 in FIG. 10 in order to simplify and clarify the description. Sometimes an X-ray cone beam CB3 in the timing T3 and an X-ray cone beam CB7 in the timing T7 are distinguished from each other.

When the timing T3 and the timing T7 are compared, the imaging region R and the center A of the imaging region R in the timing T3 are farther from the X-ray generator 126 than the case of the timing T7, and are closer to the X-ray detector 128 than the case of the timing T7.

Because the X-ray cone beam CB spreads largely as moving away from the X-ray generator 126, in the case that the imaging region R is far from the X-ray generator 126 as in the timing T3, the regulating width of the X-ray regulating part 129 is decreased such that the X-ray cone beam CB3 does not spread largely, the X-ray cone beam CB3 passes through the whole imaging region R, and the surroundings of the imaging region R are not excessively irradiated with the X-ray.

On the other hand, in the case that the imaging region R is close to the X-ray generator 126 as in the timing T7, it is necessary to widen the X-ray cone beam CB7 to the width corresponding to the imaging region R at a position relatively close to the X-ray generator 126. That is, it is necessary to widen the X-ray cone beam CB7 larger than the X-ray cone beam CB3. The regulating width of the X-ray regulating unit 129 is increased larger than the regulating width in the case of the timing T3, which allows the X-ray cone beam CB7 to pass through the whole imaging region R while the surroundings of the imaging region R are not excessively irradiated with the X-ray.

That is, as the distance between the X-ray generator 126 and the imaging region R is shortened, the regulating width of the X-ray regulating unit 129 is increased. Conversely, as the distance between the X-ray generator 126 and the imaging region R is lengthened, the regulating width of the X-ray regulating unit 129 is decreased, which allows the X-ray cone beam CB to pass through the whole imaging region R while the surroundings of the imaging region R are not excessively irradiated with the X-ray.

When attention is paid to the enlargement ratio, in the timing T3, the imaging region R is farther from the X-ray generator 126 than the case of the timing T7, and is close to the X-ray detector 128 than the case of the timing T7. For this reason, the imaging region R is projected while enlarged with the small enlargement ratio with respect to the X-ray detector 128. On the other hand, in the timing T7, the imaging region R is relatively closer to the X-ray generator 126 than the case of the timing T3, and relatively farther to the X-ray detector 128 than the case of the timing T3. For this reason, the imaging region R is projected while enlarged with the large enlargement ratio with respect to the X-ray detector 128 as compared with the case of the timing T3.

That is, the enlargement ratio increases as the imaging region R between the X-ray generator 126 and the X-ray detector 128 is closer to the X-ray generator 126 (conversely, as the imaging region R is farther from the X-ray detector 128). Conversely, the enlargement ratio decreases as the imaging region R between the X-ray generator 126 and the X-ray detector 128 is closer to the X-ray detector 128 (conversely, as the imaging region R is farther from the X-ray generator 126).

The turning axis moving mechanism 134 can be recognized as a curvature changing mechanism that adjusts the curvature of the go-around orbit Q by adjusting the distance between the X-ray detector 128 and the center A of the imaging region R such that the turning axis X1 is located to a fixed position while the X-ray detector 128 is turned by the turning mechanism 132, and such that the turning axis X1 is moved along the axis distance changing orbit S having an elliptic shape that is not a circular shape while the X-ray detector 128 is turned. In the case that the X-ray CT imaging is performed with a part located close to the front of the head P as an imaging region R, using the turning mechanism 132 and the turning axis moving mechanism 134 that is the curvature changing mechanism, the turning controller 151*b* causes X-ray generator 126 and the X-ray detector 128 to turn around the head P while locating the imaging region R therebetween, and changes the curvature of the go-around orbit Q by changing the distance between the X-ray detector 128 and the center A of the imaging region R.

When the turning controller 151*b* causes the X-ray generator 126 and the X-ray detector 128 to turn at least 360° using the turning mechanism 132, the X-ray CT imaging is ended. Consequently, the X-ray CT imaging projection image data necessary for the generation of the X-ray CT image of the imaging region R is obtained, and the X-ray CT image is generated based on the X-ray CT imaging projection image data.

The X-ray generator 126 and the X-ray detector 128 do not necessarily turn at least 360°. The X-ray generator 126 and the X-ray detector 128 may turn less than 360°, for example, 270° and 180° to perform the X-ray CT imaging. Even in this case, the setting of the go-around orbit Q is effective when the X-ray detector 128 passes through the portions located close to front and the rear of the head P.

In the configuration in which the turning axis X1 is moved along the axis distance changing orbit S, the turning controller 151*b* that controls the turning mechanism 132 and the turning axis moving mechanism 134 performs control as follows. The control of the X-ray regulating unit 129 is also performed as necessary. The position control of the X-ray generator 126 and the X-ray detector 128 is performed by driving the turning support 124.

That is, the X-ray generator 126 and the X-ray detector 128 are opposed to each other with the region of interest R interposed therebetween, and the control of keeping the opposed relationship is performed. The control of turning the X-ray generator 126, the X-ray detector 128, and the turning axis X1 in the same direction based on whether the X-ray generator 126, the X-ray detector 128, and the turning axis X1 are turned clockwise or counterclockwise. The control is performed such that the X-ray cone beam emitted from the X-ray generator 126 turns about the center A of the imaging region R. Preferably, the control is performed such that the center line of the spread in the x direction of the X-ray cone beam emitted from the X-ray generator 126 passes through the center A of the imaging region R. Preferably, the control is performed such that the X-ray generator 126, the X-ray detector 128, and the turning axis X1 turn synchronously by the same turning angle. Preferably, the control is performed such that the X-ray generator 126, the X-ray detector 128, and the turning axis X1 turn about the center A of the imaging region R.

<Effect>

In the X-ray CT imaging apparatus 110 configured as described above, by changing the distance between the X-ray detector 128 and the center A of the imaging region R, the X-ray detector 128 is turned along the go-around orbit Q, which comes close to the imaging region R with respect to the front side of the head P and moves away from the imaging region R with respect to the rear side. Consequently, the X-ray detector 128 can be turned as close to the head P as possible while the X-ray generator 126 and the X-ray detector 128, which turn around the head P, are prevented from contacting with the head P, and the clear X-ray CT image can be obtained.

Because the go-around orbit Q is an orbit that does not include a concave portion toward the imaging region R, the change in the inner and outer directions of the go-around orbit Q is decreased during turning of the X-ray detector 128, and the X-ray detector 128 is hardly shaken. From this point, the clear X-ray CT image can be obtained.

Because the X-ray detector 128 turns along the circular or elliptic go-around orbit Q, the X-ray detector 128 is hardly shaken. From this point, the clear X-ray CT image can be obtained.

Because the X-ray detector 128 comes closest to the imaging region R at the front of the head P, the clear X-ray CT image of the front tooth region can be obtained.

In the equidistant moving orbit Q1, the X-ray detector 128 moves while maintaining the equidistance with respect to the center A of the imaging region R, so that the X-ray detector 128 is hardly shaken, and the clear X-ray CT image is easily obtained from this point.

In the second preferred embodiment, the turning axis moving mechanism 134 that moves the turning axis X1 on the mechanism is provided as the distance changing mechanism. Under the control of the turning controller 151b, in synchronization with the turning of the turning support 124 using the turning mechanism 132, the turning axis moving mechanism 134 moves the turning axis X1 on the mechanism to cause the turning support 124 to perform the combined movement, whereby the go-around orbit Q of the X-ray detector 128 with respect to the head P can be controlled.

In this case, the go-around orbit Q includes the first orbit Q1 that comes close to the imaging region R on the side on which the imaging region R is biased in the head P and the second orbit Q2 that moves away from the imaging region R on the side opposite to the side on which the imaging region R is biased in the head P. The turning axis moving mechanism 134 changes the position of the turning axis X1 on the mechanism in each of the first orbit Q1 and the second orbit Q2 to the direction (the front-rear direction) parallel to the direction in which the imaging region R is biased with respect to the center of the head P, thereby forming the go-around orbit Q. Consequently, the first orbit Q1 that comes close to the imaging region R on the side on which the imaging region R is biased in the head P and the second orbit Q2 that moves away from the imaging region R on the side opposite to the side on which the imaging region R is biased in the head P can be formed.

In the second preferred embodiment, in the period in which the X-ray detector 128 turns, the turning axis X1 on the mechanism is located in the center A of the imaging region R in at least a part of the period in which the X-ray detector 128 passes through the portion located close to the front of the head P, and the turning axis X1 on the mechanism moves in other periods. Because the turning axis X1 is located at a fixed position on the center A of the imaging region R in at least a part of the period in which the X-ray detector 128 passes through the portion located close to front of the head P, the X-ray detector 128 is hardly shaken, and the clear X-ray CT image is easily generated.

The center line of the X-ray emitted from the X-ray generator 126 passes through the center A of the imaging region R, and is incident on the X-ray detector 128. The X-ray CT image can easily be generated based on the detection result of the X-ray detector 128.

In the second preferred embodiment, under the control of the turning controller 151b, the turning axis moving mechanism 134 that moves the turning axis X1 is the curvature changing mechanism that adjusts the curvature of the go-around orbit Q by adjusting the distance between the X-ray detector 128 and the center A of the imaging region R when the turning mechanism 132 turns the X-ray generator 126. By changing the curvature of the go-around orbit Q of the X-ray detector 128, the X-ray detector 128 can be turned along the go-around Q, which comes close to the imaging region R with respect to the front side of the head P and moves away from the imaging region R with respect to the rear side. With this control, the X-ray detector 128 is hardly shaken due to the absence of mechanically sharp movement change, and the clear X-ray CT image is easily obtained.

In particular, in the case that the X-ray CT imaging is performed by turning the X-ray generator 126 and the X-ray detector 128 at least 360°, a projection data signal of the X-ray irradiation from one direction and a projection data signal of the X-ray irradiation from the opposed direction can be obtained in each X-ray irradiation from multiple directions with respect to all points in the imaging region R, and the CT image having better quality can be reconstructed.

<Modifications>

Various modifications based on the second preferred embodiment will be described below. Hereinafter, like a "go-around orbit QA", one to which some letters are appended subsequent to the "go-around orbit Q" is an example of the go-around orbit Q, and is at least a part of the "go-around orbit Q". Similarly, like an "axis distance changing orbit SA", one to which some letters are appended subsequent to the "axis distance changing orbit S" is an example of the axis distance changing orbit S, and is at least a part of the "axis distance changing orbit S".

<First Modification>

In the description of a first modification, the go-around orbit QA includes an equidistant moving orbit QA1 in which the X-ray detector 128 moves while keeping the equidistance from the center A of the imaging region R during the passage of the X-ray detector 128 through the portion located close to front of the head P, and a remaining orbit QA2 of the equidistant moving orbit QA1 in the go-around orbit QA is a distance changing moving orbit QA2 in which the X-ray detector 128 moves while changing the distance with respect to the center A of the imaging region R.

Figure 11:
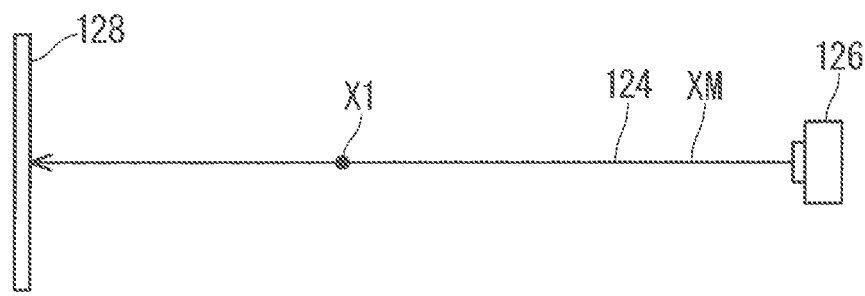
FIG. 11 is an explanatory view illustrating an example of a positional relationship between an X-ray detector according to a first modification and a head.
Figure 11:
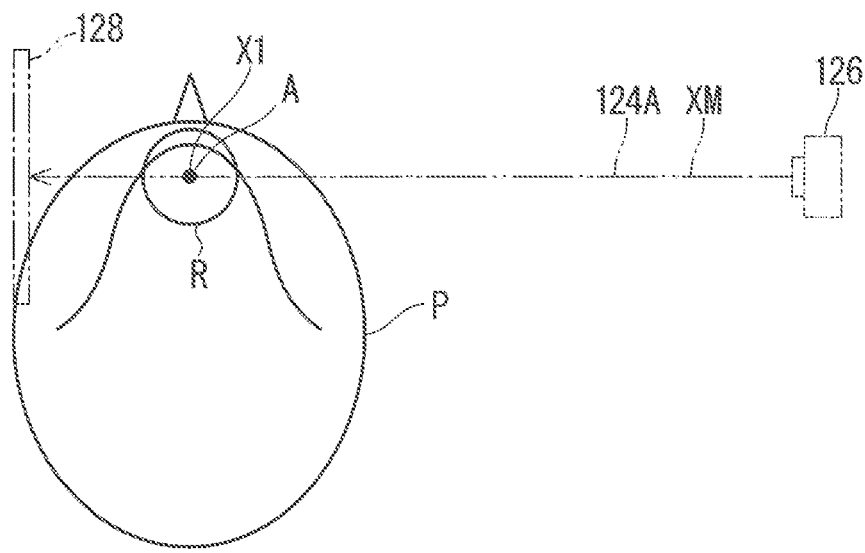
Figure 11:
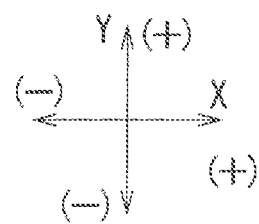

In the first modification, as illustrated in FIG. 11, a structure in which the position of the turning axis X1 in a turning support 124A is closer to the side of the X-ray detector 128 than the position of the turning axis X1 in the turning support 124 of the second preferred embodiment is used as the structure of the turning support 124A corresponding to the turning support 124. In this case, because the distance between the turning axis X1 and the X-ray detector 128 is short, the X-ray detector 128 can come into contact with the head P when the turning support 124A is turned while the turning axis X1 is matched with the center A of the imaging region R.

Figure 12:
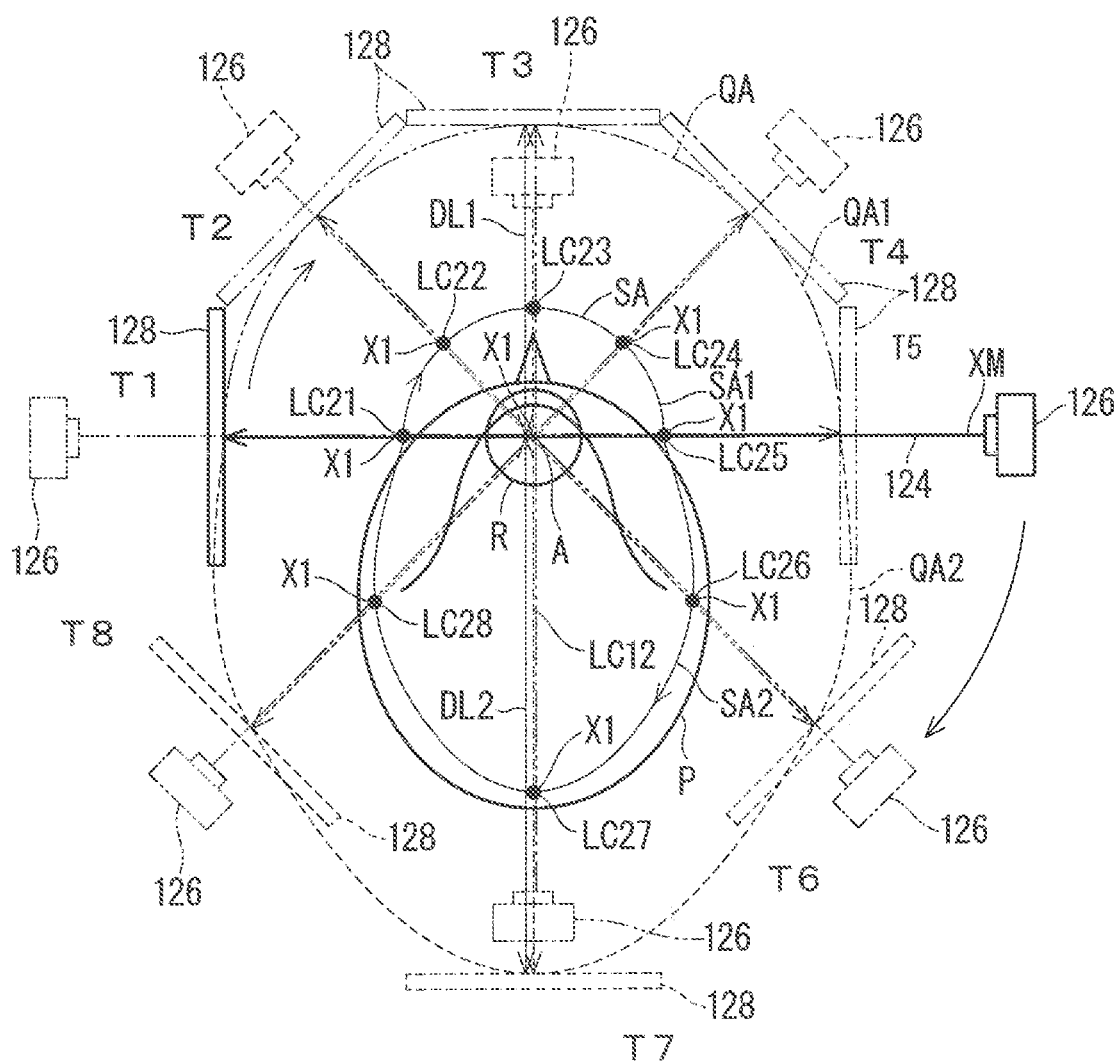
FIG. 12 is an explanatory view illustrating an example of a moving orbit of a turning axis and a go-around orbit of an X-ray detector according to the first modification.

For this reason, as illustrated in FIG. 12, even while the X-ray detector 128 passes through the portion located close to front of the head P, the turning controller 151b controls the turning axis moving mechanism 134 to turn the turning axis X1 about the center A of the imaging region R.

On the front side of the head P, the axis distance changing orbit SA of the turning axis X1 includes an orbit SA1 that draws an arcuate shape centered on the center A of the imaging region R. At this point, the orbit SA1 draws a semicircular shape.

On the rear side of the head P, the orbit SA of the turning axis X1 draws an axis distance changing orbit SA2 having an elliptic shape elongated in the front-rear direction of the head P, namely, forming a part of an elliptic shape in which a long axis extends in the front-rear direction. The axis distance changing orbit SA2 has a shape, in which a part located close to the front of the ellipse is deleted and both ends of the ellipse are connected to both ends of the orbit SA1.

For this reason, when viewed as a whole, the axis distance changing orbit SA has a snowman shape.

In synchronization with the turning of the turning support 124 about the turning axis X1 using the turning mechanism 132, the turning controller 151b controls the turning axis moving mechanism 134 to move the turning axis X1 along the axis distance changing orbit SA, and causes the turning support 124A to perform the combined movement, thereby controlling the go-around orbit Q of the X-ray detector 128 with respect to the head P. During turning, in order to move the X-ray detector 128 away from the imaging region R, the turning axis X1 turns at the position on the side of the X-ray detector 128 with respect to the center A of the imaging region R.

At this point, the moving speed (position) of the turning axis X1 in the axis distance changing orbit SA is controlled such that the X-ray detector 126 and the X-ray detector 128 turn while the state in which the center line XM of the X-ray emitted from the X-ray generator 126 passes through the center A of the imaging region R is maintained.

The portion in which the axis distance is kept constant while the X-ray generator 126 and the X-ray detector 128 turns around the imaging region R with respect to the axis orbit S may be referred to as an axis equidistance region. The portion, such as the orbit SA1, in which the axis distance is kept constant while the X-ray detector 128 passes through the portion located close to front of the head P with respect to the axis orbit SA, namely, the axis distance changing orbit SA, becomes the axis equidistance region. On the other hand, as in the axis distance changing orbit SA2, the portion in which the axis distance except for the axis equidistance region changes in the axis orbit SA may be referred to as an axis distance changing region. In the example of FIG. 12, the axis orbit SA is constructed with the axis equidistance region and the axis distance changing region.

In the example of FIG. 12, a semicircular arcuate shape centered on the center A of the imaging region R is drawn in the equidistance moving orbit QA1 in which the X-ray detector 128 passes through the portion located close to the front of the head P in the go-around orbit QA. The distance changing moving orbit QA2 that is the remaining orbit QA2 of the equidistance moving orbit QA1 in the go-around orbit QA draws a partially elliptic shape. The connecting portion between the equidistance moving track QA1 and the distance changing moving track QA2 is recessed inward.

The go-around orbit QA may be an orbit that does not include a portion concave toward the center A of the imaging region R by appropriately adjusting the moving orbit of the turning axis X1. For example, the axis distance changing orbit SA2 of the turning axis X1 closer to the rear of the head P may draw an orbit that does not move to the outside of the head P from both ends of the orbit SA1 of the turning axis X1 closer to the front of the head P toward the rear of the head P. The orbit SA1 of the turning axis X1 close to the front of the head P may draw an orbit having a center angle of 180° or less, and draw the axis distance changing orbit SA2 close to the rear of the head P from both ends of the orbit SA1. The vicinity at both ends of the orbit SA1 and the axis distance changing orbit SA2 in the connection portion between the orbit SA1 and the axis distance changing orbit SA2 may slightly be bulged outward from the center A to form a smooth closed curve without a concave portion.

In the example of FIG. 12, in the timing at which the X-ray detector 128 is located on the −X direction side (see T1), the turning axis X1 is located at a position LC21 closer to the −X direction with respect to the center A of the imaging region R. In the timing at which the X-ray detector 128 is located closer to the combined direction of the component in the −X direction and the component in the +Y direction (see T2), the turning axis X1 on the mechanism is located at a position LC22 closer to the combined direction of the component in the −X direction and the component in the +Y direction with respect to the center A of the imaging region R. In the timing at which the X-ray detector 128 is located on the +Y direction side (see T3), the turning axis X1 is located at a position LC23 closer to the +Y direction with respect to the center A of the imaging region R. In the timing at which the X-ray detector 128 is positioned closer to the combined direction of the component in the +X direction and the component in the +Y direction (see T4), the turning axis X1 on the mechanism is located at a position LC24 closer to the combined direction of the component in the +X direction and the component in the +Y direction with respect to the center A of the imaging region R. In the timing at which the X-ray detector 128 is located on the +X direction side (see T5), the turning axis X1 is located at a position LC25 closer to the +X direction with respect to the center A of the imaging region R. In the timing at which the X-ray detector 128 is located closer to the combined direction of the component in the +X direction and the component in the −Y direction (see T6), the turning axis X1 on the mechanism is located at a position LC26 closer to the combined direction of the component in the +X direction and the component in the −Y direction with respect to the center A of the imaging region R. In the timing at which the X-ray detector 128 is located on the −Y direction side (see T7), the turning axis X1 is located at a position LC27 closer to the −Y direction with respect to the center A of the imaging region R. In the timing at which the X-ray detector 128 is located closer to the combined direction of the component in the −X direction and the component in the −Y direction (see T8), the turning axis X1 on the mechanism is located at a position LC28 closer to the combined direction of the component in the −X direction and the component in the −Y direction with respect to the center A of the imaging region R.

When the X-ray detector 128 moves from the position T1 to the position T5 through the positions T2, T3, T4, the turning axis X1 moves on the semicircular arcuate orbit SA1 with the imaging region R as the center. As a result, the diameter DL2 of the orbit QA1 of the X-ray detector 128 becomes the diameter in which the turning diameter of the turning axis X1 is added to the distance L2 between the turning axis X1 and the X-ray detector 128. When the X-ray detector 128 moves from the position T5 to the position T1 through the positions T6, T7, T8, the turning axis X1 moves along the axis distance changing orbit SA2. The axis distance changing orbit SA2 has a partially elliptic shape in which an ellipse elongated in the front-back direction of the head P is divided by a line along a short-axis direction, and extends so as to be curved while becoming greatly convex toward the rear of the head. For this reason, at the positions T6 to T8, the turning axis X1 is located at the positions LC26, LC27, LC28 that are largely away from the center A of the imaging region R in the −Y direction. The separation distance with respect to the center A becomes the maximum at the position LC27. The X-ray detector 128 is separated from the center A of the imaging region R by the distance in which the large distance between the turning axis X1 and the center A of the imaging region R is added to the distance L2 between the turning axis X1 and the X-ray detector 128. In particular, at the position T7, the distance DL2 between the X-ray detector 128 and the center A of the imaging region R is larger than the distance DL1. For this reason, when passing through the portion located close to the rear of the head P, the X-ray detector 128 is largely separated toward the −Y side (rear side) with respect to the imaging region R as compared with the case that the X-ray detector 128 passes through the portion located close to the front of the head P.

In the first modification, even in the case that the position of the turning axis X1 is close to the X-ray detector 128, while the X-ray detector 128 is prevented from coming into contact with the head P, the X-ray detector 128 can turn around the head P while brought close to the imaging region R as much as possible.

The same effect as the second embodiment can be obtained.

<Second Modification>

In a second modification, the processing in the case that a second imaging region including the molar region is set as the imaging region in step S11 of FIG. 6 will be described.

That is, in the head P, it is assumed that a certain region and another region can be designated as the imaging region R, that the certain region is a first imaging region R1, and that another region is a second imaging region R2, and the X-ray CT imaging is performed on the first imaging region R1 and the second imaging region R2. The X-ray CT imaging having the above advantage described in the first or second preferred embodiment is performed on the first imaging region R1. For example, as described in the second preferred embodiment, in the case that the X-ray CT imaging is performed on the first imaging region R1 including the front tooth region as a part of the imaging region R located close to the front of the head P, the X-ray detector 128 is turned along the go-around orbit Q to perform the X-ray CT imaging.

The X-ray CT imaging having another advantage is performed on the second imaging region R2. The second imaging region R2 is typically a part of the region located close to the left or right side of the head P, and the region including any one of the left and right molar teeth described above is an example of the second imaging region R2. The region including one of the left and right temporomandibular joint may be set as the second imaging region R2. The second modification is an example in which the above is assumed.

It is assumed that the main body in FIGS. 9 and 10 is used as the imaging main body 120, and the second imaging region R2 including the molar region is set as the imaging region R. The second imaging region R2 including the molar region can be set as the imaging region R using the user interface and the like in FIGS. 7 and 8 as described above.

Figure 13:
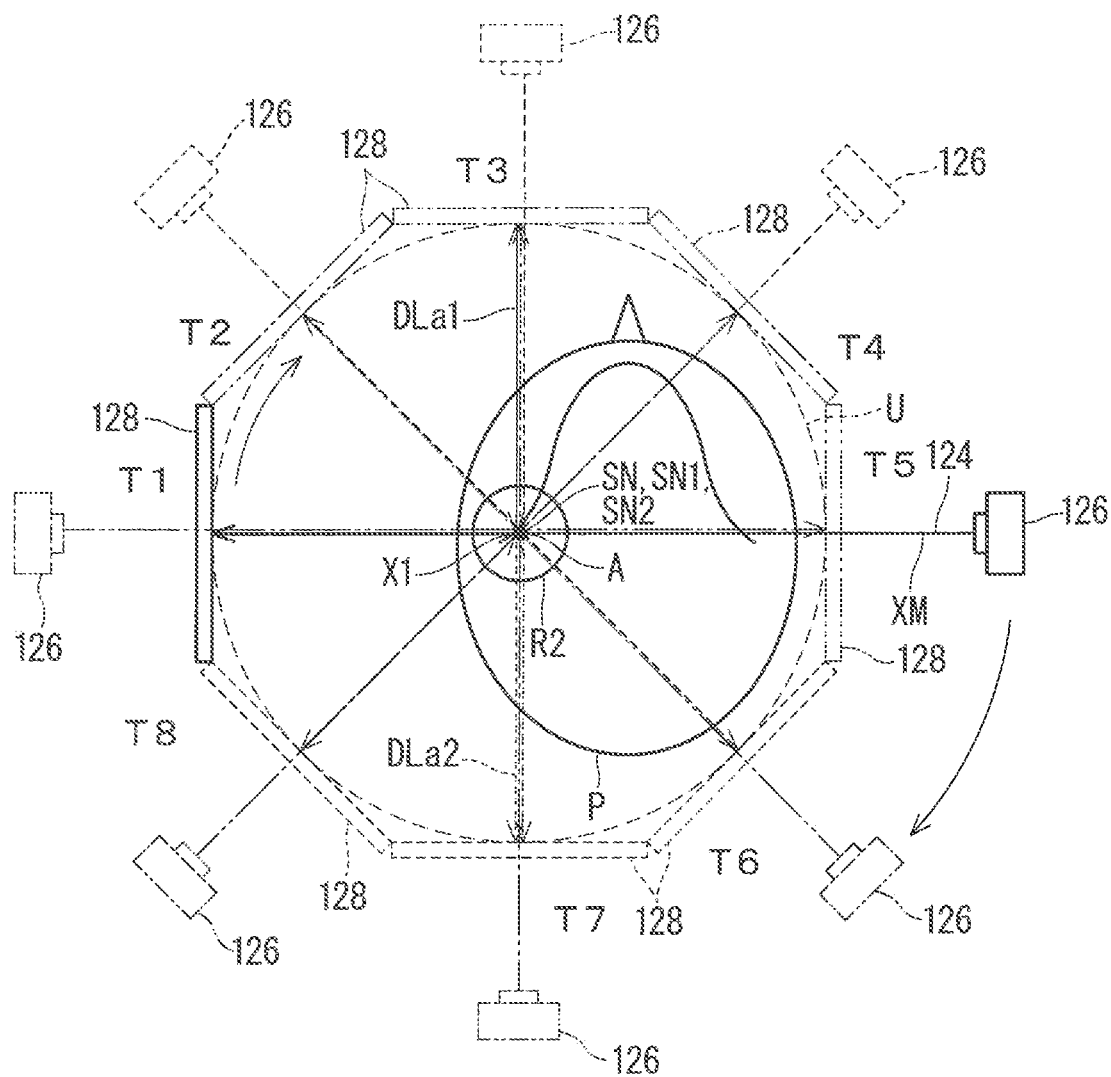
FIG. 13 is an explanatory view illustrating an example of a go-around orbit of an X-ray detector according to a second modification.
Figure 13:
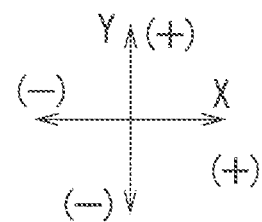

As illustrated in FIG. 13, in the case that the second imaging region R2 including the molar region is set as the imaging region R, the second imaging region R2 exists in the substantial center or the vicinity of the center in the front-rear direction of the head P. For this reason, the distance between the X-ray detector 128 and the center A of the imaging region R may not largely be changed between the case that the X-ray detector 128 passes through the front side of the head P and the case that the X-ray detector 128 passes through the rear side of the head P.

By applying a logic in the case of the imaging region R1, the distance between the X-ray detector 128 and the center A in the case that the X-ray detector 128 is located in front of the head P is considered as a minimum value DLa1 of the distance, the distance between the X-ray detector 128 and the center A in the case that the X-ray detector 128 is located in rear of the head P is considered as a maximum value DLa2 of the distance. In the case that the X-ray CT imaging is performed on the second imaging region R2 including the molar region as the imaging region R, using the turning mechanism 132 and the distance changing mechanism (the turning axis moving mechanism 134 based on the second preferred embodiment), the X-ray generator 126 and the X-ray detector 128 are turned around the head P while locating the imaging region R2 therebetween such that a proportion of the minimum value DLa1 to the maximum value DLa2 of the distance between the X-ray detector 128 and the center A of the second imaging region R2 is larger than a proportion of the minimum value DL1 to the maximum value DL2 of the distance between the X-ray detector 128 and the center A of the first imaging region R1 including the front tooth region (see FIG. 10). That is, DLa1/DLa2>DL1/DL2 holds.

In the example of FIG. 13, after the turning axis X1 is moved to the center A of the imaging region R2 by the turning axis moving mechanism 134, the turning support 124 is turned by the turning mechanism 132 while the turning axis X1 is matched with the center A of the imaging region R2 (see step S15). In this case, because the X-ray detector 128 turns with the turning diameter of the distance L2 between the turning axis X1 and the X-ray detector 128, the distance between the X-ray detector 128 and the center A of the second imaging region R2 is kept constant, and both the maximum value DLa2 and the minimum value DLa1 of the distance are L2. Thus, DLa1/DLa2=1 holds. The X-ray detector 128 moves on a go-around orbit U in which the change in a separation degree of the X-ray detector 128 with respect to the imaging region R is zero.

In the second modification, in the example of FIG. 13, the X-ray detector 128 is turned from the −X side to the −X side through the +Y side, the +X side, and the −Y side, and the X-ray detector 128 moves through the positions T1 to T8 on the go-around orbit U and returns to the position T1.

Similarly to the second preferred embodiment, the position or the movement path of the turning axis X1 on the mechanism in the period in which the X-ray detector 128 turns from the −X side to the +X side through the +Y side is set to an orbit SN1 irrespective of the movement of the turning axis X1, and the position or movement path of the turning axis X1 on the mechanism in the period in which the X-ray detector 128 turns from the +X side to the −X side through the −Y side is set to an orbit SN2 irrespective of the movement of the turning axis X1. The orbit SN is constructed with the orbit SN1 and the orbit SN2. Both the orbit SN1 and the orbit SN2 are the axis retention region, and the whole orbit SN is the orbit of the axis retention region.

On the other hand, as described in the second embodiment, in the case that the X-ray CT imaging is performed on the first imaging region R1 including the front tooth region as the imaging region R, the X-ray detector 128 comes closest to the imaging region R2 at the front of the head P, and the minimum value DL1 becomes L2. The X-ray detector 128 is farthest away from the imaging region R2 in the rear of the head P, the maximum value DL2 becomes a value in which the distance in which the turning axis X1 is shifted from the center A of the imaging region R toward the −Y side is added to L2, and DL2>L2 holds. For this reason, DL1/DL2<1 holds.

Thus, in the example of FIG. 13, DLa 1/DLa2>DL1/DL2 is established. In the case that the X-ray CT imaging is performed on the second imaging region R2 including the molar region as the imaging region R, using the turning mechanism 132 and the distance changing mechanism (the turning axis moving mechanism 134 based on the second preferred embodiment), the X-ray generator 126 and the X-ray detector 128 are turned around the head P while locating the imaging region R2 therebetween such that a proportion of the minimum value DLa1 to the maximum value DLa2 of the distance between the X-ray detector 128 and the center A of the second imaging region R2 is larger than a proportion of the minimum value DL1 to the maximum value DL2 of the distance between the X-ray detector 128 and the center A of the first imaging region R1 including the front tooth region.

In the arrangement structure of the turning support 124, the X-ray generator 126, the X-ray detector 128, and the turning axis X1 on the mechanism in FIGS. 9, 10, and 13, when the turning support 124 is turned while the position of the turning axis X1 on the mechanism is matched with the center A of the imaging region R including the front tooth region, the X-ray detector 128 can contact with the head P when the X-ray detector 128 passes through the rear side of the head P. In the arrangement structure of the second modification, even if the turning support 124 is turned while the position of the turning axis X1 on the mechanism is matched with the center A of the imaging region R including the molar region, there is no risk that the X-ray detector 128 contacts with the head P at any angle, so that in the imaging region R including the molar region, the maximum distance DLa2 and the minimum distance DLa1 of the distance are set to L2 as described above.

From the viewpoint of the relationship with the head, this may be defined as follows.

In the second preferred embodiment, it is assumed that a partial region located close to the front of the head P is the first imaging region R1, that YL1 (=DL1) is the distance between the X-ray detector 128 and the center A when the X-ray detector 128 passes through a frontmost point (the point at which the coordinate in the Y direction on the go-around orbit in front of the head P) with respect to the head P, and that YL2 (=DL2) is the distance between the X-ray detector 128 and the center A when the X-ray detector 128 passes through the rearmost point (the point at which the coordinate in the Y direction on the go-around orbit at the rear of the head P) with respect to the head P.

In the second modification, it is assumed that a partial region located close to one of the right and the left of the head P is the second imaging region R2, that YLa1 (=DLa1) is the distance between the X-ray detector 128 and the center A when the X-ray detector 128 passes through a frontmost point (the point at which the coordinate in the Y direction on the go-around orbit in front of the head P) with respect to the head P, and that YLa2 (=DLa2) is the distance between the X-ray detector 128 and the center A when the X-ray detector 128 passes through the rearmost point (the point at which the coordinate in the Y direction on the go-around orbit at the rear of the head P) with respect to the head P.

The X-ray generator 126 and the X-ray detector 128 are turned around the head P while locating the imaging region R2 therebetween such that YLa1/YLa2>YL1/YL2 holds in imaging the second imaging region R2.

This arrangement condition may be decided based on the head P of a standard skeleton, or decided based on the head P of the larger skeleton when multiple standard skeletons are presumed. Alternatively, the arrangement condition may be decided based on the head P of the largest skeleton among the skeletons considered to be the head P.

Alternatively, the head of each individual may be decided based on the individual head set by a head size setting apparatus. The head size setting apparatus may measure an opening degree of a movable member that holds the head like a head holder, measure the size of the head on the X-ray image obtained by the X-ray imaging performed on the head by image recognition, or receive a size designation operation for the displayed X-ray image.

For example, the amount of change in the axis distance changing orbit S may be changed according to the head size of the individual, and the amount of change may be increased with increasing size. Alternatively, as the case in which the axis orbit S is changed according to the head size of the individual, the axis orbit S constructed only with the axis retention region or only with the equidistance region may be applied to both the first imaging region R1 and the second imaging region R2 based on a predetermined reference size in the case that the head size is small.

The turning axis X1 is not necessarily located in the center A of the imaging region R even in the case that the X-ray CT imaging is performed on the second imaging region R2 including the molar region as the imaging region R. The X-ray CT imaging may be performed while the turning axis X1 is turned around the center A of the imaging region R. In this case, the turning axis X1 may be turned into an elliptical shape. The maximum value DLa2 and the minimum value DLa1 of the distance between the X-ray detector 128 and the center A of the second imaging region R2 may be different from each other.

In the second modification, the X-ray generator 126 and the X-ray detector 128 are turned such that the proportion of the minimum value DLa1 to the maximum value DLa2 of the distance between the X-ray detector 128 and the center A of the second imaging region R2 is smaller than the proportion of the minimum value DL1 to the maximum value DL2 of the distance between the X-ray detector 128 and the center A of the first imaging region R1 in which the front tooth is set to the target. Consequently, in the case that the X-ray CT imaging is performed on the first imaging region R1, the X-ray detector 128 hardly comes into contact with the head P, and the same effect as the second embodiment can be obtained. In the case that the X-ray CT imaging is performed on the second imaging region R2, the X-ray detector 128 changes smoothly in an inner circumferential direction and an outer circumferential direction, the X-ray detector 128 is hardly shaken, and the clear X-ray CT image is easily generated.

In the second modification, in the case that the X-ray CT imaging is performed on the region of the head P different from the front tooth region as the second imaging region R2, the distance between the X-ray detector 128 and the center A of the second imaging region R2 is kept constant (the enlargement ratio of the second imaging region R2 is also kept constant), and the X-ray generator 126 and the X-ray detector 128 are turned around the head P while the second imaging region R2 is located therebetween. For this reason, the X-ray generator 126 and the X-ray detector 128 draw the stable go-around orbit. Consequently, the clear X-ray CT image is easily obtained.

Returning to the first modification, supplement is given. In the first modification, it is conceivable that a partial region located close to the front of the head P indicated as the imaging region R in FIG. 12 is set to the first imaging region R1, and that a partial region located close to one of the right and the left of the head P is set to the second imaging region R2. It is conceivable that the X-ray CT imaging is performed on the second imaging region R2 by the turning support 124A used in the first modification. In this case, assuming that the turning support 124A is turned while the turning axis X1 on the mechanism is set to the position of the center A of the second imaging region R2, in the case that the X-ray detector 128 can contact with the head P when the X-ray detector 128 passes through the rear of the head P, the X-ray CT imaging is performed while the turning axis X1 on the mechanism is turned around the center A of the second imaging region R2. More specifically, with respect to the first imaging region R1, the orbit SA1 of the turning axis X1 draws an arcuate shape in which the distance from the center A with the center A of the imaging region R as the center is the equidistance. With respect to the second imaging region R2, the orbit of the turning axis X1 over the whole go-around orbit of the X-ray detector 128 draws an arcuate shape (for example, a perfect circle) in which the distance from the center A with the center A of the imaging region R as the center is the equidistance.

In this case, the relationship of DLa1/DLa2>DL1/DL2 and the relationship of YLa1/YLa2>YL1/YL2 are applied to the first imaging region R1 and the second imaging region R2.

<Third Modification>

In a third modification, an example in which the go-around orbit QB is an orbit in which the X-ray detector 128 moves while changing the distance with respect to the center A of the imaging region R in the whole circumference of the head P will be described. Because the third modification is based on the turning axis moving mechanism 134 as the distance changing mechanism, the third modification is an example in which the turning axis X1 on the mechanism moves in the whole period in which the X-ray detector 128 turns.

Figure 14:
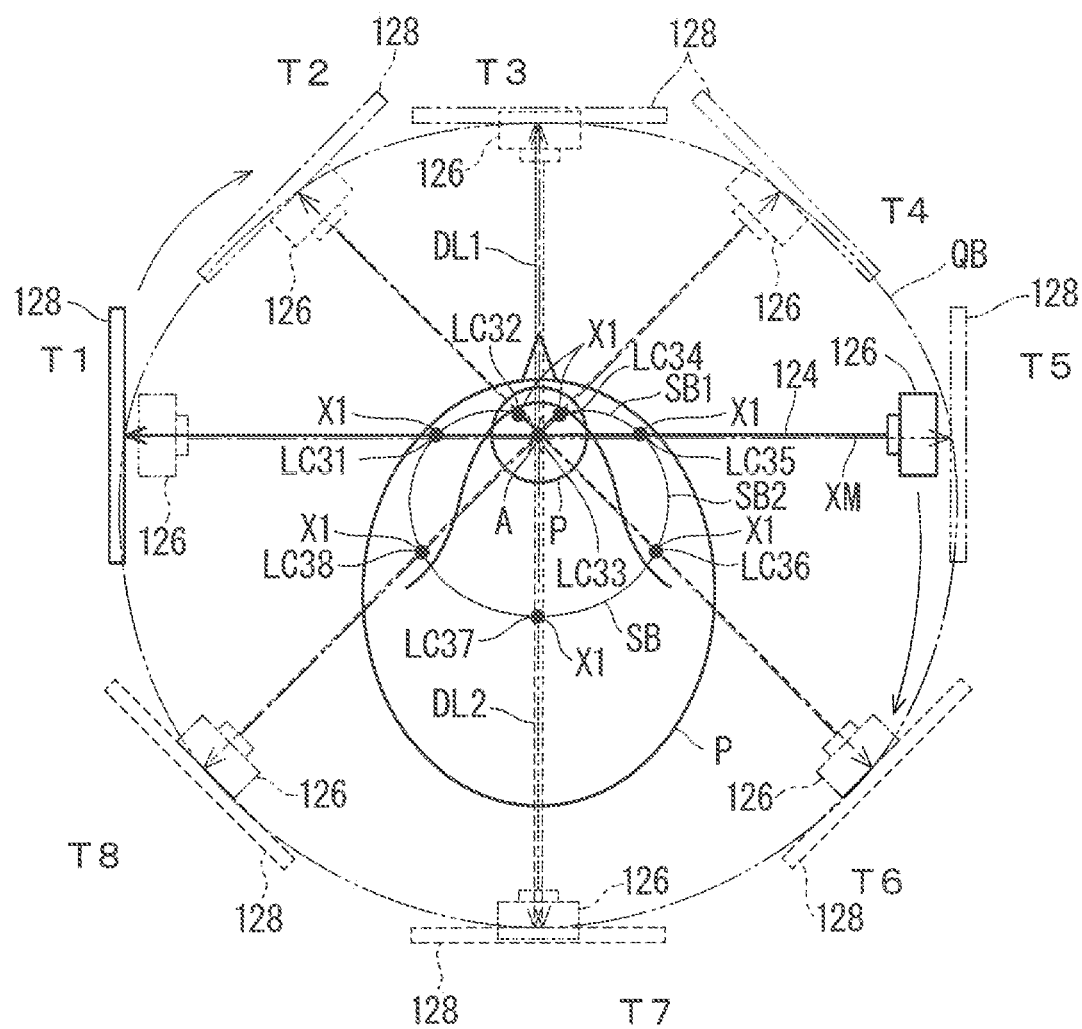
FIG. 14 is an explanatory view illustrating an example of a moving orbit of a turning axis and a go-around orbit of an X-ray detector according to a third modification.

An axis distance changing orbit SB of the turning axis X1 included in the movement control content of the turning axis X1 is illustrated in FIG. 14.

The axis distance changing orbit SB draws a heart shape. An apex portion recessed inward in the axis distance changing orbit SB is located at the center A of the imaging region R, and spreads mainly from the apex portion to the side and rear of the head P.

More specifically, the axis distance changing orbit SB includes an axis distance changing orbit SB1 close to the front in the front-rear direction of the head P in the axis distance changing orbit SB and an axis distance changing orbit SB2 close to the rear in the front-rear direction of the head P in the axis distance changing orbit SB. The axis distance changing orbit SB1 is curved so as to be convex from the center A of the imaging region R to the front side of the head P at each of the right and left sides, and is formed into a shape in which two arc-shaped portions facing both sides of the head P are continued. The axis distance changing orbit SB2 is formed into a horizontally-elongated partially elliptic shape surrounding the rear side of the head P from both ends of the axis distance changing orbit SB1.

As the movement control content of the turning axis X1, it is defined that the turning axis moving mechanism 134 moves the turning axis X1 along the axis distance changing orbit SB in the whole period in which the turning mechanism 132 turns the turn support 124.

When the X-ray detector 128 moves in the go-around orbit Q, the moving speed (position) of the turning axis X1 is controlled in the axis distance changing orbit SB such that the X-ray generator 126 and the X-ray detector 128 turn while the state in which the center line XM of the X-ray emitted from the X-ray generator 126 passes through the center A of the imaging region R is maintained.

In the case that the X-ray CT imaging is performed with a part located close to the front of the head P as the imaging region R, using the turning mechanism 132, the X-ray generator 126 and the X-ray detector 128 are turned around the head P while the imaging region R is located therebetween. In the whole period of the turning movement, the turning axis X1 is moved along the axis distance changing orbit SB using the turning axis moving mechanism 134, thereby changing the distance between the X-ray detector 128 and the center A of the imaging region R. That is, in the case that the turning axis X1 moves along the axis distance changing orbit SB, the distance between the turning axis X1 and the center A of the imaging region R always fluctuates. For this reason, the distance between the X-ray detector 128 and the center A of the imaging region R also fluctuates at all times.

The amount in which the axis distance changing orbit SB2 projects toward the rear side of the head P with respect to the center A of the imaging region R is obviously larger than the amount in which the axis distance changing orbit SB1 protrudes toward the front side of the head P with respect to the center A of the imaging region R. For this reason, the X-ray detector 128 moves along the go-around orbit QB, which comes close to the imaging region R with respect to the front side of the head P and moves away from the imaging region R with respect to the rear side.

In the example of FIG. 14, in the timing at which the X-ray detector 128 is located on the −X direction side (see T1), the turning axis X1 is located at a position LC31 closer to the −X direction with respect to the center A of the imaging region R. In the timing at which the X-ray detector 128 is located closer to the combined direction of the component in the −X direction and the component in the +Y direction (see T2), the turning axis X1 on the mechanism is located at a position LC32 closer to the combined direction of the component in the −X direction and the component in the +Y direction with respect to the center A of the imaging region R. In the timing at which the X-ray detector 128 is located on the +Y direction side (see T3), the turning axis X1 is located at a position LC33 on the center A of the imaging region R. In the timing at which the X-ray detector 128 is located closer to the combined direction of the component in the +X direction and the component in the +Y direction (see T4), the turning axis X1 on the mechanism is located at a position LC34 closer to the combined direction of the component in the +X direction and the component in the +Y direction with respect to the center A of the imaging region R. In the timing at which the X-ray detector 128 is located on the +X direction side (see T5), the turning axis X1 is located at a position LC35 closer to the +X direction with respect to the center A of the imaging region R.

In the timing at which the X-ray detector 128 is located closer to the combined direction of the component in the +X direction and the component in the −Y direction (see T6), the turning axis X1 on the mechanism is located at a position LC36 closer to the combined direction of the component in the +X direction and the component in the −Y direction with respect to the center A of the imaging region R. In the timing at which the X-ray detector 128 is located on the −Y direction side (see T7), the turning axis X1 is located at a position LC37 closer to the −Y direction with respect to the center A of the imaging region R. In the timing at which the X-ray detector 128 is located closer to the combined direction of the component in the −X direction and the component in the −Y direction (see T8), the turning axis X1 on the mechanism is located at a position LC38 closer to the combined direction of the component in the −X direction and the component in the −Y direction with respect to the center A of the imaging region R.

When the X-ray detector 128 moves from the position T1 to the position T5 through the positions T2, T3, T4, the turning axis X1 moves on the axis distance changing orbit SB1 in which two arcuate orbits are continuous. When the X-ray detector 128 moves from the position T5 to the position T1 through the positions T6, T7, T8, the turning axis X1 moves on the elliptic axis distance changing orbit SB2. For this reason, in the whole period of the turning, the X-ray detector 128 is separated from the center A of the imaging region R by the distance in which the distance between the turning axis X1 and the center A of the imaging region R is added to the distance L2 between the turning axis X1 and the X-ray detector 128.

When viewed along the Y axis direction (front-rear direction), the position of the turning axis X1 (for example, the positions LC36, LC37, LC38) in the axis distance changing orbit SB2 is largely away from the center A of the imaging region R as compared with the position (for example, the positions LC32, LC33, LC34) of the turning axis X1 in the axis distance changing orbit SB1. For this reason, when passing through the portion located close to the rear of the head P, the X-ray detector 128 is largely separated toward the −Y side (rear side) with respect to the imaging region R as compared with the case that the X-ray detector 128 passes through the portion located close to the front of the head P.

The go-around orbit QB may be formed into an elliptic shape having a small difference in length between the long axis and the short axis. The positions of the X-ray detector 128 and the X-ray generator 126 in the timing T3 and the positions of the X-ray detector 128 and the X-ray generator 126 in the timing T7 are set, and the elliptic orbit connecting them is set, and the position to be taken by the turning axis X1 may be calculated to define the axis distance changing orbit SB2.

In the third modification, the movement of the X-ray detector 128 is smoothly changed in the inner circumferential direction and the outer circumferential direction. That is, in order to cause the X-ray detector 128 to turn along the go-around orbit QB, which comes close to the imaging region R with respect to the front side of the head P and moves away from the imaging region R with respect to the rear side, it is necessary to change the distance between the X-ray detector 128 and the center A of the imaging region R. As in the third modification, when the X-ray detector 128 moves around the whole head P while changing the distance between the X-ray detector 128 and the center A of the imaging region R, the movement of the X-ray detector 128 can smoothly be changed in the inner circumferential direction and the outer circumferential direction. As a result, the X-ray detector 128 is hardly shaken, and the clear X-ray CT image is easily generated.

In particularly, when the X-ray detector 128 moves around the whole head P, the turning axis X1 on the mechanism moves in the period in which the X-ray detector 128 turns. Consequently, the movement of the X-ray detector 128 can smoothly be changed in the inner circumferential side and the outer circumference side, the X-ray detector 128 is hardly shaken, and the clear X-ray CT image is easily generated.

The third modification can obtain the same effect as in the second embodiment except for the effect obtained by the operations in which, when the X-ray detector 128 passes through the portion located close to the front side of the head P, the X-ray detector 128 moves while maintaining an equidistance from the center A of the imaging region R, and the remaining orbit is the orbit in which the device 128 moves while changing the distance to the center A of the imaging region R, and the effect derived from these operations.

<Fourth Modification>

In a fourth modification, an example in which a go-around orbit QC is an orbit in which the X-ray detector 128 moves while changing the distance to the center A of the imaging region R in the whole circumference of the head P will be described. Because the fourth modification is based on the turning axis moving mechanism 134 as the distance changing mechanism, the fourth modification is also an example in which the turning axis X1 on the mechanism moves in the whole period in which the X-ray detector 128 turns.

Figure 15:
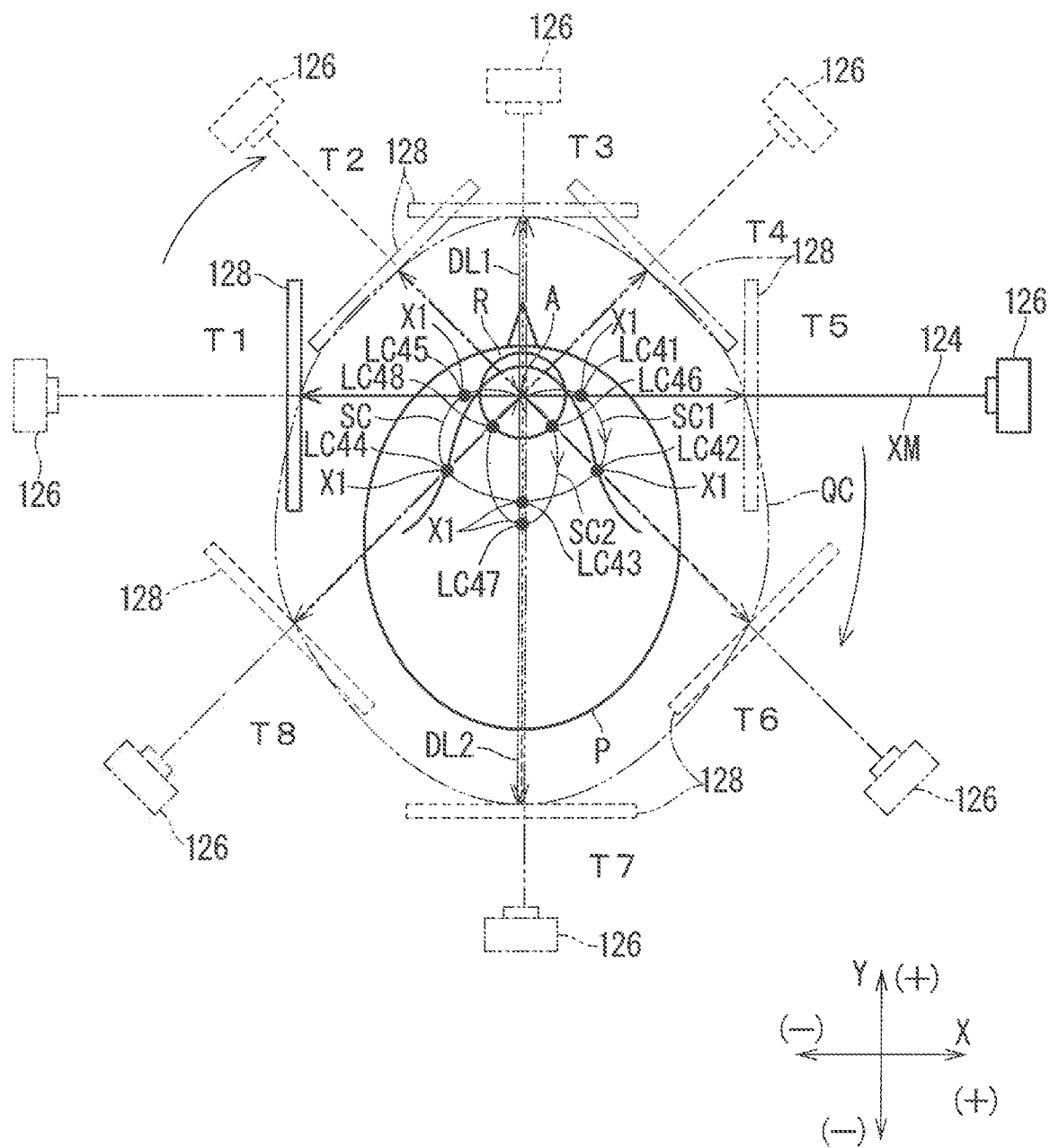
FIG. 15 is an explanatory view illustrating an example of a moving orbit of a turning axis and a go-around orbit of an X-ray detector according to a fourth modification.

An axis distance changing orbit SC of the turning axis X1 included in the movement control content of the turning axis X1 is illustrated in FIG. 15.

The axis distance changing orbit SC includes a first axis distance changing orbit SC1 and a second axis distance changing orbit SC2.

The first axis distance changing orbit SC1 indicates the movement locus of the turning axis X1 in the period in which the X-ray detector 128 mainly passes through the portion located close to the front of the head P. The first axis distance changing orbit SC1 draws a partially elliptical shape. At this point, the long axis of the first axis distance changing orbit SC1 extends in the X axis direction (the left-right direction of the head P). The central portion of the front side in the first axis distance changing orbit SC1 is a missing portion of the elliptic shape, and the portion corresponding to the center of the missing portion is located in the center A of the imaging region R.

The second axis distance changing orbit SC2 indicates the movement locus of the turning axis X1 in the period in which the X-ray detector 128 mainly passes through the portion located close to the rear of the head P.

The second axis distance changing orbit SC2 includes a closed curve region and an extended curve region that protrudes from the central portion on the front side of the closed curve region.

The closed curve region is a closed curve drawing an elliptic shape or a circular shape. At this point, the central portion on the front side of the closed curve area is located in the center of the missing portion of the central portion on the front side in the first axis distance changing orbit SC1. The central portion on the rear side of the closed curve region protrudes outward from the rear side of the first axis distance changing orbit SC1. The width of the closed curve region is smaller than the width of the first axis distance changing orbit SC1, so that both sides of the closed curve region are contained inside the both sides of the first axis distance changing orbit SC1.

The extended curve region extends in the +X direction and in the −X direction (the left-right direction of the head P) from the central portion on the front side of the closed curve region. A pair of extended curve regions reaches both ends leading to the missing portion of the elliptic shape in the first axis distance changing orbit SC1, whereby the first axis distance changing orbit SC1 and the second axis distance changing orbit SC2 are connected to each other.

The turning axis X1 can move from the first axis distance changing orbit SC1 to the second axis distance changing orbit SC2 or vice versa on the way toward the center A of the imaging region R or on the way away from the center A.

As the movement control content of the turning axis X1, it is defined that the turning axis moving mechanism 134 moves the turning axis X1 along the axis distance changing orbit SC in the whole period in which the turning mechanism 132 turns the turn support 124. More specifically, it is defined that the turning axis X1 is turned clockwise along the first axis distance changing orbit SC1 from the position close to the right side of the head P of the first axis distance changing orbit SC1, moved to the second axis distance changing orbit SC2 in the vicinity of the center A of the imaging region R, subsequently turned clockwise along the second axis distance changing orbit SC2, and finally returned to the first axis distance changing orbit SC1 in the vicinity of the center A of the imaging region R to return to the initial position.

When the X-ray detector 128 moves along the axis distance changing orbit SC, the moving speed (position) of the turning axis X1 in the axis distance changing orbit SC is controlled such that the generator 126 and the X-ray detector 128 turn while the state in which the center line XM of the X-ray emitted from the X-ray generator 126 passes through the center A of the imaging region R is maintained.

In the case that the X-ray CT imaging is performed with a part located close to the front of the head P as the imaging region R, using the turning mechanism 132, the X-ray generator 126 and the X-ray detector 128 are turned around the head P while the imaging region R is located therebetween. In the whole period of the turning movement, the turning axis X1 is moved along the axis distance changing orbit SC using the turning axis moving mechanism 134, thereby changing the distance between the X-ray detector 128 and the center A of the imaging region R. That is, in the case that the turning axis X1 moves along the axis distance changing orbit SC, the distance between the turning axis X1 and the center A of the imaging region R always fluctuates. For this reason, the distance between the X-ray detector 128 and the center A of the imaging region R also fluctuates at all times.

In the example of FIG. 15, in the timing at which the X-ray detector 128 is located on the −X direction side (see T1), the turning axis X1 is located at a position LC41 closer to the +X direction with respect to the center A of the imaging region R. In the timing at which the X-ray detector 128 is located closer to the combined direction of the component in the −X direction and the component in the +Y direction (see T2), the turning axis X1 on the mechanism is located at a position LC42 closer to the combined direction of the component in the +X direction and the component in the −Y direction with respect to the center A of the imaging region R. In the timing at which the X-ray detector 128 is located on the +Y direction side (see T3), the turning axis X1 is located at a position LC43 close to the −Y direction. In the timing at which the X-ray detector 128 is located closer to the combined direction of the component in the +X direction and the component in the +Y direction (see T4), the turning axis X1 on the mechanism is located at a position LC44 closer to the combined direction of the component in the −X direction and the component in the −Y direction with respect to the center A of the imaging region R. In the timing at which the X-ray detector 128 is located on the +X direction side (see T5), the turning axis X1 is located at a position LC45 closer to the −X direction with respect to the center A of the imaging region R.

In the timing at which the X-ray detector 128 is located closer to the combined direction of the component in the +X direction and the component in the −Y direction (see T6), the turning axis X1 on the mechanism is located at a position LC46 closer to the combined direction of the component in the +X direction and the component in the −Y direction with respect to the center A of the imaging region R. In the timing at which the X-ray detector 128 is located on the −Y direction side (see T7), the turning axis X1 is located at a position LC47 closer to the −Y direction with respect to the center A of the imaging region R. In the timing at which the X-ray detector 128 is located closer to the combined direction of the component in the −X direction and the component in the −Y direction (see T8), the turning axis X1 on the mechanism is located at a position LC48 closer to the combined direction of the component in the −X direction and the component in the −Y direction with respect to the center A of the imaging region R.

When the X-ray detector 128 moves from the position T1 to the position T5 through the positions T2, T3, T4, the turning axis X1 moves on the first axis distance changing orbit SC1. When the X-ray detector 128 moves from the position T5 to the position T1 through the positions T6, T7, T8, the turning axis X1 moves on the second axis distance changing orbit SC2.

In the first axis distance changing orbit SC1, the turning axis X1 is shifted toward the side of the X-ray generator 126 with respect to the center A of the region of interest R. For this reason, in the period in which the turning axis X1 moves along the first axis distance changing orbit SC1, the X-ray detector 128 is separated from the center A of the imaging region R by the distance in which the distance between the turning axis X1 and the center A of the imaging region R is subtracted from the distance L2 between the turning axis X1 and the X-ray detector 128. In the second axis distance changing orbit SC2, the turning axis X1 is shifted toward the side of the X-ray detector 128 with respect to the center A of the region of interest R. For this reason, in the period in which the turning axis X1 moves along the second axis distance changing orbit SC2, the X-ray detector 128 is separated from the center A of the imaging region R by the distance in which the distance between the turning axis X1 and the center A of the imaging region R is added to the distance L2 between the turning axis X1 and the X-ray detector 128. In any case, the distance between the turning axis X1 and the center A of the imaging region R always fluctuates. For this reason, the go-around orbit QC indicates an example of the orbit in which the X-ray detector 128 moves while changing the distance to the center A of the imaging region R in the whole circumference of the head P.

The turning axis X1 at the position (for example, the positions LC46, LC47, LC48) on the second axis distance changing orbit SC2 is shifted toward the side of the X-ray detector 128 with respect to the center A of the imaging region R, and therefore turning axis X1 is shifted toward the side on which the X-ray detector 128 moves away from the imaging region R. On the other hand, the turning axis X1 at the position (for example, the positions LC42, LC43, LC44) on the first axis distance changing orbit SC1 is shifted toward the side of the X-ray generator 126 with respect to the center A of the imaging region R, and therefore the turning axis X1 is shifted toward the side on which the X-ray detector 128 comes close to the imaging region R. For this reason, when passing through the portion located close to the rear of the head P, the X-ray detector 128 is largely separated from the imaging region R compared with the case that the X-ray detector 128 passes through the portion located close to the front of the head P.

In the third modification, the movement of the X-ray detector 128 is smoothly changed in the inner circumferential direction and the outer circumferential direction. That is, in order to cause the X-ray detector 128 to approach the imaging region R for the front side of the head P and to turn the X-ray detector 128 along the circular orbit QC moving away from the imaging region R on the rear side, it is necessary to change the distance of the X-ray detector 128. As in the third modification, when the X-ray detector 128 moves around the whole head P while changing the distance between the X-ray detector 128 and the center A of the imaging region R, the movement of the X-ray detector 128 can smoothly be changed in the inner circumferential direction and the outer circumferential direction. As a result, the X-ray detector 128 is hardly shaken, and the clear X-ray CT image is easily generated.

In particularly, when the X-ray detector 128 moves around the whole head P, the turning axis X1 on the mechanism moves in the period in which the X-ray detector 128 turns. Consequently, the movement of the X-ray detector 128 can smoothly be changed in the inner circumferential side and the outer circumference side, the X-ray detector 128 is hardly shaken, and the clear X-ray CT image is easily generated.

Because the go-around orbit QC of the X-ray detector 128 can be formed into an elliptic orbit along the outer circumference of the head P so as not to be separated from the circumference of the head P as much as possible, the X-ray detector 128 can keep the state in which the X-ray detector 128 comes close to the imaging region R while avoiding a possibility that the X-ray detector 128 contacts with the head P, and the image quality of the X-ray CT image can further be improved.

The fourth modification can obtain the same effect as in the second embodiment except for the effect obtained by the operations in which, when the X-ray detector 128 passes through the portion located close to the front side of the head P, the X-ray detector 128 moves while maintaining an equidistance from the center A of the imaging region R, and the remaining orbit is the orbit in which the device 128 moves while changing the distance to the center A of the imaging region R, and the effect derived from these operations.

<Fifth Modification>

The configuration that changes the curvatures of the go-around orbits of the X-ray generator 126 and the X-ray detector 128, in particular, the curvature of the X-ray detector 128 is mainly described in the second embodiment and the first to fourth modifications.

An example in which the X-ray detector 128 is turned along the go-around orbit, which comes close to the imaging region R with respect to the front side of the head P and moves away from the imaging region R with respect to the rear side, by changing the distance between the X-ray detector 128 and the center A of the imaging region R without changing the curvature of the go-around orbit of the X-ray detector 128 will be described in a fifth modification.

Figure 16:
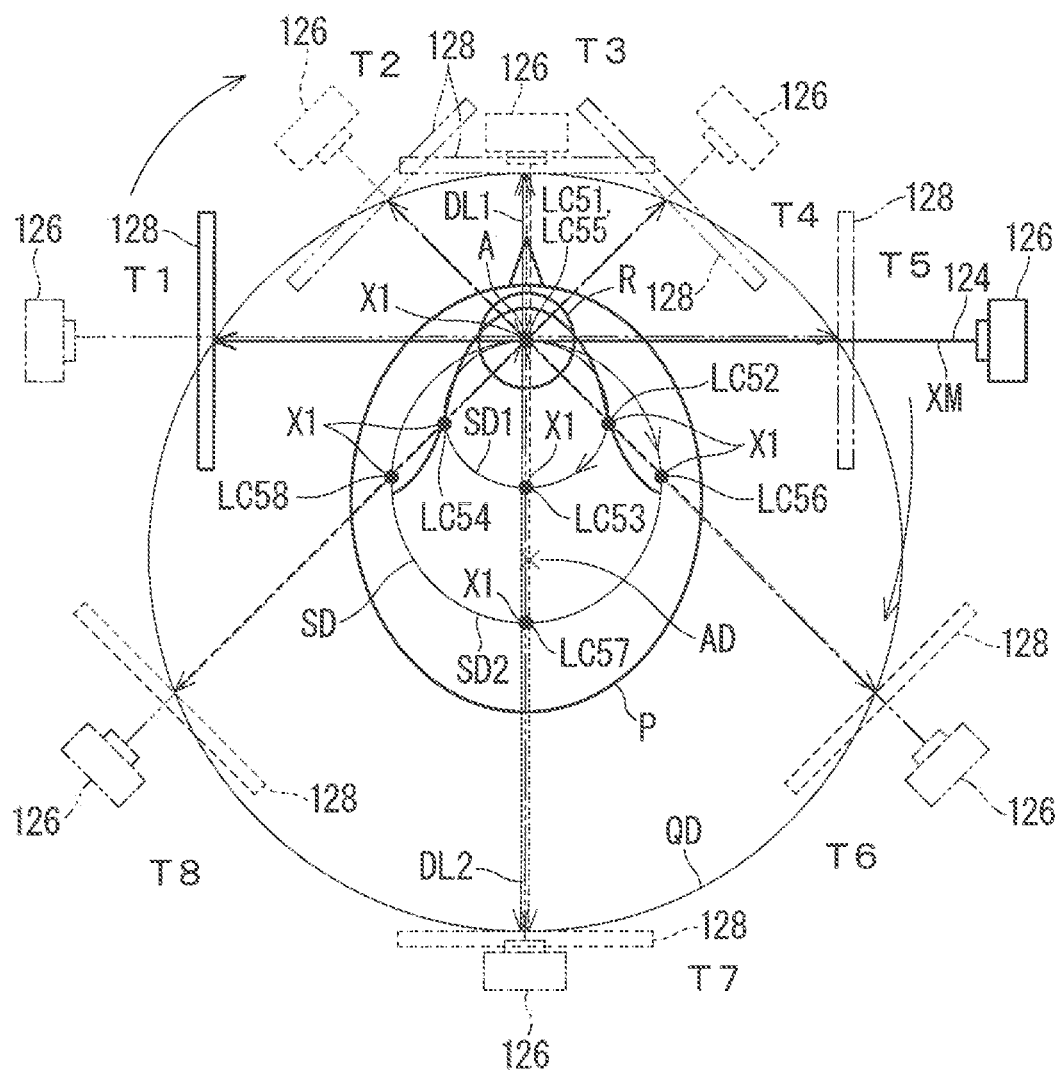
FIG. 16 is an explanatory view illustrating an example of a moving orbit of a turning axis and a go-around orbit of an X-ray detector according to a fifth modification.

In the fifth modification, a go-around orbit QD draws a circular shape as illustrated in FIG. 16. Because a center AD of the go-around orbit QD exists behind the center A of the imaging region R, the distance between the X-ray detector 128 and the center A of the imaging region R is changed while the turning support part 124 turns, and the X-ray detector 128 comes close to the imaging region R with respect to the front side of the head P, and moves away from the imaging region R with respect to the rear side.

In order to realize the above, an axis distance changing orbit SD of the turning axis X1 included in the movement control content of the turning axis X1 is illustrated in FIG. 16.

The axis distance changing orbit SD includes a first axis distance changing orbit SD1 and a second axis distance changing orbit SD2.

The first axis distance changing orbit SD1 indicates the movement locus of the turning axis X1 in the period in which the X-ray detector 128 passes through the portion located close to the front of the head P. The first axis distance changing orbit SD1 draws a circular shape or an elliptic shape. The central portion on the front side of the first axis distance changing orbit SD1 is located in the center A of the imaging region R, and spreads from the center A of the imaging region R to the side and rear of the head P.

The second axis distance changing orbit SD2 indicates the movement locus of the turning axis X1 in the period in which the X-ray detector 128 passes through the portion located close to the rear of the head P. The second axis distance changing orbit SD2 draws a circular shape or an elliptic shape larger than that of the first axis distance changing orbit SD1. The central portion on the front side of the second axis distance changing orbit SD2 is located in the center A of the imaging region R, and the first axis distance changing orbit SD1 and the second axis distance changing orbit SD2 are connected to each other at the central portion. The turning axis X1 can move from the first axis distance changing orbit SD1 to the second axis distance changing orbit SD2 at the center A of the imaging region R.

As the movement control content of the turning axis X1, it is defined that the turning axis moving mechanism 134 moves the turning axis X1 along the axis distance changing orbit SD in the whole period in which the turning mechanism 132 turns the turn support 124. More specifically, it is defined that the turning axis X1 is turned clockwise along the first axis distance changing orbit SD1, moved to the second axis distance changing orbit SD2 at the center A of the imaging region R, and turned clockwise along the second distance changing orbit SD2.

When the X-ray detector 128 moves in the go-around orbit QD, the moving speed (position) of the turning axis X1 is controlled in the axis distance changing orbit SD such that the X-ray generator 126 and the X-ray detector 128 turn while the state in which the center line XM of the X-ray emitted from the X-ray generator 126 passes through the center A of the imaging region R is maintained.

In the case that the X-ray CT imaging is performed with a part located close to the front of the head P as the imaging region R, using the turning mechanism 132, the X-ray generator 126 and the X-ray detector 128 are turned around the head P while the imaging region R is located therebetween. In the whole period of the turning movement, the turning axis X1 is moved along the axis distance changing orbit SD using the turning axis moving mechanism 134, thereby changing the distance between the X-ray detector 128 and the center A of the imaging region R. That is, in the case that the turning axis X1 moves along the axis distance changing orbit SD, the distance between the turning axis X1 and the center A of the imaging region R always fluctuates. For this reason, the distance between the X-ray detector 128 and the center A of the imaging region R also fluctuates at all times.

In the example of FIG. 16, in the timing at which the X-ray detector 128 is located on the −X direction side (see T1), the turning axis X1 is located at a position LC51 on the center A of the imaging region R. In the timing at which the X-ray detector 128 is located closer to the combined direction of the component in the −X direction and the component in the +Y direction (see T2), the turning axis X1 on the mechanism is located at a position LC52 closer to the combined direction of the component in the +X direction and the component in the −Y direction with respect to the center A of the imaging region R. In the timing at which the X-ray detector 128 is located on the +Y direction side (see T3), the turning axis X1 is located at a position LC53 close to the −Y direction. In the timing at which the X-ray detector 128 is located closer to the combined direction of the component in the +X direction and the component in the +Y direction (see T4), the turning axis X1 on the mechanism is located at a position LC54 closer to the combined direction of the component in the −X direction and the component in the −Y direction with respect to the center A of the imaging region R. In the timing at which the X-ray detector 128 is located on the +X direction side (see T5), the turning axis X1 is located at a position LC55 on the center A of the imaging region R.

In the timing at which the X-ray detector 128 is located closer to the combined direction of the component in the +X direction and the component in the −Y direction (see T6), the turning axis X1 on the mechanism is located at a position LC56 closer to the combined direction of the component in the +X direction and the component in the −Y direction with respect to the center A of the imaging region R. In the timing at which the X-ray detector 128 is located on the −Y direction side (see T7), the turning axis X1 is located at a position LC57 closer to the −Y direction with respect to the center A of the imaging region R. In the timing at which the X-ray detector 128 is located closer to the combined direction of the component in the −X direction and the component in the −Y direction (see T8), the turning axis X1 on the mechanism is located at a position LC58 closer to the combined direction of the component in the −X direction and the component in the −Y direction with respect to the center A of the imaging region R.

When the X-ray detector 128 moves from the position T1 to the position T5 through the positions T2, T3, T4, the turning axis X1 moves on the first axis distance changing orbit SD1. When the X-ray detector 128 moves from the position T5 to the position T1 through the positions T6, T7, T8, the turning axis X1 moves on the second axis distance changing orbit SD2.

In the first axis distance changing orbit SD1, the turning axis X1 is shifted toward the side of the X-ray generator 126 with respect to the center A of the region of interest R. For this reason, in the period in which the turning axis X1 moves along the first axis distance changing orbit SD1, the X-ray detector 128 is separated from the center A of the imaging region R by the distance in which the distance between the turning axis X1 and the center A of the imaging region R is subtracted from the distance L2 between the turning axis X1 and the X-ray detector 128. In the second axis distance changing orbit SD2, the turning axis X1 is shifted toward the side of the X-ray detector 128 with respect to the center A of the region of interest R. For this reason, in the period in which the turning axis X1 moves along the second axis distance changing orbit SD2, the X-ray detector 128 is separated from the center A of the imaging region R by the distance in which the distance between the turning axis X1 and the center A of the imaging region R is added to the distance L2 between the turning axis X1 and the X-ray detector 128. In any case, the distance between the turning axis X1 and the center A of the imaging region R always fluctuates. For this reason, the go-around orbit QD indicates an example of the orbit in which the X-ray detector 128 moves while changing the distance to the center A of the imaging region R in the whole circumference of the head P.

The turning axis X1 at the position (for example, the positions LC56, LC57, LC58) on the second axis distance changing orbit SD2 is shifted toward the side of the X-ray detector 128 with respect to the center A of the imaging region R, and therefore turning axis X1 is shifted toward the side on which the X-ray detector 128 moves away from the imaging region R. On the other hand, the turning axis X1 at the position (for example, the positions LC52, LC53, LC54) on the first axis distance changing orbit SD1 is shifted toward the side of the X-ray generator 126 with respect to the center A of the imaging region R, and therefore the turning axis X1 is shifted toward the side on which the X-ray detector 128 comes close to the imaging region R. For this reason, when passing through the portion located close to the rear of the head P, the X-ray detector 128 is largely separated from the imaging region R compared with the case that the X-ray detector 128 passes through the portion located close to the front of the head P.

As in the fifth modification, even if the circulating orbit QD is formed into the circular shape without changing the curvature of the go-around orbit of the X-ray detector 128, the distance between the X-ray detector 128 and the center A of the imaging region R is changed to turn the X-ray detector 128 along the go-around orbit, which comes close to the imaging region R with respect to the front side of the head P and moves away from the imaging region R with respect to the rear side.

<Sixth Modification>

Figure 17:
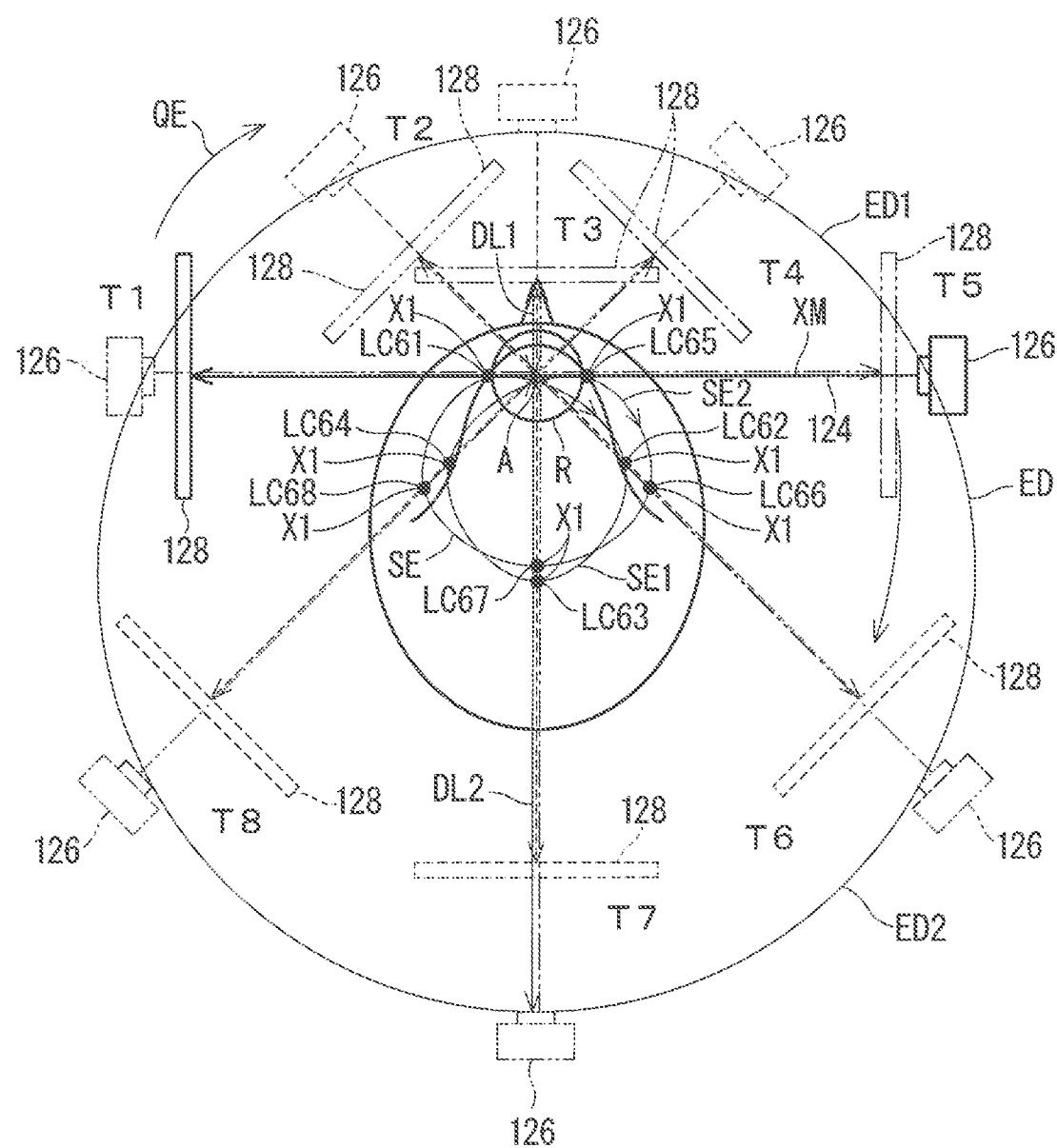
FIG. 17 is an explanatory view illustrating an example of a moving orbit of a turning axis and a go-around orbit of an X-ray detector according to a sixth modification.

The case that the X-ray generator 126 is turned in a circular shape is illustrated in a sixth modification. Strictly, a focus of the X-ray generator 126 moves on a circular X-ray generation orbit ED. In order to perform this, an axis distance changing orbit SE of the turning axis X1 included in the movement control content of the turning axis X1 is illustrated in FIG. 17.

The axis distance changing orbit SE includes a first axis distance changing orbit SE1 and a second axis distance changing orbit SE2.

The first axis distance changing orbit SE1 indicates the movement locus of the turning axis X1 in the period in which the X-ray detector 128 mainly passes through the portion located close to the front of the head P. The first axis distance changing orbit SE1 draws an elliptic shape or a circular shape. The central portion on the front side of the first axis distance changing orbit SE1 is located close to the center A of the imaging region R, and spreads from the center A of the imaging region R to the side and rear of the head P. Because the timing at which the turning axis X1 is located at a position LC61 (to be described later) and the timing at which the turning axis X1 is located at a position LC65 are also included, a curved region that protrudes from the closed curve on the −X side and the +X side from the vicinity of the center A of the imaging region R is included.

The second axis distance changing orbit SE2 indicates the movement locus of the turning axis X1 in the period in which the X-ray detector 128 mainly passes through the portion located close to the rear of the head P. The second axis distance changing orbit SE2 draws a partially elliptic shape. The central portion on the front side of the second axis distance changing orbit SE2 is the missing portion of the elliptic shape, and is located near the center A of the imaging region R. The first axis distance changing orbit SE1 and the second axis distance changing orbit SE2 are connected to each other at both ends reaching the missing portion. The turning axis X1 can move from the first axis distance changing orbit SE1 to the second axis distance changing orbit SE2 on the way to the center A of the imaging region R.

As the movement control content of the turning axis X1, it is defined that the turning axis moving mechanism 134 moves the turning axis X1 along the axis distance changing orbit SE in the whole period in which the turning mechanism 132 turns the turn support 124. More specifically, it is defined that the turning axis X1 is turned clockwise along a part of the first axis distance changing orbit SE1, moved to the second axis distance changing orbit SE2 on the way to the center A of the imaging region R, turned clockwise along the second axis distance changing orbit SE2, then returned to the first axis distance changing orbit SE1, and moved partially along the first axis distance changing orbit SE1.

When the X-ray detector 128 moves along the axis distance changing orbit SE, the moving speed (position) of the turning axis X1 in the axis distance changing orbit SE is controlled such that the generator 126 and the X-ray detector 128 turn while the state in which the center line XM of the X-ray emitted from the X-ray generator 126 passes through the center A of the imaging region R is maintained.

In the case that the X-ray CT imaging is performed with a part located close to the front of the head P as the imaging region R, using the turning mechanism 132, the X-ray generator 126 and the X-ray detector 128 are turned around the head P while the imaging region R is located therebetween. In the whole period of the turning movement, the turning axis X1 is moved along the axis distance changing orbit SE using the turning axis moving mechanism 134, thereby changing the distance between the X-ray detector 128 and the center A of the imaging region R. That is, in the case that the turning axis X1 moves along the axis distance changing orbit SE, the distance between the turning axis X1 and the center A of the imaging region R always fluctuates. For this reason, the distance between the X-ray detector 128 and the center A of the imaging region R also fluctuates at all times.

In the example of FIG. 17, in the timing at which the X-ray detector 128 is located on the −X direction side (see T1), the turning axis X1 is located at a position LC61 on the −X direction side. In the timing at which the X-ray detector 128 is located closer to the combined direction of the component in the −X direction and the component in the +Y direction (see T2), the turning axis X1 on the mechanism is located at a position LC62 closer to the combined direction of the component in the +X direction and the component in the −Y direction with respect to the center A of the imaging region R. In the timing at which the X-ray detector 128 is located on the +Y direction side (see T3), the turning axis X1 is located at a position LC63 closer to the −Y direction. In the timing at which the X-ray detector 128 is located closer to the combined direction of the component in the +X direction and the component in the +Y direction (see T4), the turning axis X1 on the mechanism is located at a position LC64 closer to the combined direction of the component in the −X direction and the component in the −Y direction with respect to the center A of the imaging region R. In the timing at which the X-ray detector 128 is located on the +X direction side (see T5), the turning axis X1 is located at a position LC65 on the +X direction side.

In the timing at which the X-ray detector 128 is located closer to the combined direction of the component in the +X direction and the component in the −Y direction (see T6), the turning axis X1 on the mechanism is located at a position LC66 closer to the combined direction of the component in the +X direction and the component in the −Y direction with respect to the center A of the imaging region R. In the timing at which the X-ray detector 128 is located on the −Y direction side (see T7), the turning axis X1 is located at a position LC67 closer to the −Y direction with respect to the center A of the imaging region R. In the timing at which the X-ray detector 128 is located closer to the combined direction of the component in the −X direction and the component in the −Y direction (see T8), the turning axis X1 on the mechanism is located at a position LC68 closer to the combined direction of the component in the −X direction and the component in the −Y direction with respect to the center A of the imaging region R.

The X-ray generation orbit ED is constructed with a first X-ray generation orbit ED1 and a second X-ray generation orbit ED2. When the X-ray detector 128 moves from the position T1 to the position T5 through the positions T2, T3, T4, the X-ray generator 126 moves on the first X-ray generation orbit ED1. When the X-ray detector 128 moves from the position T5 to the position T1 through the positions T6, T7, T8, the X-ray generator 126 moves on the second X-ray generation orbit ED2.

The turning axis X1 is shifted toward the side of the X-ray generator 126 in most of the period in which the X-ray generator 126 moves in the first X-ray generation orbit ED1. For this reason, in most of the period in which the turning axis X1 moves along the first axis distance changing orbit SE1, the X-ray detector 128 is separated from the center A of the imaging region R by the distance in which the distance between the turning axis X1 and the center A of the imaging region R is subtracted from the distance L2 between the turning axis X1 and the X-ray detector 128. The turning axis X1 is shifted toward the side of the X-ray detector 128 in the period in which the X-ray generator 126 moves in the second X-ray generation orbit ED2. For this reason, in the period in which the turning axis X1 moves along the second axis distance changing orbit SE2, the X-ray detector 128 is separated from the center A of the imaging region R by the distance in which the distance between the turning axis X1 and the center A of the imaging region R is added to the distance L2 between the turning axis X1 and the X-ray detector 128. In any case, the distance between the turning axis X1 and the center A of the imaging region R always fluctuates. For this reason, the go-around orbit QE indicates an example of the orbit in which the X-ray detector 128 moves while changing the distance to the center A of the imaging region R in the whole circumference of the head P.

The turning axis X1 at the position (for example, the positions LC66, LC67, LC68) on the second axis distance changing orbit SE2 is shifted toward the side of the X-ray detector 128 with respect to the center A of the imaging region R, and therefore turning axis X1 is shifted toward the side on which the X-ray detector 128 moves away from the imaging region R. On the other hand, the turning axis X1 at the position (for example, the positions LC62, LC63, LC64) on the first axis distance changing orbit SE1 is shifted toward the side of the X-ray generator 126 with respect to the center A of the imaging region R, and therefore the turning axis X1 is shifted toward the side on which the X-ray detector 128 comes close to the imaging region R. For this reason, when passing through the portion located close to the rear of the head P, the X-ray detector 128 is largely separated from the imaging region R compared with the case that the X-ray detector 128 passes through the portion located close to the front of the head P.

As in the sixth modification, even if the X-ray generator 126 is turned in the circular shape, the distance between the X-ray detector 128 and the center A of the imaging region R is changed to turn the X-ray detector 128 along the go-around orbit, which comes close to the imaging region R with respect to the front side of the head P and moves away from the imaging region R with respect to the rear side.

Through the control of the second preferred embodiment in FIG. 10, the control of the first modification in FIG. 12, the control of the third to sixth modifications in FIGS. 14 to 17, in the case that a part located close to the front of the head P is set to the imaging region R, the positions of the X-ray generator 126 and the X-ray detector 128 as seen from the Z direction, the alignment of the turning axis X1 on the mechanism located between the X-ray generator 126 and the X-ray detector 128, the turning axis X1 on the mechanism with respect to the imaging region R are controlled as follows.

When the X-ray generator 126 passes through the front of the head P while the X-ray detector 128 passes through the rear of the head P (X-ray detector rear passage timing), the turning axis X1 on the mechanism is moved in the direction from the X-ray generator 126 toward the X-ray detector 128 as compared with the case that the X-ray detector 128 passes through the front of the head P while the X-ray generator 126 passes through the rear of the head P. Conversely, when the X-ray detector 128 passes through the front of the head P while the X-ray generator 126 passes through the rear of the head P (X-ray detector front passage timing), the turning axis X1 on the mechanism is moved in the direction from the X-ray detector 128 toward the X-ray generator 126 as compared with the case that the X-ray generator 126 passes through the front of the head P while the X-ray detector 128 passes through the rear of the head P.

Assuming that +Py is a maximum displacement position in the +y direction of the turning axis X1 on the mechanism while the X-ray detector 128 moves in the go-around orbit Q, and that −Py is a maximum displacement position in the −y direction, preferably the control is performed such that the turning axis X1 on the mechanism reaches −Py in the X-ray detector front passage timing, and such that the turning axis X1 on the mechanism reaches +Py in the X-ray detector rear passage timing.

Between the X-ray detector front passage timing and the X-ray detector rear passage timing, preferably the turning axis X1 on the mechanism is displaced between −Py and +Py.

It is assumed that the same X-ray CT imaging device 110 is used, and the control of the second modification in FIG. 13 is compared to the control of the second preferred embodiment in FIG. 10 and the control of the third to sixth modifications in FIGS. 14 to 17. At this point, preferably the separation degree of the X-ray detector 128 with respect to the center A of the imaging region R in the X-ray detector rear passage timing in the control in FIGS. 14 to 17 is set larger than the separation degree of the X-ray detector 128 in FIG. 13 with respect to the center A of the imaging region R of the X-ray detector 128.

<Seventh Modification>

Figure 18:
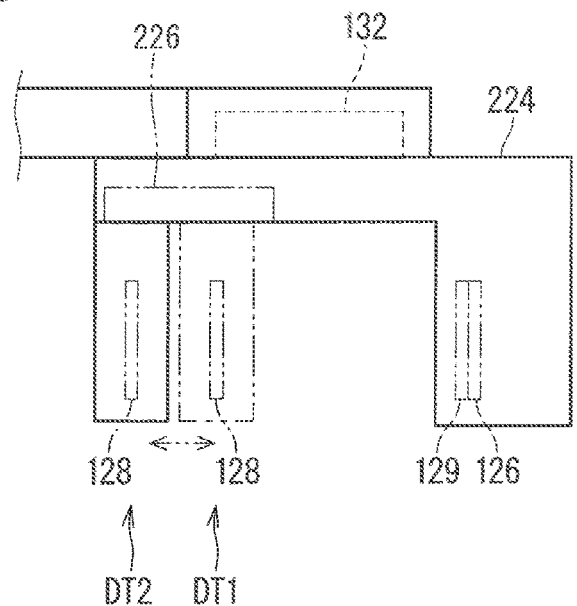
FIG. 18 is a schematic diagram illustrating a turning support according to a seventh modification.

As illustrated in a seventh modification of FIG. 18, the turning support 224 may include an X-ray detector moving mechanism 226 that moves the X-ray detector 128 along the X-ray irradiation direction. The X-ray detector moving mechanism 226 is constructed with a linear actuator such as a moving mechanism including a ball screw mechanism and motor, or a linear motor, and is incorporated in the turning support 224. The X-ray detector moving mechanism 226 moves the X-ray detector 128 along the extending direction of the turning support 224, thereby displacing the X-ray detector 128 between a position DT1 and a position DT2. The distance between the X-ray detector 128 located at the position DT2 and the X-ray generator 126 is larger than the distance between the X-ray detector 128 located at the position DT1 and the X-ray generator 126. For example, in the case that the apparatus has the configuration in which the whole dental arch region or the whole chin region is set to the imaging region R, the turning axis moving mechanism 134 may be omitted.

In the case that the X-ray CT imaging is performed with a part located close to the front of the head P as the imaging region R by moving the X-ray detector 128 using the X-ray detector moving mechanism 226, the X-ray detector 128 can be turned along the go-around orbit QF, which comes close to the imaging region R with respect to the front side of the head P and moves away from the imaging region R with respect to the rear side, by changing the distance between the X-ray detector 128 and the center A of the imaging region R.

Figure 19:
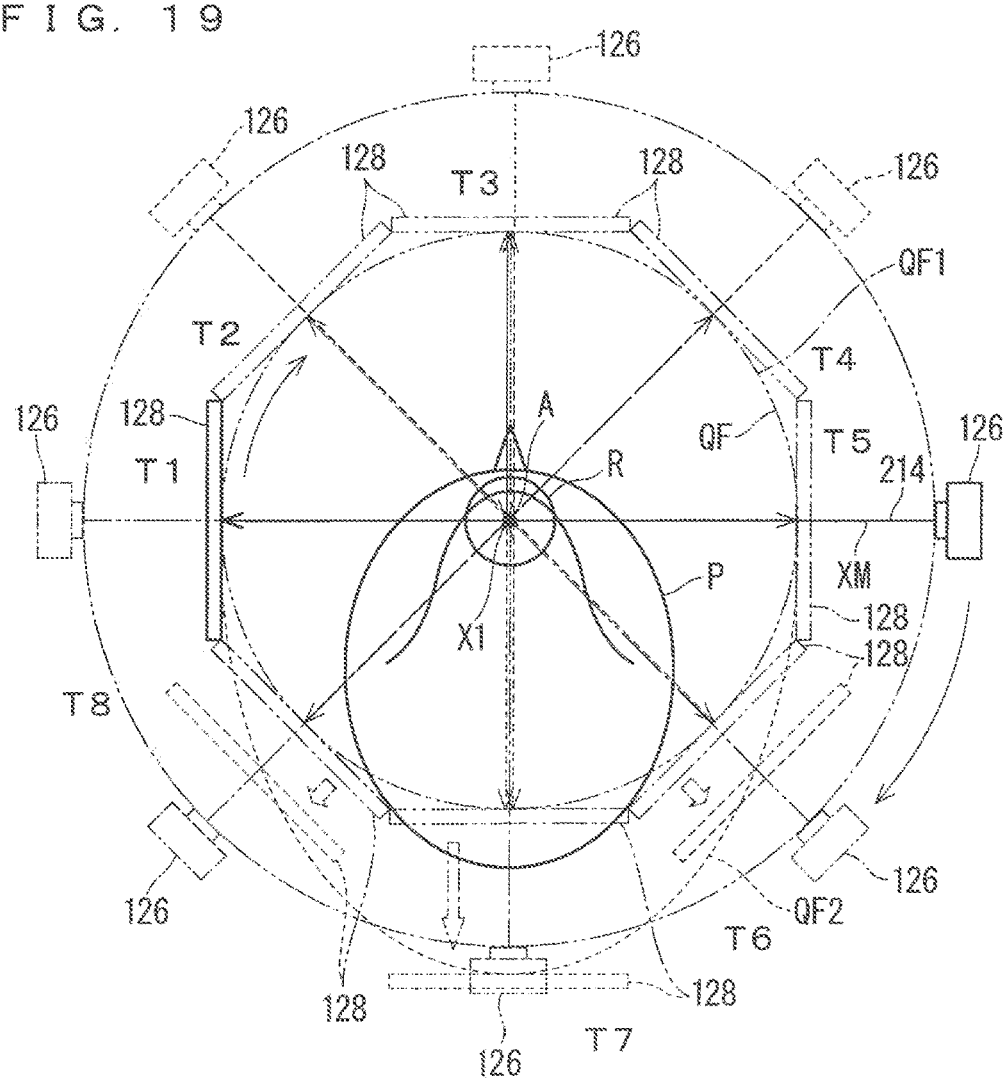
FIG. 19 is an explanatory view illustrating an example of a go-around orbit of an X-ray detector of the seventh modification.

FIG. 19 illustrates an example of the go-around orbit QF of the X-ray detector 128 of the seventh modification.

It is assumed that the X-ray generator 126 and the X-ray detector 128 are turned in the state in which the turning axis X1 is matched with the center A of the imaging region R and in the state in which the X-ray detector 128 is set at a fixed position (for example, located at the position DT1) from the turning axis X1.

Assuming that the imaging region R is the dental arch local imaging region R or the chin local imaging region R and is located in the front tooth region, the X-ray detector 128 remains at the position DT1 when turning in front of the head P. In this case, the X-ray detector 128 turns in an arcuate orbit QF1 (see positions T1 to T8) while maintaining a constant distance with respect to the imaging region R.

When the X-ray detector 128 turns in the rear of the head P, the X-ray detector 128 is kept at the position DT1. In this case, the X-ray detector 128 turns in the arcuate orbit QF1 while maintaining the constant distance with respect to the imaging region R. The X-ray detector 128 can come into contact with the rear of the head P (see the X-ray detector 128 indicated by the alternate long and short dashed line in FIG. 19).

For this reason, when the X-ray detector 128 turns in the rear of the head P, the X-ray detector 128 is moved from the position DT1 toward the position DT2 so as to be largely separated from the X-ray generator 126. For example, from when the X-ray detector 128 passes through right beside the head P toward when the X-ray generator 126 passes through just behind the head P, the distance between the X-ray detector 128 and the center A of the imaging region R is gradually increased, and the X-ray detector 128 is farthest from the center A of the imaging region R when the X-ray generator 126 passes through just behind the head P. That is, the X-ray detector 128 is located at the position DT2 just behind the head P. The X-ray detector 128 moves while drawing a semi-elliptic orbit QF2 greatly protruding toward the rear of the head P, and the X-ray detector 128 hardly contacts with the head P. As described above, the X-ray detector 128 moves in the semicircular arcuate portion of the arcuate orbit QF1 when turning in front of the head P, the X-ray detector 128 moves in the semi-elliptic orbit QF2 when turning in the rear of the head P, and the X-ray detector 128 moves in the go-around orbit QF constructed with the orbits QF1, QF2, so that the X-ray detector 128 hardly contact with the head P.

The X-ray generator 126 turns along the circular orbit centered on the center A of the imaging region R.

In this way, in the case that the X-ray CT imaging is performed with a part located close to the front of the head P as the imaging region R using the X-ray detector moving mechanism 226 that separately moves the X-ray detector 128 with respect to the X-ray generator 126 instead of the mechanism that moves the turning axis X1 as the distance changing mechanism, the turning mechanism 132 and the X-ray detector moving mechanism 226 cause the X-ray generator 126 and the X-ray detector 128 to turn around the head P while locating the imaging region R between the X-ray generator 126 and the X-ray detector 128, and cause the X-ray detector 128 to turn along the go-around orbit QF, which comes close to the imaging region R with respect to the front side of the head P and moves away from the imaging region R with respect to the rear side, by changing the distance between the X-ray detector 128 and the center A of the imaging region R.

In view of the actual situation illustrated in the drawings, regarding which region the imaging region R is, the orbit S (SN) of the turning axis X1 on the mechanism in FIG. 13 may be referred to as a temporal region orbit SSR, and the axis distance changing orbit S (Sα, SA, SB, SC, SD, SE) of the turning axis X1 on the mechanism in FIGS. 10, 12, 14, 15, 16, and 17 may be referred to as a frontal region axis distance changing orbit SFR.

When attention is paid on the presence or absence of the movement of the turning axis X1 on the mechanism, the orbit in which the turning axis X1 is fixed is referred to as an axis fixed orbit SFX like the orbit SN of the turning axis X1 on the mechanism in FIG. 13, and a displacement orbit of displacement amount exceeding zero of the turning axis X1 on the mechanism is referred to as a displacement orbit STR.

The orbit of the turning axis X1 on the mechanism may be referred to as follows while correlated with the turning range of the X-ray detector 128. With respect to the axis distance changing orbit S of the turning axis X1 on the mechanism in FIGS. 10, 12, 14, 15, 16, and 17, the orbits (Sα1, SA1, SB1, SC1, SD1, SE1) of the turning axis X1 on the mechanism in the period in which the X-ray detector 128 turns from the −X side to the +X side through the +Y side are referred to as a forward go-around orbit period orbit SFH, the orbits (Sα2, SA2, SB2, SC2, SD2, SE2) of the turning axis X1 on the mechanism in the period in which the X-ray detector 128 turns from the +X side to the −X side through the −Y side is referred to as a backward go-around orbit period orbit SRH, and it may be considered that the frontal region axis distance changing orbit SFR is constructed with the forward go-around orbit period orbit SFH and the backward go-around orbit period orbit SRH.

With respect to the orbit SN of the turning axis X1 on the mechanism in FIG. 13, the orbit (SN1) of the turning axis X1 on the mechanism in the period in which the X-ray detector 128 turns from the −X side to the +X side through the +Y side is referred to as the forward go-around orbit period orbit SFH, the orbit (SN2) of the turning axis X1 on the mechanism in the period in which the X-ray detector 128 turns from the +X side to the −X side through the −Y side is referred to as the backward go-around orbit period orbit SRH, and the temporal region orbit SSR may be constructed with the forward go-around orbit period orbit SFH and the backward go-around orbit period orbit SRH.

The setting example of the relationship of YLa1/YLa2>YL1/YL2 relating to the distance between the X-ray detector 128 and the center A with respect to the X-ray CT imaging of the first imaging region R1 and the X-ray CT imaging of the second imaging region R2 is described above. Alternatively, from another viewpoint, the control of axis movement may be set as follows.

It is assumed that a coordinate (Xr1, Yr1) is the XY coordinate of a position PR1 in the center A of the first imaging region R1, and that a coordinate (Xr2, Yr2) is the XY coordinate of a position PR2 in the center A of the second imaging region R2.

With respect to the imaging of the first imaging region R1, it is assumed that a coordinate (Xxr1, Yxr1) is the XY coordinate of a position Pxr1 of the turning axis X1 when the X-ray detector 128 passes through the rearmost point with respect to the head P (the point where the coordinate in the Y direction on the go-around orbit is minimized in the rear of the head P), and that DVxr1 is a bias amount (positive in the case of being biased to the side of the X-ray detector 128, and negative in the case of being biased to the side opposite to the X-ray detector 128) of Yxr1 to Yr1 in the direction in which the X-ray detector 128 exists (the direction from X-ray generator 126 toward the X-ray detector 128).

With respect to the imaging of the second imaging region R2, it is assumed that a coordinate (Xxr2, Yxr2) is the XY coordinate of a position Pxr2 of the turning axis X1 when the X-ray detector 128 passes through the rearmost point with respect to the head P (the point where the coordinate in the Y direction on the go-around orbit is minimized in the rear of the head P), and that DVxr2 is a bias amount of Yxr2 to Yr2 in the direction in which the X-ray detector 128 exists.

The movement controls of the turning axis X1 is performed such that DVxr1>DVxr2 holds. As a result, the X-ray detector 128 passes through a position further away in the rear with respect to the imaging center A in the case of imaging the first imaging region R1 as compared with the case of imaging the second imaging region R2.

An example of a numerical value will be given for ease of understanding.

When the XY coordinate (Xr1, Yr1) of PR1 is (0, 0), when the XY coordinate (Xr2, Yr2) of PR2 is (−50, −50), when the XY coordinate (Xxr1, Yxr1) of the position Pxr1 is (0, −60), and when the XY coordinate (Xxr2, Yxr2) of the position Pxr2 is (−50, −50), DVxr1=60 and DVxr2=0 are obtained.

Another example of the numerical value will be given.

When the XY coordinates (Xr1, Yr1) of PR1 is (0, 0), when the XY coordinate (Xr2, Yr2) of PR2 is (−50, −50), when the XY coordinate (Xxr1, Yxr1) of the position Pxr1 is (0, 0), and when the XY coordinate (Xxr2, Yxr2) of the position Pxr2 is (−50, 0), DVxr1=0 and DVxr2=−50 are obtained.

In the structural condition that the turning axis X1 on the mechanism is provided at the position closer to the X-ray detector 128 than the central position between the X-ray generator 126 and the X-ray detector 128, DVxr2≥0 is preferable. That is, with respect to the second imaging region R2, when the X-ray detector 128 passes through the rear of the head P, the turning axis X1 is retained at the position of the center A of the second imaging region R2 or shifted rearward from the center A. Because of DVxr1>DVxr2, with respect to the first imaging region R1, the turning axis X1 is shifted rearward from the center A of the first imaging region R1 when the X-ray detector 128 passes through the rear of the head P.

With respect to the imaging of the first imaging region R1, it is assumed that a coordinate (Xxf1, Yxf1) is the XY coordinate of a position Pxf1 of the turning axis X1 when the X-ray detector 128 passes through the frontmost point with respect to the head P (the point where the coordinate in the Y direction on the go-around orbit is maximized in front of the head P), and that DVxf1 is a bias amount of Yxf1 to Yr1 in the direction in which the X-ray detector 128 exists.

With respect to the imaging of the second imaging region R2, it is assumed that a coordinate (Xxf2, Yxf2) is the XY coordinate of a position Pxf2 of the turning axis X1 when the X-ray detector 128 passes through the frontmost point with respect to the head P (the point where the coordinate in the Y direction on the go-around orbit is maximized in front of the head P), and that DVxf2 is a bias amount of Yxf2 to Yr2 in the direction in which the X-ray detector 128 exists.

DVxr1>DVxf1 holds. As a result, in the case of imaging the first imaging region R1, the X-ray detector 128 passes through a position far away from the imaging center A in the case that the X-ray detector 128 passes through the rear as compared with the case that the X-ray detector 128 passes through the front.

Preferably DVxf1≤DVxf2 holds. As a result, in the case of imaging the first imaging region R1, the X-ray detector 128 passes through the position of the X-ray detector 128 at the equivalent position or a position nearer than the equivalent position as an approaching degree on the front side based on the imaging center A as compared with the case of imaging the second imaging region R2.

<Common Modification>

In each of the preferred embodiments and the modifications, the case of imaging the front tooth is described as an example in which the portion located close to the front of the head P is imaged. However, a nose, an eye, and paranasal sinus region may be set to the target as the case that a part located close to the front of the head P is set to the imaging region.

In the case of imaging the head, the X-ray CT imaging is performed on the head in an obliquely upward direction. In this case, in the direction orthogonal to the turning axis X1, the direction in which the head in the diagonally upward posture faces forward or the direction in which the chin faces may be set to the front side, and the opposite side may be set to the rear side.

The configurations described in the above preferred embodiments and the modifications can appropriately be combined as long as they are not inconsistent with each other.

For example, using the same X-ray CT imaging apparatus 110, the control of the second modification in FIG. 13 and the control of the second preferred embodiment in FIG. 10 may selectively be used depending on the designated position of the imaging region R. The control of the second modification in FIG. 13, the control of the second preferred embodiment in FIG. 10, and at least a part of the control of the third to sixth modifications in FIGS. 14 to 17 may selectively be used depending on the designated position of the imaging region R. The control of the second preferred embodiment in FIG. 10, a part of the control of the third to sixth modifications in FIGS. 14 to 17, and another part of the control of the third to sixth modifications in FIGS. 14 to 17 may selectively be used. At least the control of the second modification in FIG. 13 and the control of the second preferred embodiment in FIG. 10 may selectively be used depending on the designated position of the imaging region R, and at least a part of the control of the third to sixth modifications in FIGS. 14 to 17 may be selectively configured.

Preferably, the go-around orbit Q of the X-ray detector 128 can be changed in the case that at least a partial region located close to in front of the head P is set to the first imaging region R1 and in the case that a partial region on one of the right and left sides of the head P is set to the second imaging region R2.

The more detailed control may be performed when the imaging region R is located between the front tooth region and the molar region. For example, in the case that the imaging region R is the region on the dental arch that is somewhat closer to one of the right and left sides of the molar side from the front tooth region, the control of the axis distance changing orbit S in FIG. 10 is applied to the displacement of the turning axis X1 on the mechanism. However, the position LC12 of the turning axis X1 on the mechanism in the timing T7 is slightly shifted in the +y direction, and the separation degree of the X-ray detector 128 with respect to the imaging region R is adjusted so as to be slightly decreased. Although the position control of the turning axis X1 on the mechanism in FIG. 13 is applied to the position of the turning axis X1 on the mechanism in the case that the imaging region R slightly is shifted from one of the right and left molar regions toward the front tooth side, it is also conceivable that the position of the turning axis X1 on the mechanism in the timing T7 is slightly shifted in the −y direction as compared with the position in the timing T3. The adjustment may be performed stepwise according to the designated position of the imaging region R, or performed steplessly by coordinate calculation or the like.

A partial region located close to the front of the head P is set to the first imaging region R1, a partial region located close to one of the right and the left of the head P is set to the second imaging region R2, and a partial region on the dental arch between the front tooth region and the slightly left or right molar region is set to the third imaging region R3, the third imaging region R3 is between the first imaging region R1 and the second imaging region R2. At this point, similarly to the minimum value DL1, the maximum value DL2, the minimum value DLa1, the maximum value DLa2, the minimum value DLb1 and the maximum value DLb2 of the distance between the X-ray detector 128 and the center A mentioned above, also in the third imaging region R3, DLa1/DLa2>DLb1/DLb2>DL1/DL2 may be set. Alternatively, the distances YLb1, YLb2 between the X-ray detector 128 and the center A is considered similarly to YL1, YL2, YLa1, YLa2, and YLa1/YLa2>YLb1/YLb2>YL1/YL2 may be set.

With respect to the region along the dental arch, a boundary is provided between the partial region located close to the front of the head P and the partial region located close to one of the right and the left of the head P, and the region to which the frontal region axis distance changing orbit SFR is applied and the region to which the temporal region orbit SSR is applied may be divided.

Although the first imaging region R1 is described as a part located close to the front of the head P in the above configuration, a part of the region located close to the rear of the head P may be defined as the first imaging region R1. In this case, the pattern of control may be set to line symmetry in the front-rear direction of the head P. In this way, for example, it can contribute to a diagnosis of the presence or absence of a part of the brain tumor located close to the rear of the head.

While the invention has been shown and described in detail, the foregoing description is in all aspects illustrative and not restrictive. It is therefore understood that numerous modifications and variations can be devised without departing from the scope of the invention.

What is claimed is:

1. An X-ray CT imaging apparatus that performs X-ray CT imaging with a part of a head as an imaging region, the X-ray CT imaging apparatus comprising:
   an X-ray generator that generates an X-ray;
   an X-ray detector that detects said X-ray;
   a turning support that supports said X-ray generator and said X-ray detector in an opposed state;
   a shaft located between said X-ray generator and said X-ray detector;
   a first motor that turns said turning support around said shaft;
   a second motor that moves said shaft to change a distance of said X-ray detector with respect to a center of said imaging region when said first motor turns said turning support; and
   a processor that controls said first motor and said second motor;
   wherein
   when the X-ray CT imaging is performed with the part located close to a front of said head as said imaging region, using said first motor and said second motor, said processor causes said X-ray generator and said X-ray detector to turn around said head while locating said imaging region between said X-ray generator and said X-ray detector, and said processor changes the distance of said X-ray detector with respect to the center of said imaging region when the turning support turns around said head, so that said processor causes said X-ray detector to turn along a go-around orbit that comes close to said imaging region with respect to a front side of said head and moves away from said imaging region with respect to a rear side of said head, when the X-ray CT imaging is performed on a first imaging region including a front tooth region as said imaging region, said processor causes said X-ray detector to turn along said go-around orbit, and
   when the X-ray CT imaging is performed on a second imaging region including a molar region as said imaging region, using said first motor and said second motor, said processor causes said X-ray generator and said X-ray detector to turn around said head while positioning said imaging region between said X-ray generator and said X-ray detector such that a proportion of a minimum value of a distance between the center of said second imaging region and said X-ray detector to a maximum value of the distance is greater than a proportion of a minimum value of a distance between the center of said first imaging region and said X-ray detector to a maximum value of the distance.

2. The X-ray CT imaging apparatus according to claim 1, wherein said go-around orbit is an orbit that does not include a portion that is concave toward said imaging region.

3. The X-ray CT imaging apparatus according to claim 2, wherein said processor causes said X-ray detector to turn along said go-around orbit that has a circular or elliptical shape and comes close to said imaging region with respect to the front side of said head and moves away from said imaging region with respect to the rear side of said head.

4. The X-ray CT imaging apparatus according to claim 1, wherein
   said imaging region is a front tooth region, and
   said X-ray detector comes closest to said imaging region at the front of said head in said go-around orbit.

5. The X-ray CT imaging apparatus according to claim 1, wherein
   said go-around orbit includes an equidistance moving orbit in which said X-ray detector moves while keeping an equidistance with respect to the center of said imaging region when said X-ray detector passes through a portion located close to the front of said head, and
   a remaining orbit of said go-around orbit is a distance changing and moving orbit in which said X-ray detector moves while changing the distance to the center of said imaging region.

6. The X-ray CT imaging apparatus according to claim 1, wherein said go-around orbit is an orbit along which said X-ray detector moves while changing the distance with respect to the center of said imaging region in a whole circumference of said head.

7. The X-ray CT imaging apparatus according to claim 1, wherein said second motor moves said shaft in a direction crossing an axial direction of said shaft; and wherein said second motor moves said shaft in synchronization with the turning of said turning support about said shaft by said first motor, and said processor controls said go-around orbit of said X-ray detector with respect to said head by causing said turning support to perform combined movement.

8. The X-ray CT imaging apparatus according to claim 7, wherein
   said go-around orbit of said X-ray detector includes a first orbit approaching said imaging region on a side where said imaging region is biased in said head and a second orbit moving away from said imaging region on a side opposite to the side where said imaging region is biased in said head, and
   said go-around orbit is formed by a motion in which said second motor changes a position of said shaft in each of said first orbit and said second orbit in a direction parallel to the direction in which said imaging region is biased with respect to the center of said head.

9. The X-ray CT imaging apparatus according to claim 7, wherein in a period during which said X-ray detector turns, said shaft is located in the center of said imaging region in at least a part of the period in which said X-ray detector passes through a portion of said go-around orbit located close to the front of said head, and said shaft moves in another period.

10. The X-ray CT imaging apparatus according to claim 7, wherein said shaft moves during a whole period in which said X-ray detector turns.

11. The X-ray CT imaging apparatus according to claim 1, wherein said X-ray generator and said X-ray detector turn while a state in which a center line of said X-ray emitted from said X-ray generator passes through the center of said imaging region is maintained.

12. The X-ray CT imaging apparatus according to claim 1, wherein said second motor adjusts a curvature of said go-around orbit by adjusting the distance of said X-ray detector with respect to the center of said imaging region when said first motor turns said X-ray generator, and wherein when the X-ray CT imaging is performed with the part located close to the front of said head as said imaging region, using said first motor and said second motor, said processor causes said X-ray generator and said X-ray detector to turn around said head while locating said imaging region between said X-ray generator and said X-ray detector, and said processor changes the distance of said X-ray detector with respect to the center of said imaging region, so that said processor changes the curvature of said go-around orbit.

13. The X-ray CT imaging apparatus according to claim 12, wherein when the X-ray CT imaging is performed with the front tooth region as said imaging region, using said first motor and said second motor, said processor causes said X-ray generator and said X-ray detector to turn around said head while locating said imaging region between said X-ray generator and said X-ray detector, and said processor changes the curvature of said go-around orbit of said X-ray detector with respect to said head, so that said processor causes said X-ray detector to turn along said go-around orbit that comes close to said imaging region with respect to the front side of said head and moves away from said imaging region with respect to the rear side of said head, and when the X-ray CT imaging is performed with a region different from said front tooth region in said head as said imaging region, the distance between said X-ray detector and the center of said imaging region is kept constant, said processor causes said X-ray generator and said X-ray detector to turn around said head while locating said imaging region between said X-ray generator and said X-ray detector.

14. The X-ray CT imaging apparatus according to claim 1, wherein when the X-ray CT imaging is performed with the part located close to the front of said head as said imaging region, said processor causes said first motor to turn said X-ray generator and said X-ray detector at least 360°.

* * * * *